United States Patent
Apt et al.

(10) Patent No.: US 11,154,076 B2
(45) Date of Patent: *Oct. 26, 2021

(54) EICOSAPENTAENOIC ACID-PRODUCING MICROORGANISMS, FATTY ACID COMPOSITIONS, AND METHODS OF MAKING AND USES THEREOF

(71) Applicant: DSM IP Assets B.V., Te Heerlen (NL)

(72) Inventors: Kirk E. Apt, Ellicott City, MD (US); Paul Warren Behrens, Ellicott City, MD (US); Jon Milton Hansen, Chandler, AZ (US); Joseph W. Pfeifer, III, Westminster, MD (US); Tracey Lynn Stahl, Pasadena, MD (US); Ross Zirkle, Mt. Airy, MD (US)

(73) Assignee: DSM IP Assets B.V., Heerlen (NL)

( * ) Notice: Subject to any disclaimer, the term of this patent is extended or adjusted under 35 U.S.C. 154(b) by 501 days.

This patent is subject to a terminal disclaimer.

(21) Appl. No.: 15/889,842

(22) Filed: Feb. 6, 2018

(65) Prior Publication Data

US 2018/0295860 A1  Oct. 18, 2018

Related U.S. Application Data

(62) Division of application No. 12/729,013, filed on Mar. 22, 2010, now Pat. No. 9,924,733.

(60) Provisional application No. 61/296,456, filed on Jan. 19, 2010.

(51) Int. Cl.

| A23D 9/00 | (2006.01) |
|---|---|
| C12P 7/64 | (2006.01) |
| A61K 31/202 | (2006.01) |
| A23K 20/158 | (2016.01) |
| A61K 8/36 | (2006.01) |
| A61K 31/201 | (2006.01) |
| A61Q 19/00 | (2006.01) |
| A23L 2/52 | (2006.01) |
| A23C 9/152 | (2006.01) |
| A23D 9/007 | (2006.01) |
| C11B 1/10 | (2006.01) |
| C11B 3/04 | (2006.01) |
| A23L 33/00 | (2016.01) |
| A23L 33/115 | (2016.01) |
| A61K 35/68 | (2006.01) |
| A23K 10/12 | (2016.01) |
| A23K 50/00 | (2016.01) |
| A23K 50/40 | (2016.01) |
| A23K 50/80 | (2016.01) |
| C12N 1/10 | (2006.01) |
| C12N 1/12 | (2006.01) |
| C12R 1/89 | (2006.01) |
| C12R 1/90 | (2006.01) |

(52) U.S. Cl.
CPC .......... *A23K 20/158* (2016.05); *A23C 9/1528* (2013.01); *A23D 9/00* (2013.01); *A23D 9/007* (2013.01); *A23K 10/12* (2016.05); *A23K 50/00* (2016.05); *A23K 50/40* (2016.05); *A23K 50/80* (2016.05); *A23L 2/52* (2013.01); *A23L 33/115* (2016.08); *A23L 33/40* (2016.08); *A61K 8/361* (2013.01); *A61K 31/201* (2013.01); *A61K 31/202* (2013.01); *A61K 35/68* (2013.01); *A61Q 19/00* (2013.01); *C11B 1/10* (2013.01); *C11B 3/04* (2013.01); *C12N 1/105* (2021.05); *C12N 1/125* (2021.05); *C12P 7/6427* (2013.01); *C12P 7/6472* (2013.01); *A23V 2002/00* (2013.01); *A61K 2800/10* (2013.01); *C12R 2001/89* (2021.05); *C12R 2001/90* (2021.05); *Y02A 40/818* (2018.01)

(58) Field of Classification Search
None
See application file for complete search history.

(56) References Cited

U.S. PATENT DOCUMENTS

| 5,130,242 A * | 7/1992 | Barclay ................. A61K 31/20 435/134 |
|---|---|---|
| 5,550,156 A * | 8/1996 | Kyle ....................... A23L 33/12 514/547 |
| 8,207,363 B2 * | 6/2012 | Apt ......................... A61K 31/20 554/224 |
| 8,685,682 B2 * | 4/2014 | Damude ................... A61P 1/00 435/134 |
| 9,414,612 B2 * | 8/2016 | Apt ......................... A61Q 19/00 |
| 9,611,488 B2 | 4/2017 | Apt et al. |
| 9,649,287 B2 | 5/2017 | Apt et al. |
| 9,968,578 B2 | 5/2018 | Apt et al. |
| 10,253,132 B2 * | 4/2019 | Bloom .................. C08F 242/00 |
| 2003/0060509 A1 | 3/2003 | Elswyk |
| 2005/0115897 A1 | 6/2005 | Dueppen et al. |
| 2010/0239533 A1 * | 9/2010 | Apt ......................... A61K 36/02 424/93.1 |
| 2017/0216239 A1 | 8/2017 | Apt et al. |

FOREIGN PATENT DOCUMENTS

| WO | WO06022356 | 3/2006 |
|---|---|---|
| WO | WO2011090493 A1 | 7/2011 |

\* cited by examiner

*Primary Examiner* — Maria G Leavitt
(74) *Attorney, Agent, or Firm* — Xi Chen; Shannon McGarrah

(57) ABSTRACT

The present invention is directed to isolated microorganisms as well as strains and mutants thereof, biomasses, microbial oils, compositions, and cultures; methods of producing the microbial oils, biomasses, and mutants; and methods of using the isolated microorganisms, biomasses, and microbial oils.

6 Claims, No Drawings
Specification includes a Sequence Listing.

EICOSAPENTAENOIC ACID-PRODUCING MICROORGANISMS, FATTY ACID COMPOSITIONS, AND METHODS OF MAKING AND USES THEREOF

CROSS-REFERENCE TO RELATED APPLICATION

This application is a continuation of U.S. application Ser. No. 15/435,335, filed Feb. 17, 2017, which is a divisional of Ser. No. 14/709,899, filed May 12, 2015, abandoned, which is a continuation of U.S. application Ser. No. 12/729,013, filed Mar. 22, 2010, (U.S. Pat. No. 9,924,733), which claims the benefit of the filing date of U.S. Appl. No. 61/296,456, filed Jan. 19, 2010, which is hereby incorporated by reference in its entirety.

REFERENCE TO A SEQUENCE LISTING SUBMITTED ELECTRONICALLY

The content of the electronically submitted sequence listing ("sequence listing.txt", 5,061 bytes, created on Mar. 17, 2010) filed with the application is incorporated herein by reference in its entirety.

BACKGROUND OF THE INVENTION

Field of the Invention

The present invention is directed to isolated microorganisms as well as strains and mutants thereof, biomasses, microbial oils, compositions, and cultures; methods of producing the microbial oils, biomasses, and mutants; and methods of using the isolated microorganisms, biomasses, and microbial oils.

Background Art

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

Polyunsaturated fatty acids (PUFAs) are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 long chain polyunsaturated fatty acid (LC-PUFA) with a chain length of 22 carbons and 6 double bonds, often designated as "22:6 n-3." Other omega-3 LC-PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 LC-PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., Proc. Nutr. Soc. 58: 397-401 (1999). DHA, for example, accounts for approximately 15%-20% of lipids in the human cerebral cortex, 30%-60% of lipids in the retina, is concentrated in the testes and sperm, and is an important component of breast milk. Berge, J. P., and Barnathan, G. Adv. Biochem. Eng. Biotechnol. 96:49-125 (2005). DHA accounts for up to 97% of the omega-3 fatty acids in the brain and up to 93% of the omega-3 fatty acids in the retina. Moreover, DHA is essential for both fetal and infant development as well as maintenance of cognitive functions in adults. Id. Because omega-3 fatty acids are not synthesized de novo in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Thraustochytrids are microorganisms of the order Thraustochytriales. Thraustochytrids include members of the genus *Schizochytrium* and *Thraustochytrium* and have been recognized as an alternative source of omega-3 fatty acids, including DHA and EPA. See U.S. Pat. No. 5,130,242. Oils produced from these marine heterotrophic microorganisms often have simpler polyunsaturated fatty acid profiles than corresponding fish or microalgal oils. Lewis, T. E., Mar. Biotechnol. 1: 580-587 (1999). Strains of thraustochytrid species have been reported to produce omega-3 fatty acids as a high percentage of the total fatty acids produced by the organisms. U.S. Pat. No. 5,130,242; Huang, J. et al., J. Am. Oil. Chem. Soc. 78: 605-610 (2001); Huang, J. et al., Mar. Biotechnol. 5: 450-457 (2003). However, isolated thraustochytrids vary in the identity and amounts of LC-PUFAs produced, such that some previously described strains can have undesirable levels of omega-6 fatty acids and/or can demonstrate low productivity in culture. As such, a continuing need exists for the isolation of microorganisms demonstrating high productivity and desirable LC-PUFA profiles.

BRIEF SUMMARY OF THE INVENTION

The present invention is directed to an isolated microorganism of the species deposited under ATCC Accession No. PTA-10212.

The present invention is directed to an isolated microorganism having the characteristics of the species deposited under ATCC Accession No. PTA-10212.

The present invention is directed to an isolated microorganism comprising an 18s rRNA comprising a polynucleotide sequence of SEQ ID NO:1 or a polynucleotide sequence having at least 94% identity to SEQ ID NO:1.

The present invention is directed to an isolated microorganism comprising an 18s rRNA polynucleotide sequence that has at least 94% identity to an 18s rRNA polynucleotide sequence of the microorganism deposited under ATCC Accession No. PTA-10212.

The present invention is directed to an isolated microorganism of the species deposited under ATCC Accession No. PTA-10208, wherein the total fatty acids produced by the microorganism comprises more than about 10% by weight eicosapentaenoic acid.

The present invention is directed to an isolated microorganism having the characteristics of the species deposited under ATCC Accession No. PTA-10208, wherein the total fatty acids produced by the microorganism comprises more than about 10% by weight eicosapentaenoic acid.

The present invention is directed to an isolated microorganism that produces a triacylglycerol fraction, wherein eicosapentaenoic acid content of the triacylglycerol fraction is at least about 12% by weight.

In some embodiments, the isolated microorganism of the invention is a mutant strain.

The present invention is directed to an isolated microorganism deposited under ATCC Accession No. PTA-10212, PTA-10213, PTA-10214, PTA-10215, PTA-10208, PTA-10209, PTA-10210, or PTA-10211.

The present invention is directed to a biomass comprising any of the microorganisms of the invention or mixtures thereof.

The present invention is directed to an isolated biomass, wherein at least about 20% by weight of a dry cell weight of the biomass are fatty acids, wherein more than about 10% by weight of fatty acids is eicosapentaenoic acid, and wherein the fatty acids comprise less than about 5% by weight each of arachidonic acid and docosapentaenoic acid n-6. In some embodiments, at least about 25% by weight of the fatty acids is docosahexaenoic acid.

In some embodiments, the present invention is directed to an isolated biomass comprising triacylglycerol, wherein at least about 12% by weight of triacylglycerol is eicosapentaenoic acid.

In some embodiments, the present invention is directed to any of the isolated biomasses of the invention wherein the fatty acids further comprise less than about 5% by weight each of oleic acid, linoleic acid, linolenic acid, eicosenoic acid, and erucic acid.

The present invention is directed to an isolated culture comprising any of the microorganisms of the invention or mixtures thereof.

The present invention is directed to a food product, cosmetic, or pharmaceutical composition for a non-human animal or human, comprising any of the microorganisms or biomasses of the invention or mixtures thereof.

The present invention is directed to a microbial oil comprising at least about 20% by weight eicosapentaenoic acid and less than about 5% by weight each of arachidonic acid, docosapentaenoic acid n-6, oleic acid, linoleic acid, linolenic acid, eicosenoic acid, erucic acid, and stearidonic acid. In some embodiments, the microbial oil further comprises at least about 25% by weight docosahexaenoic acid.

The present invention is directed to a microbial oil comprising a triacylglycerol fraction of at least about 10% by weight, wherein at least about 12% by weight of the fatty acids in the triacylglycerol fraction is eicosapentaenoic acid, wherein at least about 25% by weight of the fatty acids in the triacylglycerol fraction is docosahexaenoic acid, and wherein less than about 5% by weight of the fatty acids in the triacylglycerol fraction is arachidonic acid.

The present invention is directed to a food product, cosmetic, or pharmaceutical composition for a non-human animal or human, comprising any of the microbial oils of the invention. In some embodiments, the food product is an infant formula. In some embodiments, the infant formula is suitable for premature infants. In some embodiments, the food product is a milk, a beverage, a therapeutic drink, a nutritional drink, or a combination thereof. In some embodiments, the food product is an additive for the non-human animal or human food. In some embodiments, the food product is a nutritional supplement. In some embodiments, the food product is an animal feed. In some embodiments, the animal feed is an aquaculture feed. In some embodiments, the animal feed is a domestic animal feed, a zoological animal feed, a work animal feed, a livestock feed, or a combination thereof.

The present invention is directed to a method for producing a microbial oil comprising omega-3 fatty acids, the method comprising: growing any of the isolated microorganisms of the invention or mixtures thereof in a culture to produce an oil comprising omega-3 fatty acids. In some embodiments, the method further comprises extracting the oil.

The present invention is directed to a method for producing a microbial oil comprising omega-3 fatty acids, the method comprising extracting an oil comprising omega-3 fatty acids from any of the biomasses of the invention. In some embodiments, the microbial oil is extracted using an organic solvent extraction process, for example hexane extraction. In some embodiments, the microbial oil is extracted using a solventless extraction process.

The present invention is directed to a microbial oil produced by a method of the invention.

The present invention is directed to a method for producing a biomass of the invention, comprising: growing any of the isolated microorganisms of the invention or mixtures thereof in a culture to produce a biomass.

The present invention is directed to a biomass produced by a method of the invention.

The present invention is directed to a method for producing a mutant strain of the invention, comprising: mutagenizing any of the microorganisms of the invention, and isolating the mutant strain.

The present invention is directed to use of any of the isolated microorganisms, biomasses, or microbial oils of the invention, or mixtures thereof, for the manufacture of a medicament for treatment of inflammation or a condition related thereto.

The present invention is directed to use of any of the isolated microorganisms, biomasses, or microbial oils of the invention, or mixtures thereof, for treatment of inflammation or a condition related thereto.

The present invention is directed to any of the isolated microorganisms, biomasses, or microbial oils of the invention, or mixtures thereof, for use in treatment of inflammation or a condition related thereto.

The present invention is directed to a method for treating inflammation or a condition related thereto in a subject in need thereof, comprising administering to the subject any of the isolated microorganisms, biomasses, or microbial oils of the invention, or mixtures thereof, and a pharmaceutically acceptable carrier.

DETAILED DESCRIPTION OF THE INVENTION

The present invention is directed to isolated microorganisms, as well as strains and mutants thereof, as well as biomasses, microbial oils, compositions, and cultures thereof. The present invention is directed to methods of producing microbial oils, biomasses, and mutants from the microorganisms of the invention, and methods of using the microorganisms, biomasses, and microbial oils. The microorganisms described herein are highly productive and produce unique fatty acid profiles, characterized in part by high levels of omega-3 fatty acids, in particular high levels of EPA.

Microorganisms

The invention is directed to isolated microorganisms and strains derived therefrom. A strain that is "derived" from an isolated microorganism of the invention can be a natural or artificial derivative such as, for example, a mutant, variant, or recombinant strain. The term "isolated" as used herein does not necessarily reflect the extent to which an isolate has been purified, but indicates isolation or separation from a native form or native environment. An isolate can include, but is not limited to, an isolated microorganism, an isolated biomass, an isolated culture, an isolated microbial oil, and an isolated sequence (such as an isolated polynucleotide sequence disclosed herein). The term "microorganism" as used herein includes, but is not limited to, the terms "microalgae," "thraustochytrid," and taxonomic classifications associated with any of the deposited microorganisms described herein. The terms "Thraustochytriales," "thraustochytrid," "*Schizochytrium*," and "*Thraustochytrium*" as used in reference to any of the microorganisms of the invention, including the deposited microorganisms described herein, are based on present taxonomic classifications including available phylogenetic information and are not intended to be limiting in the event that the taxonomic classifications are revised after the filing date of the present application.

In some embodiments, the invention is directed to an isolated microorganism of the species deposited under ATCC Accession No. PTA-10212. The isolated microorganism associated with ATCC Accession No. PTA-10212 is also known herein as *Thraustochytrium* sp. ATCC PTA-10212. The isolated microorganism associated with ATCC Accession No. PTA-10212 was deposited under the Budapest Treaty on Jul. 14, 2009 at the American Type Culture Collection, Patent Depository, 10801 University Boulevard, Manassas, Va. 20110-2209. In some embodiments, the invention is directed to an isolated strain deposited under ATCC Accession No. PTA-10212.

In some embodiments, the invention is directed to an isolated microorganism having the characteristics of the species deposited under ATCC Accession No. PTA-10212 or a strain derived therefrom. The characteristics of the species deposited under ATCC Accession No. PTA-10212 can include its growth and phenotypic properties (examples of phenotypic properties include morphological and reproductive properties), its physical and chemical properties (such as dry weights and lipid profiles), its gene sequences, and combinations thereof, in which the characteristics distinguish the species over previously identified species. In some embodiments, the invention is directed to an isolated microorganism having the characteristics of the species deposited under ATCC Accession No. PTA-10212, wherein the characteristics include an 18s rRNA comprising the polynucleotide sequence of SEQ ID NO:1 or a polynucleotide sequence having at least 94%, 95%, 96%, 97%, 98%, or 99% identity to SEQ ID NO:1, the morphological and reproductive properties of the species deposited under ATCC Accession No. PTA-10212, and the fatty acid profiles of the species deposited under ATCC Accession No. PTA-10212. In some embodiments, isolated microorganisms of the invention have phenotypic properties substantially identical to those of the microorganism deposited under ATCC Accession No. PTA-10212. In some embodiments, isolated microorganisms of the invention have growth properties substantially identical to those of the microorganism deposited under ATCC Accession No. PTA-10212. In some embodiments, the invention is directed to an isolated microorganism comprising an 18s rRNA comprising the polynucleotide sequence of SEQ ID NO:1 or a polynucleotide sequence having at least 94%, 95%, 96%, 97%, 98%, or 99% identity to SEQ ID NO:1. In some embodiments, the invention is directed to an isolated microorganism comprising an 18s rRNA polynucleotide sequence that has at least 94% identity to the 18s rRNA polynucleotide sequence of the microorganism deposited under ATCC Accession No. PTA-10212.

In some embodiments, the invention is directed to a mutant strain of the microorganism deposited under ATCC Accession No. PTA-10212. In further embodiments, the mutant strain is a strain deposited under ATCC Accession No. PTA-10213, PTA-10214, or PTA-10215. The microorganisms associated with ATCC Accession Nos. PTA-10213, PTA-10214, and PTA-10215 were deposited under the Budapest Treaty on Jul. 14, 2009 at the American Type Culture Collection, Patent Depository, 10801 University Boulevard, Manassas, Va. 20110-2209.

In some embodiments, the invention is directed to an isolated microorganism of the species deposited under ATCC Accession No. PTA-10208. The isolated microorganism associated with ATCC Accession No. PTA-10208 is also known herein as *Schizochytrium* sp. ATCC PTA-10208. The microorganism associated with ATCC Accession No. PTA-10208 was deposited under the Budapest Treaty on Jul. 14, 2009 at the American Type Culture Collection, Patent Depository, 10801 University Boulevard, Manassas, Va. 20110-2209. In some embodiments, the invention is directed to an isolated strain deposited under ATCC Accession No. PTA-10208.

In some embodiments, the invention is directed to an isolated microorganism of the species deposited under ATCC Accession No. PTA-10208, wherein the total fatty acids produced by the microorganism comprises more than about 10%, more than about 11%, more than about 12%, more than about 13%, more than about 14%, more than about 15%, more than about 16%, more than about 17%, more than about 18%, more than about 19%, or more than about 20% by weight EPA. In some embodiments, the invention is directed to an isolated microorganism of the species deposited under ATCC Accession No. PTA-10208, wherein the total fatty acids produced by the microorganism comprises about 10% to about 55%, about 10% to about 50%, about 10% to about 45%, about 10% to about 40%, about 10% to about 35%, about 10% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, about 20% to about 40%, about 20% to about 35%, or about 20% to about 30% by weight EPA.

In some embodiments, the invention is directed to an isolated microorganism having the characteristics of the species deposited under ATCC Accession No. PTA-10208, wherein the total fatty acids produced by the microorganism comprises more than about 10% by weight eicosapentaenoic acid. The characteristics of the microorganism deposited under ATCC Accession No. PTA-10208 include its growth and phenotypic properties (examples of phenotypic properties include morphological and reproductive properties), its physical and chemical properties (such as dry weights and lipid profiles), its gene sequences, and combinations thereof, in which the characteristics distinguish the species over previously identified species. In some embodiments, the invention is directed to an isolated microorganism having the characteristics of the species deposited under ATCC Accession No. PTA-10212, wherein the characteristics include an 18s rRNA comprising the polynucleotide sequence of SEQ ID NO:2, the morphological and reproductive properties of the species deposited under ATCC Accession No. PTA-10208, and the fatty acid profiles of the species deposited under ATCC Accession No. PTA-10208. In some embodiments, isolated microorganisms of the invention have physical and chemical properties substantially identical to those of the microorganism deposited under ATCC Accession No. PTA-10208.

In some embodiments, the invention is directed to a mutant strain of the microorganism deposited under ATCC Accession No. PTA-10208. In further embodiments, the mutant strain is a strain deposited under ATCC Accession No. PTA-10209, PTA-10210, or PTA-10211. The microorganisms associated with ATCC Accession Nos. PTA-10209, PTA-10210, and PTA-10211 were deposited under the Budapest Treaty on Sep. 25, 2009 at the American Type Culture Collection, Patent Depository, 10801 University Boulevard, Manassas, Va. 20110-2209.

In some embodiments, the invention is directed to an isolated microorganism of the invention that produces a triacylglycerol fraction, wherein the EPA content of the triacylglycerol fraction is at least about 12%, at least about 13%, at least about 14%, at least about 15%, at least about 16%, at least about 17%, at least about 18%, at least about 19%, or at least about 20% by weight. In some embodiments, the invention is directed to an isolated microorganism that produces a triacylglycerol fraction, wherein the EPA content of the triacylglycerol fraction is about 12% to about 55%, about 12% to about 50%, about 12% to about 45%, about 12% to about 40%, about 12% to about 35%, about 12% to about 30%, about 15% to about 45%, about 15% to about 40%, about 15% to about 35%, about 15% to about 30%, or about 20% to about 30% by weight.

In some embodiments, the invention is directed to a mutant, variant, or recombinant of an isolated microorganism of the invention that produces a triacylglycerol fraction, wherein the EPA content of the triacylglycerol fraction is at least about 10%, at least about 11%, at least about 12%, at least about 13%, at least about 14%, at least about 15%, at least about 16%, at least about 17%, at least about 18%, at least about 19%, or at least about 20% by weight. In some embodiments, the invention is directed to a mutant, variant, or recombinant of an isolated microorganism of the invention that produces a triacylglycerol fraction, wherein the EPA content of the triacylglycerol fraction is about 12% to about 55%, about 12% to about 50%, about 12% to about 45%, about 12% to about 40%, about 12% to about 35%, about 12% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, about 20% to about 40%, about 20% to about 35%, or about 20% to about 30% by weight. Mutant strains can be produced by well-known procedures. Common procedures include irradiation, treatment at high temperatures, and treatment with a mutagen. Variant strains can be other naturally occurring isolates and/or sub-isolates of the species described herein. Recombinant strains can be produced by any well-known methods in molecular biology for the expression of exogenous genes or alteration of endogenous gene function or expression. In some embodiments, the mutant, variant, or recombinant strain produces a higher amount of omega-3 fatty acids, particularly EPA, than the wild-type strain. In some embodiments, the mutant, variant, or recombinant strain produces a lower amount of one or more fatty acids, such as lower amounts of DHA, ARA, DPA n-6, or combinations thereof. In some embodiments, the mutant, variant, or recombinant strain produces a larger dry cell weight per liter of culture than the wild-type strain. Such mutant, variant, or recombinant strains are examples of strains derived from an isolated microorganism of the invention.

In some embodiments, an isolated microorganism of the invention, including mutants, variants, and recombinants thereof, comprises a fatty acid profile in one or more fractions isolated from the microorganism. The one or more fractions isolated from the microorganism include the total fatty acid fraction, the sterol esters fraction, the triacylglycerol fraction, the free fatty acid fraction, the sterol fraction, the diacylglycerol fraction, the polar fraction (including the phospholipid fraction), and combinations thereof. The fatty acid profile for a specific fraction can include any of the fatty acid profiles associated with the specific fraction as disclosed herein.

The invention is directed to a method of producing a mutant comprising mutagenizing any of the microorganisms of the invention and isolating the mutant strain.

Cultures and Isolated Biomasses

The invention is directed to a culture comprising one or more isolated microorganisms of the invention. Various fermentation parameters for inoculating, growing, and recovering microflora, such as microalgae and thraustochytrids, are known in the art. See, e.g., U.S. Pat. No. 5,130,242, incorporated by reference herein in its entirety. Liquid or solid media can contain natural or artificial sea water. Carbon sources for heterotrophic growth include, but are not limited to, glucose, fructose, xylose, saccharose, maltose, soluble starch, molasses, fucose, glucosamine, dextran, fats, oils, glycerol, sodium acetate, and mannitol. Nitrogen sources include, but are not limited to, peptone, yeast extract, polypeptone, malt extract, meat extract, casamino acid, corn steep liquor, organic nitrogen sources, sodium glutamate, urea, inorganic nitrogen sources, ammonium acetate, ammonium sulfate, ammonium chloride, and ammonium nitrate.

A typical media for growth of the microorganism deposited under ATCC Accession No. PTA-10212 is shown in Table 1:

TABLE 1

| PTA-10212 Vessel Media | | | |
|---|---|---|---|
| Ingredient | | concentration | ranges |
| $Na_2SO_4$ | g/L | 31.0 | 0-50, 15-45, or 25-35 |
| NaCl | g/L | 0.625 | 0-25, 0.1-10, or 0.5-5 |
| KCl | g/L | 1.0 | 0-5, 0.25-3, or 0.5-2 |
| $MgSO_4 \cdot 7H_2O$ | g/L | 5.0 | 0-10, 2-8, or 3-6 |
| $(NH_4)_2SO_4$ | g/L | 0.44 | 0-10, 0.25-5, or 0.05-3 |
| $MSG \cdot 1H_2O$ | g/L | 6.0 | 0-10, 4-8, or 5-7 |
| $CaCl_2$ | g/L | 0.29 | 0.1-5, 0.15-3, or 0.2-1 |
| T 154 (yeast extract) | g/L | 6.0 | 0-20, 0.1-10, or 1-7 |
| $KH_2PO_4$ | g/L | 0.8 | 0.1-10, 0.5-5, or 0.6-1.8 |
| Post autoclave (Metals) | | | |
| Citric acid | mg/L | 3.5 | 0.1-5000, 10-3000, or 3-2500 |
| $FeSO_4 \cdot 7H_2O$ | mg/L | 10.30 | 0.1-100, 1-50, or 5-25 |
| $MnCl_2 \cdot 4H_2O$ | mg/L | 3.10 | 0.1-100, 1-50, or 2-25 |
| $ZnSO_4 \cdot 7H_2O$ | mg/L | 3.10 | 0.01-100, 1-50, or 2-25 |
| $CoCl_2 \cdot 6H_2O$ | mg/L | 0.04 | 0-1, 0.001-0.1, or 0.01-0.1 |
| $Na_2MoO_4 \cdot 2H_2O$ | mg/L | 0.04 | 0.001-1, 0.005-0.5, or 0.01-0.1 |

TABLE 1-continued

PTA-10212 Vessel Media

| Ingredient | concentration | | ranges |
|---|---|---|---|
| CuSO$_4$•5H$_2$O | mg/L | 2.07 | 0.1-100, 0.5-50, or 1-25 |
| NiSO$_4$•6H$_2$O | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Vitamin B12 | mg/L | 0.16 | 0.01-100, 0.05-5, or 0.1-1 |
| Ca½-pantothenate | mg/L | 2.06 | 0.1-100, 0.1-50, or 1-10 |
| Biotin | mg/L | 3.21 | 0.1-100, 0.1-50, or 1-10 |
| Post autoclave (Carbon) | | | |
| Glycerol | g/L | 30.0 | 5-150, 10-100, or 20-50 |
| Nitrogen Feed: | | | |
| MSG•1H$_2$O | g/L | 17 | 0-150, 10-100, or 15-50 |

Typical cultivation conditions would include the following:
pH about 6.5-about 9.5, about 6.5-about 8.0, or about 6.8-about 7.8;
temperature: about 15-about 30 degrees Celsius, about 18-about 28 degrees Celsius, or about 21 to about 23 degrees Celsius;
dissolved oxygen: about 0.1-about 100% saturation, about 5-about 50% saturation, or about 10-about 30% saturation; and/or
glycerol controlled @: about 5-about 50 g/L, about 10-about 40 g/L, or about 15-about 35 g/L.

In some embodiments, the microorganism deposited under ATCC Accession No. PTA-10212, or a mutant, variant, or recombinant thereof, grows heterotrophically on glycerol as the carbon source but does not grow on glucose as the carbon source.

A typical media for growth of the microorganism deposited under ATCC Accession No. PTA-10208 is shown in Table 2:

TABLE 2

PTA-10208 Vessel Media

| Ingredient | concentration | | ranges |
|---|---|---|---|
| Na$_2$SO$_4$ | g/L | 8.8 | 0-25, 2-20, or 3-10 |
| NaCl | g/L | 0.625 | 0-25, 0.1-10, or 0.5-5 |
| KCl | g/L | 1.0 | 0-5, 0.25-3, or 0.5-2 |
| MgSO$_4$•7H$_2$O | g/L | 5.0 | 0-10, 2-8, or 3-6 |
| (NH$_4$)$_2$SO$_4$ | g/L | 0.42 | 0-10, 0.25-5, or 0.05-3 |
| CaCl$_2$ | g/L | 0.29 | 0.1-5, 0.15-3, or 0.2-1 |
| T 154 (yeast extract) | g/L | 1.0 | 0-20, 0.1-10, or 0.5-5 |
| KH$_2$PO$_4$ | g/L | 1.765 | 0.1-10, 0.5-5, or 1-3 |
| Post autoclave (Metals) | | | |
| Citric acid | mg/L | 46.82 | 0.1-5000, 10-3000, or 40-2500 |
| FeSO$_4$•7H$_2$O | mg/L | 10.30 | 0.1-100, 1-50, or 5-25 |
| MnCl$_2$•4H$_2$O | mg/L | 3.10 | 0.1-100, 1-50, or 2-25 |
| ZnSO$_4$•7H$_2$O | mg/L | 9.3 | 0.01-100, 1-50, or 2-25 |
| CoCl$_2$•6H$_2$O | mg/L | 0.04 | 0-1, 0.001-0.1, or 0.01-0.1 |
| Na$_2$MoO$_4$•2H$_2$O | mg/L | 0.04 | 0.001-1, 0.005-0.5, or 0.01-0.1 |
| CuSO$_4$•5H$_2$O | mg/L | 2.07 | 0.1-100, 0.5-50, or 1-25 |
| NiSO$_4$•6H$_2$O | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Ca½-pantothenate | mg/L | 3.33 | 0.1-100, 0.1-50, or 1-10 |
| Biotin | mg/L | 3.58 | 0.1-100, 0.1-50, or 1-10 |

TABLE 2-continued

PTA-10208 Vessel Media

| Ingredient | concentration | | ranges |
|---|---|---|---|
| Post autoclave (Carbon) | | | |
| Glucose | g/L | 30.0 | 5-150, 10-100, or 20-50 |
| Nitrogen Feed: | | | |
| NH$_4$OH | mL/L | 23.6 | 0-150, 10-100, or 15-50 |

Typical cultivation conditions would include the following:
pH about 6.5-about 8.5, about 6.5-about 8.0, or about 7.0-about 8.0;
temperature: about 17-about 30 degrees Celsius, about 20-about 28 degrees Celsius, or about 22 to about 24 degrees Celsius;
dissolved oxygen: about 2-about 100% saturation, about 5-about 50% saturation, or about 7-about 20% saturation; and/or
glucose controlled @: about 5-about 50 g/L, about 10-about 40 g/L, or about 20-about 35 g/L.

In some embodiments, the culture medium comprises at least about 0.1%, at least about 0.5%, at least about 1%, at least about 1.5%, at least about 2%, at least about 5%, at least about 7%, at least about 10%, at least about 20%, at least about 30%, at least about 40%, at least about 50%, at least about 60%, at least about 70%, at least about 80%, or at least about 90% dissolved oxygen, as a percentage of saturation level. In some embodiments, the culture medium comprises about 0.1% to about 2%, about 0.1% to about 5%, about 0.1% to about 10%, about 0.1% to about 20%, about 0.1% to about 30%, about 0.1% to about 50%, about 0.1% to about 100%, about 5% to about 10%, about 5% to about 20%, about 5% to about 30%, about 5% to about 50%, about 5% to about 100%, about 7% to about 10%, about 7% to about 20%, about 7% to about 30%, about 7% to about 50%, about 7% to about 100%, about 10% to about 20%, about 10% to about 30%, about 10% to about 50%, about 10% to about 100%, about 20% to about 30%, about 20% to about 50%, or about 20% to about 100% dissolved oxygen, as a percentage of saturation level.

The invention is directed to an isolated biomass of a microorganism of the invention. An isolated biomass of the invention is a harvested cellular biomass obtained by any conventional method for the isolation of a biomass, such as described in U.S. Pat. No. 5,130,242 and U.S. Appl. Publ. No. 2002/0001833, each of which are incorporated by reference herein in its entirety.

In some embodiments, the dry cell weight of the biomass isolated from each liter of culture is at least about 10 g, at least about 15 g, at least about 20 g, at least about 25 g, at least about 30 g, at least about 50 g, at least about 60 g, at least about 70 g, at least about 80 g, at least about 100 g, at least about 120 g, at least about 140 g, at least about 160 g, at least about 180 g, or at least about 200 g after growing for about 6 days to about 8 days at about 15° C. to about 30° C. in a culture medium of about pH 6.5 to about 9.5 comprising sources of carbon, nitrogen, and nutrients, and about 950 ppm to about 8500 ppm chloride ions. In some embodiments, the dry cell weight of the biomass isolated from each liter of culture is at least about 10 g, at least about 15 g, at least about 20 g, at least about 25 g, at least about 30 g, at least about 50 g, at least about 60 g, at least about 70 g, at least about 80 g, at least about 100 g, at least about 120 g, at least about 140 g, at least about 160 g, at least about 180 g, or at least about 200 g after growing for about 6 days, about 7 days, or about 8 days at about 15° C., about 16° C., about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, about pH 8.5, about pH 9, or about pH 9.5 comprising sources of carbon, nitrogen, and nutrients, and about 950 ppm to about 8500 ppm chloride ions. In some embodiments, the dry cell weight of the biomass isolated from each liter of culture is about 10 g to about 200 g after growing for about 6 days to about 8 days at about 15° C. to about 30° C. in a culture medium of about pH 6.5 to about pH 9.5 comprising sources of carbon, nitrogen, and nutrients, and about 950 ppm to about 8500 ppm chloride ions. In some embodiments, the dry cell weight of the biomass isolated from each liter of culture is about 10 g to about 200 g, about 10 g to about 100 g, about 10 g to about 50 g, about 15 g to about 200 g, about 15 g to about 100 g, about 15 g to about 50 g, about 20 g to about 200 g, about 20 g to about 100 g, about 20 g to about 50 g, about 50 g to about 200 g, or about 50 g to about 100 g after growing for about 6 days, about 7 days, or about 8 days at about 15° C., about 16° C., about 17° C., at about 18° C., at about 19° C., at about 20° C., at about 21° C., at about 22° C., at about 23° C., at about 24° C., at about 25° C., at about 26° C., at about 27° C., at about 28° C., at about 29° C., or at about 30° C. in a culture medium of about pH 6.5, about pH 7, about pH 7.5, about pH 8.0, about pH 8.5, about pH 9, or about pH 9.5 comprising sources of carbon, nitrogen, and nutrients, and about 950 ppm to about 8500 ppm chloride ions. In some embodiments, the isolated culture does not contain polyvinylpyrrolidone.

In some embodiments, the isolated culture has an omega-3 fatty acid productivity of at least about 0.2 g/L/day, at least about 0.3 g/L/day, at least about 0.4 g/L/day, at least about 0.5 g/L/day, at least about 1 g/L/day, at least about 1.2 g/L/day, at least about 1.5 g/L/day, at least about 1.7 g/L/day, at least about 2 g/L/day, at least about 3 g/L/day, at least about 3.5 g/L/day, at least about 4 g/L/day, at least about 4.5 g/L/day, at least about 5 g/L/day, at least about 6 g/L/day, or at least about 8 g/L/day after growing for about 6 days, about 7 days, or about 8 days at about 15° C. to about 30° C. in a culture medium of about pH 6.5 to about pH 8.5 or about pH 6.5 to about pH 9.5 comprising sources of carbon, nitrogen, and nutrients, and about 950 ppm to about 8500 ppm chloride ions. In some embodiments, the isolated culture has an omega-3 fatty acid productivity of about 0.2 g/L/day to about 20 g/L/day, about 0.4 g/L/day to about 20 g/L/day, about 0.4 g/L/day to about 2 g/L/day, about 1 g/L/day to about 2 g/L/day, about 1 g/L/day to about 20 g/L/day, about 2 g/L/day to about 15 g/L/day, about 2 g/L/day to about 10 g/L/day, about 3 g/L/day to about 10 g/L/day, about 4 g/L/day to about 9 g/L/day, about 4 g/L/day to about 8 g/L/day, about 4 g/L/day to about 7 g/L/day, or about 4 g/L/day to about 6 g/L/day after growing for about 6 days, about 7 days, or about 8 days at about 15° C. to about 30° C. in a culture medium of about pH 6.5 to about pH 9.5 comprising sources of carbon, nitrogen, and nutrients, and about 950 ppm to about 8500 ppm chloride ions.

In some embodiments, the isolated culture comprises an EPA productivity of at least about 0.2 g/L/day, at least about 0.3 g/L/day, at least about 0.4 g/L/day, at least about 0.5 g/L/day, at least about 0.6 g/L/day, at least about 0.7 g/L/day, at least about 0.8 g/L/day, at least about 0.9 g/L/day, at least about 1 g/L/day, at least about 1.2 g/L/day, at least about 1.5 g/L/day, at least about 1.7 g/L/day, at least about 2 g/L/day, at least about 3 g/L/day, at least about 4 g/L/day, or at least about 5 g/L/day after growing for about 6 days, about 7 days, or about 8 days at about 15° C. to about 30° C. in a culture medium of about pH 6.5 to about pH 8.5 or about pH 6.5 to about pH 9.5 comprising sources of carbon, nitrogen, and nutrients, and about 950 ppm to about 8500 ppm chloride ions. In some embodiments, the EPA productivity is about 0.2 g/L/day to about 5 g/L/day, about 0.2 g/L/day to about 4 g/L/day, about 0.2 g/L/day to about 3 g/L/day, about 0.2 g/L/day to about 2 g/L/day, about 0.2 g/L/day to about 1 g/L/day, about 0.2 g/L/day to about 0.8 g/L/day, about 0.2 g/L/day to about 0.7 g/L/day, about 1 g/L/day to about 5 g/L/day, about 1 g/L/day to about 4 g/L/day, about 1 g/L/day to about 3 g/L/day, or about 1 g/L/day to about 2 g/L/day after growing for about 6 days, about 7 days, or about 8 days at about 15° C. to about 30° C. in a culture medium of about pH 6.5 to about pH 8.5 or about pH 6.5 to about pH 9.5 comprising sources of carbon, nitrogen, and nutrients, and about 950 ppm to about 8500 ppm chloride ions. In some embodiments, any of the aforementioned EPA productivities are associated with any of the aforementioned omega-3 fatty acid productivities. In some embodiments, the culture further comprises a DHA productivity of about 0 g/L/day to about 5 g/L/day, about 0 g/L/day to about 4 g/L/day, about 0 g/L/day to about 3 g/L/day, about 0 g/L/day to about 2 g/L/day, about 0 g/L/day to about 1 g/L/day, about 0.2 g/L/day to about 5 g/L/day, about 0.2 g/L/day to about 4 g/L/day, about 0.2 g/L/day to about 3 g/L/day, about 0.2 g/L/day to about 2 g/L/day, about 0.2 g/L/day to about 1 g/L/day, about 1 g/L/day to about 5 g/L/day, about 2 g/L/day to about 5 g/L/day, about 2 g/L/day to about 4 g/L/day, or about 2 g/L/day to about 3 g/L/day. In some embodiments, the DHA productivity is less than about 5 g/L/day, less than about 4 g/L/day, less than about 3 g/L/day, less than about 2 g/L/day, less than about 1 g/L/day, less than about 0.5 g/L/day, less than about 0.2 g/L/day, or about 0 g/L/day.

In some embodiments, the fermentation volume (volume of culture) is at least about 2 liters, at least about 10 liters, at least about 50 liters, at least about 100 liters, at least about 200 liters, at least about 500 liters, at least about 1000 liters, at least about 10,000 liters, at least about 20,000 liters, at least about 50,000 liters, at least about 100,000 liters, at least about 150,000 liters, at least about 200,000 liters, or at least about 250,000 liters. In some embodiments, the fermentation volume is about 2 liters to about 300,000 liters, about 2 liters, about 10 liters, about 50 liters, about 100 liters, about 200 liters, about 500 liters, about 1000 liters, about 10,000 liters, about 20,000 liters, about 50,000 liters, about 100,000 liters, about 150,000 liters, about 200,000 liters, about 250,000 liters, or about 300,000 liters.

In some embodiments, the invention is directed to an isolated biomass comprising a fatty acid profile of the invention. In some embodiments, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the dry cell weight of the biomass are fatty acids. In some embodiments, greater than about 20%, greater than about 25%, greater than about 30%, greater than about 35%, greater than about 40%, greater than about 45%, greater than about 50%, greater than about 55%, or greater than about 60% of the dry cell weight of the biomass are fatty acids. In some embodiments, about 20% to about 55%, about 20% to about 60%, about 20% to about 70%, about 20% to about 80%, about 30% to about 55%, about 30% to about 70%, about 30% to about 80%, about 40% to about 60%, about 40% to about 70%, about 40% to about 80%, about 50% to about 60%, about 50% to about 70%, about 50% to about 80%, about 55% to about 70%, about 55% to about 80%, about 60% to about 70%, or about 60% to about 80% by weight of the dry cell weight of the biomass are fatty acids. In some embodiments, the biomass comprises more than about 10%, at least about 12%, at least about 15%, at least about 20%, at least about 25%, at least about 30%, about least about 35%, at least about 40%, or at least about 45% by weight of the fatty acids as EPA. In some embodiments, the biomass comprises about 10% to about 55%, about 12% to about 55%, about 15% to about 55%, about 20% to about 55%, about 20% to about 40%, or about 20% to about 30% by weight of the fatty acids as EPA. In some embodiments, the biomass comprises a triacylglycerol fraction, wherein at least about 12%, at least about 13%, at least about 14%, at least about 15%, at least about 16%, at least about 17%, at least about 18%, at least about 19%, or at least about 20% by weight of the triacylglycerol fraction is EPA. In some embodiments, the biomass comprises a triacylglycerol fraction, wherein the EPA content of the triacylglycerol fraction is from at least about 12% to about 55%, about 12% to about 50%, about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 20% to about 55%, about 20% to about 50%, about 20% to about 45%, at least about 20% to about 40%, at least about 20% to about 35%, or about 20% to about 30% by weight. In some embodiments, at least about 20%, at least about 25%, at least about 30%, at least about 35%, at least about 40%, at least about 50%, or at least about 60% by weight of the dry cell weight of the biomass is DHA. In some embodiments, about 20% to about 60%, about 25% to about 60%, about 25% to about 50%, about 25% to about 45%, about 30% to about 50%, or about 35% to about 50% by weight of the dry cell weight of the biomass is DHA. In some embodiments, the biomass comprises about 10% or less, about 9% or less, about 8% or less, about 7% or less, about 6% or less, about 5% or less, about 4% or less, about 3% or less, about 2% or less, or about 1% or less by weight of the fatty acids as DHA. In some embodiments, the biomass comprises about 1% to about 10%, about 1% to about 5%, about 2% to about 5%, about 3% to about 5%, or about 3% to about 10% by weight of the fatty acids as DHA. In some embodiments, the biomass is substantially free of DHA. In some embodiments, the biomass comprises about 0.1% to less than about 5%, about 0.1% to about 4%, about 0.1% to about 3%, about 0.1% to about 2%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight of the fatty acids as ARA. In some embodiments, the biomass comprises less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight of the fatty acids as ARA. In some embodiments, the biomass is substantially free of ARA. In some embodiments, the biomass comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight of the fatty acids as DPA n-6. In some embodiments, the biomass comprises about 5% or less, less than about 5%, about 4% or less, about 3% or less, about 2% or less, about 1% or less, about 0.75% or less, about 0.6% or less, or about 0.5% or less by weight of the fatty acids as DPA n-6. In some embodiments, the biomass is substantially free of DPA n-6. In some embodiments, the biomass comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), or combinations thereof.

The characteristics of an isolated biomass of the invention are associated with endogenous or native properties of the isolated biomass rather than exogenously introduced materials. In some embodiments, the isolated biomass does not contain polyvinylpyrrolidone or is not isolated from a culture containing polyvinylpyrrolidone.

The present invention is directed to a method of producing a biomass. In some embodiments, the method for producing a biomass of the invention comprises growing any of the isolated microorganisms of the invention or mixtures thereof in a culture to produce a biomass. The present invention is directed to a biomass produced by the method.

Microbial Oils

The invention is directed to a microbial oil comprising a fatty acid profile of the invention. A microbial oil of the invention is a "crude oil" or a "refined oil" comprising a triacylglycerol fraction of at least about 35% by weight. A "crude oil" is an oil that is extracted from the biomass of the microorganism without further processing. A "refined oil" is an oil that is obtained by treating a crude oil with standard processing of refining, bleaching, and/or deodorizing. See, e.g., U.S. Pat. No. 5,130,242, incorporated by reference herein in its entirety. A microbial oil also includes a "final oil" as described herein, which is a refined oil that has been diluted with a vegetable oil. In some embodiments, a final oil is a refined oil that has been diluted with high oleic sunflower oil. The term "microbial" as used herein includes, but is not limited to, the terms "microalgal," "thraustochytrid," and taxonomic classifications associated with any of the deposited microorganisms described herein. The terms "Thraustochytriales," "thraustochytrid," "*Schizochytrium*," and "*Thraustochytrium*" as used in reference to any of the microbial oils of the deposited microorganisms described herein are based on present taxonomic classifications including available phylogenetic information and are not intended to be limiting in the event that the taxonomic classifications are revised after the filing date of the present application.

In some embodiments, a fatty acid as described herein can be a fatty acid ester. In some embodiments, a fatty acid ester includes an ester of an omega-3 fatty acid, omega-6 fatty acid, and combinations thereof. In some embodiments, the fatty acid ester is a DHA ester, an EPA ester, or a combination thereof. In some embodiments, an oil or fraction thereof as described herein is esterified to produce an oil or fraction thereof comprising fatty acid esters. The term "ester" refers to the replacement of the hydrogen in the carboxylic acid group of the fatty acid molecule with another substituent. Typical esters are known to those in the art, a discussion of which is provided by Higuchi, T. and V. Stella in Pro-drugs as Novel Delivery Systems, Vol. 14, A.C.S. Symposium Series, Bioreversible Carriers in Drug Design, Ed. Edward B. Roche, American Pharmaceutical Association, Pergamon Press, 1987, and Protective Groups in Organic Chemistry, McOmie ed., Plenum Press, New York, 1973. Examples of esters include methyl, ethyl, propyl, butyl, pentyl, t-butyl, benzyl, nitrobenzyl, methoxybenzyl, benzhydryl, and trichloroethyl. In some embodiments, the ester is a carboxylic acid protective ester group, esters with aralkyl (e.g., benzyl, phenethyl), esters with lower alkenyl (e.g., allyl, 2-butenyl), esters with lower-alkoxy-lower-alkyl (e.g., methoxymethyl, 2-methoxyethyl, 2-ethoxyethyl), esters with lower-alkanoyloxy-lower-alkyl (e.g., acetoxymethyl, pivaloyloxymethyl, 1-pivaloyloxyethyl), esters with lower-alkoxycarbonyl-lower-alkyl (e.g., methoxycarbonylmethyl, isopropoxycarbonylmethyl), esters with carboxy-lower alkyl (e.g., carboxymethyl), esters with lower-alkoxycarbonyloxy-lower-alkyl (e.g., 1-(ethoxycarbonyloxy)ethyl, 1-(cyclohexyloxycarbonyloxy)ethyl), esters with carbamoyloxy-lower alkyl (e.g., carbamoyloxymethyl), and the like. In some embodiments, the added substituent is a linear or cyclic hydrocarbon group, e.g., a C1-C6 alkyl, C1-C6 cycloalkyl, C1-C6 alkenyl, or C1-C6 aryl ester. In some embodiments, the ester is an alkyl ester, e.g., a methyl ester, ethyl ester or propyl ester. In some embodiments, the ester substituent is added to the free fatty acid molecule when the fatty acid is in a purified or semi-purified state. Alternatively, the fatty acid ester is formed upon conversion of a triacylglycerol to an ester.

The present invention is directed to methods of producing microbial oils. In some embodiments, the method comprises growing any of the isolated microorganisms of the invention or mixtures thereof in a culture to produce a microbial oil comprising omega-3 fatty acids. In some embodiments, the method further comprises extracting the microbial oil. In some embodiments, the method comprises extracting a microbial oil comprising omega-3 fatty acids from any of the biomasses of the invention or mixtures thereof. In some embodiments, the method comprises heterotrophically growing the isolated microorganism, wherein the culture comprises a carbon source as described herein. The microbial oil can be extracted from a freshly harvested biomass or can be extracted from a previously harvested biomass that has been stored under conditions that prevent spoilage. Known methods can be used to culture a microorganism of the invention, to isolate a biomass from the culture, to extract a microbial oil from the biomass, and to analyze the fatty acid profile of oils extracted from the biomass. See, e.g., U.S. Pat. No. 5,130,242, incorporated by reference herein in its entirety. The invention is directed to a microbial oil produced by any of the methods of the invention.

In some embodiments, the microbial oil is extracted by an enzyme extraction method. In some embodiments, the microbial oil is extracted by a mechanical extraction method. In some embodiments, the mechanical extraction method comprises one or more of: (1) processing a pasteurized fermentation broth through a homogenizer to assist in cell lysis and release of oil from cells; (2) adding isopropyl alcohol to the fermentation broth following homogenization to break the oil and water emulsion; (3) centrifuging the mixture to recover the oil phase; and (4) drying under vacuum with addition of antioxidants. In some embodiments, the crude oil is purified. In some embodiments, purification of the crude oil comprises one or more of: (1) pumping the crude oil into a refining tank and heating the oil, followed by adding an acid solution with mixing; (2) adding a caustic solution to the oil after acid treatment; (3) reheating the crude oil and then centrifuging to separate the heavy phase from the refined oil; (4) removing the remaining polar compounds, trace metals, and oxidation products from the refined oil by using, for example, acid, TriSyl®, clay, and/or filtration; (5) chill filtering the bleached oil to further remove high melting point components from the oil to achieve the desired level of clarity; (6) heating the oil, after which the oil is then cooled and held for a period of time causing the high melting triglycerides and waxes to crystallize; (7) adding a filter aid to the chilled oil and then removing crystallized solids by filtration; (8) using a deodorizer after chill filtration, operated under high temperature and vacuum, to remove, for example, peroxides and any remaining low molecular weight compounds that can cause off-odor and flavors; (9) transferring the oil to the deodorizer feed tank, deaerating, and deodorizing, for example, in a packed column deodorizer; and (10) cooling, for example, under a nitrogen blanket at the end of the deodorization cycle and adding suitable antioxidants to the deodorized oil to provide oxidative stability.

In some embodiments, the microbial oil comprises a sterol esters fraction of about 0%, at least about 0.1%, at least about 0.2%, at least about 0.5%, at least about 1%, at least about 1.5%, at least about 2%, or at least about 5% by weight. In some embodiments, the microbial oil comprises a sterol esters fraction of about 0% to about 1.5%, about 0% to about 2%, about 0% to about 5%, about 1% to about 1.5%, about 0.2% to about 1.5%, about 0.2% to about 2%, or about 0.2% to about 5% by weight. In some embodiments, the microbial oil comprises a sterol esters fraction of about 5% or less, about 4% or less, about 3% or less, about 2% or less, about 1% or less, about 0.5% or less, about 0.3% or less, about 0.2% or less, about 0.5% or less, about 0.4% or less, about 0.3% or less, or about 0.2% or less by weight.

In some embodiments, the microbial oil comprises a triacylglycerol fraction of at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some embodiments, the microbial oil comprises a triacylglycerol fraction of about 35% to about 98%, about 35% to about 90%, about 35% to about 80%, about 35% to about 70%, about 35% to about 70%, about 35% to about 65%, about 40% to about 70%, about 40% to about 65%, about 40% to about 55%, about 40% to about 50%, about 65% to about 95%, about 75% to about 95%, about 75% to about 98%, about 80% to about 95%, about 80% to about 98%, about 90% to about 96%, about 90% to about 97%, about 90% to about 98%, about 90%, about 95%, about 97%, or about 98% by weight.

In some embodiments, the microbial oil comprises a diacylglycerol fraction of at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 10% to about 45%, about 10% to about 40%, about 10% to about 35%, about 10% to about 30%, about 15% to about 40%, about 15% to about 35%, or about 15% to about 30% by weight. In some embodiments, the microbial oil comprises a 1,2-diacylglycerol fraction of at least about 0.2%, at least about 0.3%, at least about 0.4%, at least about 0.5%, at least about 1%, at least about 5%, at least about 10%, at least about 11%, at least about 12%, at least about 13%, at least about 14%, at least about 15%, at least about 16%, at least about 17%, at least about 18%, at least about 19%, or at least about 20% by weight. In some embodiments, the microbial oil comprises a diacylglycerol fraction of about 0.2% to about 45%, about 0.2% to about 30%, about 0.2% to about 20%, about 0.2% to about 10%, about 0.2% to about 5%, about 0.2% to about 1%, about 0.2% to about 0.8%, about 0.4% to about 45%, about 0.4% to about 30%, about 0.4% to about 20%, about 0.4% to about 10%, about 0.4% to about 5%, about 0.4% to about 1%, about 0.4% to about 0.8%, about 0.5% to about 1%, about 0.5% to about 0.8%, about 10% to about 45%, about 10% to about 40%, about 10% to about 35%, about 10% to about 30%, about 15% to about 40%, about 15% to about 35%, about 15% to about 30%, or about 15% to about 25% by weight. In some embodiments, the microbial oil comprises a 1,3-diacylglycerol fraction of at least about 0.1%, at least about 0.2%, at least about 0.5%, at least about 1%, at least about 2%, at least about 2.5%, or at least about 3% by weight. In some embodiments, the microbial oil comprises a sterol fraction of at least about 0.3%, at least about 0.4%, at least about 0.5%, at least about 1%, at least about 1.5%, at least about 2%, or at least about 5% by weight.

In some embodiments, the microbial oil comprises a sterol fraction of about 0.3% to about 5%, about 0.3% to about 2%, about 0.3% to about 1.5%, about 0.5% to about 1.5%, about 1% to about 1.5%, about 0.5% to about 2%, about 0.5% to about 5%, about 1% to about 2%, or about 1% to about 5% by weight. In some embodiments, the microbial oil comprises a sterol fraction of about 5% or less, about 4% or less, about 3% or less, about 2% or less, about 1.5% or less, or about 1% or less by weight.

In some embodiments, the microbial oil comprises a phospholipid fraction of at least about 2%, at least about 5%, or at least about 8% by weight. In some embodiments, the microbial oil comprises a phospholipid fraction of about 2% to about 25%, about 2% to about 20%, about 2% to about 15%, about 2% to about 10%, about 5% to about 25%, about 5% to about 20%, about 5% to about 20%, about 5% to about 10%, or about 7% to about 9% by weight. In some embodiments, the microbial oil comprises a phospholipid fraction of less than about 20%, less than about 15%, less than about 10%, less than about 9%, or less than about 8% by weight. In some embodiments, the microbial oil is substantially free of phospholipids. In some embodiments, the microbial oil comprises unsaponifiables of less than about 2%, less than about 1.5%, less than about 1%, or less than about 0.5% by weight of the oil. The lipid classes present in the microbial oil, such as a triacylglycerol fraction, can be separated by flash chromatography and analyzed by thin layer chromatography (TLC), or separated and analyzed by other methods known in the art.

In some embodiments, the microbial oil and/or one or more fractions thereof selected from the triacylglycerol fraction, the free fatty acid fraction, the sterol fraction, the diacylglycerol fraction, and combinations thereof, comprises at least about 5%, at least about 10%, more than about 10%, at least about 12%, at least about 13%, at least about 14%, at least about 15%, at least about 16%, at least about 17%, at least about 18%, at least about 19%, at least about 20%, at least about 25%, at least about 30%, about least about 35%, at least about 40%, or at least about 45% by weight EPA. In some embodiments, the microbial oil and/or one or more fractions thereof selected from the triacylglycerol fraction, the free fatty acid fraction, the sterol fraction, the diacylglycerol fraction, and combinations thereof, comprises about 5% to about 55%, about 5% to about 50%, about 5% to about 45%, about 5% to about 40%, about 5% to about 35%, about 5% to about 30%, about 10% to about 55%, about 10% to about 50%, about 10% to about 45%, about 10% to about 40%, about 10% to about 35%, about 10% to about 30%, at least about 12% to about 55%, at least about 12% to about 50%, at least about 12% to about 45%, at least about 12% to about 40%, at least about 12% to about 35%, or at least about 12% to about 30%, about 15% to about 55%, about 15% to about 50%, about 15% to about 45%, about 15% to about 40%, about 15% to about 35%, about 15% to about 30%, about 15% to about 25%, about 15% to about 20%, about 20% to about 55%, about 20% to about 50%, about 20% to about 45%, about 20% to about 40%, or about 20% to about 30% by weight EPA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises at least about 5%, at least about 10%, at least about 15%, at least about 20%, at least about 25%, at least about 30%, at least about 35%, at least about 40%, at least about 50%, or at least about 60% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% to about 60%, about 5% to about 55%, about 5% to about 50%, about 5% to about 40%, about 10% to about 60%, about 10% to about 50%, about 10% to about 40%, about 20% to about 60%, about 25% to about 60%, about 25% to about 50%, about 25% to about 45%, about 30% to about 50%, about 35% to about 50%, or about 30% to about 40% by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 10% or less, about 9% or less, about 8% or less, about 7% or less, about 6% or less, about 5% or less, about 4% or less, about 3% or less, about 2% or less, or about 1% or less by weight DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 1% to about 10%, about 1% to about 5%, about 2% to about 5%, about 3% to about 5%, or about 3% to about 10% by weight of the fatty acids as DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DHA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.1% to about 5%, about 0.1% to less than about 5%, about 0.1% to about 4%, about 0.1% to about 3%, about 0.1% to about 2%, about 0.2% to about 5%, about 0.2% to less than about 5%, about 0.2% to about 4%, about 0.2% to about 3%, about 0.2% to about 2%, about 0.3% to about 2%, about 0.1% to about 0.5%, about 0.2% to about 0.5%, about 0.1% to about 0.4%, about 0.2% to about 0.4%, about 0.5% to about 2%, about 1% to about 2%, about 0.5% to about 1.5%, or about 1% to about 1.5% by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5% or less, less than about 5%, about 4% or less, about 3% or less, about 2% or less, about 1.5% or less, about 1% or less, about 0.5% or less, about 0.4% or less, about 0.3% or less, about 0.2% or less, or about 0.1% or less by weight ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of ARA. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 0.4% to about 2%, about 0.4% to about 3%, about 0.4% to about 4%, about 0.4% to about 5%, about 0.4% to less than about 5%, about 0.5% to about 1%, about 0.5% to about 2%, about 0.5% to about 3%, about 0.5% to about 4%, about 0.5% to about 5%, about 0.5% to less than about 5%, about 1% to about 2%, about 1% to about 3%, about 1% to about 4%, about 1% to about 5%, or about 1% to less than about 5% by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises about 5%, less than about 5%, about 4% or less, about 3% or less, about 2% or less, about 1% or less, about 0.75% or less, about 0.6% or less, or about 0.5% or less by weight DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, is substantially free of DPA n-6. In some embodiments, the microbial oil and/or one or more fractions thereof selected from the triacylglycerol fraction, the diacylglycerol fraction, the sterol fraction, the sterol esters fraction, the free fatty acids fraction, the phospholipid fraction, and combinations thereof, comprises fatty acids with about 5% or less, less than about 5%, about 4% or less, about 3% or less, or about 2% or less by weight of oleic acid (18:1 n-9), linoleic acid (18:2 n-6), linolenic acid (18:3 n-3), eicosenoic acid (20:1 n-9), erucic acid (22:1 n-9), stearidonic acid (18:4 n-3), or combinations thereof.

The triacylglycerol molecule contains 3 central carbon atoms (C(sn-1)H$_2$R1-(sn-2)H$_2$R2-C(sn-3)H$_2$R3), allowing for formation of different positional isomers. In some embodiments, the microbial oil comprises a triacylglycerol fraction in which at least about 2%, at least about 3%, at least about 5%, at least about 10%, at least about 15%, at least about 20%, at least about 30%, at least about 35%, or at least about 40% of the triacylglycerols in the triacylglycerol fraction contain DHA at two positions in the triacylglycerol (di-substituted DHA) selected from any two of the sn-1, sn-2, and sn-3 positions, based on the relative area percent of peaks on an HPLC chromatograph. In some embodiments, the microbial oil comprises a triacylglycerol fraction in which about 2% to about 55%, about 2% to about 50%, about 2% to about 45%, about 2% to about 40%, about 2% to about 35%, about 2% to about 30%, about 2% to about 25%, about 5% to about 55%, about 5% to about 50%, about 5% to about 45%, about 5% to about 40%, about 5% to about 35%, about 5% to about 30%, about 5% to about 25%, about 10% to about 55%, about 10% to about 50%, about 10% to about 45%, about 10% to about 40%, about 10% to about 35%, about 10% to about 30%, about 10% to about 25%, about 10% to about 20%, about 20% to about 40%, about 20% to about 35%, or about 20% to about 25% of the triacylglycerols in the triacylglycerol fraction contain EPA at two positions in the triacylglycerol selected from any two of the sn-1, sn-2, or sn-3 positions, based on the relative area percent of peaks on an HPLC chromatograph. In some embodiments, the microbial oil comprises a triacylglycerol fraction in which at least about 0.5%, at least about 1%, at least about 1.5%, or at least about 2% of the triacylglycerols in the triacylglycerol fraction contain DHA at all of the sn-1, sn-2, and sn-3 positions (tri-substituted DHA), based on the relative area percent of peaks on an HPLC chromatograph. In some embodiments, the microbial oil comprises a triacylglycerol fraction in which about 0.5% to about 5%, about 0.5% to about 3%, about 0.5% to about 2.5%, about 0.5% to about 2%, about 1% to about 5%, about 1% to about 3%, or about 1% to about 2% of the triacylglycerols in the triacylglycerol fraction contain DHA at all of the sn-1, sn-2, and sn-3 positions, based on the relative area percent of peaks on an HPLC chromatograph. In some embodiments, the microbial oil comprises a triacylglycerol fraction in which at least about 10%, at least about 15%, at least about 20%, at least about 25%, at least about 30%, at least about 35%, at least about 40%, at least about 45%, at least about 50%, at least about 55%, or at least about 60% of the triacylglycerols in the triacylglycerol fraction contain DHA at one position in the triacylglycerol selected from any one of the sn-1, sn-2, or sn-3 positions, based on the relative area percent of peaks on an HPLC chromatograph. In some embodiments, the microbial oil comprises a triacylglycerol fraction in which about 10% to about 80%, about 10% to about 70%, about 10% to about 60%, about 15% to about 80%, about 15% to about 75%, about 15% to about 70%, about 15% to about 65%, about 15% to about 60%, about 35% to about 80%, about 35% to about 75%, about 35% to about 65%, about 35% to about 60%, about 40% to about 80%, about 40% to about 75%, about 40% to about 70%, about 40% to about 65%, about 40% to about 60%, or about 40% to about 55% of the triacylglycerols in the triacylglycerol fraction contain DHA at one position in the triacylglycerol selected from any one of the sn-1, sn-2, and sn-3 positions, based on the relative area percent of peaks on an HPLC chromatograph.

Compositions

The invention is directed to compositions comprising a microorganism of the invention, an isolated biomass of the invention, a microbial oil of the invention, or combinations thereof.

A microorganism, biomass, or microbial oil of the invention can be further chemically or physically modified or processed based on the requirements of the composition by any known technique.

Microorganism cells or biomasses can be dried prior to use in a composition by methods including, but not limited to, freeze drying, air drying, spray drying, tunnel drying, vacuum drying (lyophilization), and a similar process. Alternatively, a harvested and washed biomass can be used directly in a composition without drying. See, e.g., U.S. Pat. Nos. 5,130,242 and 6,812,009, each of which is incorporated by reference herein in its entirety.

Microbial oils of the invention can be used as starting material to more efficiently produce a product enriched in a fatty acid such as EPA. For example, the microbial oils of the invention can be subjected to various purification techniques known in the art, such as distillation or urea adduction, to produce a higher potency product with higher concentrations of EPA or another fatty acid. The microbial oils of the invention can also be used in chemical reactions to produce compounds derived from fatty acids in the oils, such as esters and salts of EPA or another fatty acid.

A composition of the invention can include one or more excipients. As used herein, "excipient" refers to a component, or mixture of components, that is used in a composition of the present invention to give desirable characteristics to the composition, including foods as well as pharmaceutical, cosmetic, and industrial compositions. An excipient of the present invention can be described as a "pharmaceutically acceptable" excipient when added to a pharmaceutical composition, meaning that the excipient is a compound, material, composition, salt, and/or dosage form which is, within the scope of sound medical judgment, suitable for contact with tissues of human beings and non-human animals without excessive toxicity, irritation, allergic response, or other problematic complications over the desired duration of contact commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, $21^{st}$ ed. (2005). Inclusion of an excipient in a particular classification herein (e.g., "solvent") is intended to illustrate rather than limit the role of the excipient. A particular excipient can fall within multiple classifications.

Compositions of the invention include, but are not limited to, food products, pharmaceutical compositions, cosmetics, and industrial compositions.

In some embodiments, the composition is a food product. A food product is any food for non-human animal or human consumption, and includes both solid and liquid compositions. A food product can be an additive to animal or human foods. Foods include, but are not limited to, common foods; liquid products, including milks, beverages, therapeutic drinks, and nutritional drinks; functional foods; supplements; nutraceuticals; infant formulas, including formulas for pre-mature infants; foods for pregnant or nursing women; foods for adults; geriatric foods; and animal foods.

In some embodiments, a microorganism, biomass, or microbial oil of the invention can be used directly as or included as an additive within one or more of: an oil, shortening, spread, other fatty ingredient, beverage, sauce, dairy-based or soy-based food (such as milk, yogurt, cheese and ice-cream), a baked good, a nutritional product, e.g., as a nutritional supplement (in capsule or tablet form), a vitamin supplement, a diet supplement, a powdered drink, and a finished or semi-finished powdered food product. In some embodiments, the nutritional supplement is in the form of a vegetarian capsule that is not formed from and does not contain any components from an animal source.

A partial list of food compositions that can include a microbial oil of the invention includes, but is not limited to, soya based products (milks, ice creams, yogurts, drinks, creams, spreads, whiteners); soups and soup mixes; doughs, batters, and baked food items including, for example, fine bakery wares, breakfast cereals, cakes, cheesecakes, pies, cupcakes, cookies, bars, breads, rolls, biscuits, muffins, pastries, scones, croutons, crackers, sweet goods, snack cakes, pies, granola/snack bars, and toaster pastries; candy; hard confectionery; chocolate and other confectionery; chewing gum; liquid food products, for example milks, energy drinks, infant formula, carbonated drinks, teas, liquid meals, fruit juices, fruit-based drinks, vegetable-based drinks; multivitamin syrups, meal replacers, medicinal foods, and syrups; powdered beverage mixes; pasta; processed fish products; processed meat products; processed poultry products; gravies and sauces; condiments (ketchup, mayonnaise, etc.); vegetable oil-based spreads; dairy products; yogurt; butters; frozen dairy products; ice creams; frozen desserts; frozen yogurts; semi-solid food products such as baby food; puddings and gelatin desserts; processed and unprocessed cheese; pancake mixes; food bars including energy bars; waffle mixes; salad dressings; replacement egg mixes; nut and nut-based spreads; salted snacks such as potato chips and other chips or crisps, corn chips, tortilla chips, extruded snacks, popcorn, pretzels, potato crisps, and nuts; and specialty snacks such as dips, dried fruit snacks, meat snacks, pork rinds, health food bars and rice/corn cakes.

In some embodiments, a microbial oil of the invention can be used to supplement infant formula. Infant formula can be supplemented with a microbial oil of the invention alone or in combination with a physically refined oil derived from an arachidonic acid (ARA)-producing microorganism. An ARA-producing microorganism, for example, is *Mortierella alpina* or *Mortierella* sect. *schmuckeri*. Alternatively, infant formulas can be supplemented with a microbial oil of the invention in combination with an oil rich in ARA, including ARASCO® (Martek Biosciences, Columbia, Md.).

In some embodiments, the composition is an animal feed. An "animal" includes non-human organisms belonging to the kingdom Animalia, and includes, without limitation, aquatic animals and terrestrial animals. The term "animal feed" or "animal food" refers to any food intended for non-human animals, whether for fish; commercial fish; ornamental fish; fish larvae; bivalves; mollusks; crustaceans; shellfish; shrimp; larval shrimp; artemia; rotifers; brine shrimp; filter feeders; amphibians; reptiles; mammals; domestic animals; farm animals; zoo animals; sport animals; breeding stock; racing animals; show animals; heirloom animals; rare or endangered animals; companion animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; or rodents such as mice, rats, hamsters and guinea pigs; and so on. An animal feed includes, but is not limited to, an aquaculture feed, a domestic animal feed including pet feed, a zoological animal feed, a work animal feed, a livestock feed, and combinations thereof.

In some embodiments, the composition is a feed or feed supplement for any animal whose meat or products are consumed by humans, such as any animal from which meat, eggs, or milk is derived for human consumption. When fed to such animals, nutrients such as LC-PUFAs can be incorporated into the flesh, milk, eggs or other products of such animals to increase their content of these nutrients.

In some embodiments, the composition is a spray-dried material that can be crumbled to form particles of an appropriate size for consumption by zooplankton, artemia, rotifers, and filter feeders. In some embodiments, the zooplankton, artemia, or rotifers fed by the composition are in turn fed to fish larvae, fish, shellfish, bivalves, or crustaceans.

In some embodiments, the composition is a pharmaceutical composition. Suitable pharmaceutical compositions include, but are not limited to, an anti-inflammatory composition, a drug for treatment of coronary heart disease, a drug for treatment of arteriosclerosis, a chemotherapeutic agent, an active excipient, an osteoporosis drug, an antidepressant, an anti-convulsant, an anti-*Helicobacter pylori* drug, a drug for treatment of neurodegenerative disease, a drug for treatment of degenerative liver disease, an antibiotic, a cholesterol lowering composition, and a triacylglycerol lowering composition. In some embodiments, the composition is a medical food. A medical food includes a food that is in a composition to be consumed or administered externally under the supervision of a physician and that is intended for the specific dietary management of a condition, for which distinctive nutritional requirements, based on recognized scientific principles, are established by medical evaluation.

In some embodiments, the microbial oil can be formulated in a dosage form. Dosage forms can include, but are not limited to, tablets, capsules, cachets, pellets, pills, powders and granules, and parenteral dosage forms, which include, but are not limited to, solutions, suspensions, emulsions, and dry powders comprising an effective amount of the microbial oil. It is also known in the art that such formulations can also contain pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Administration forms can include, but are not limited to, tablets, dragees, capsules, caplets, and pills, which contain the microbial oil and one or more suitable pharmaceutically acceptable carriers.

For oral administration, the microbial oil can be combined with pharmaceutically acceptable carriers well known in the art. Such carriers enable the microbial oils of the invention to be formulated as tablets, pills, dragees, capsules, liquids, gels, syrups, slurries, suspensions and the like, for oral ingestion by a subject to be treated. In some embodiments, the dosage form is a tablet, pill or caplet. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinylpyrrolidone, agar, or alginic acid or a salt thereof such as sodium alginate. Pharmaceutical preparations that can be used orally include, but are not limited to, push-fit capsules made of gelatin, as well as soft, sealed capsules made of gelatin and a plasticizer, such as glycerol or sorbitol. In some embodiments, the dosage form is a vegetarian dosage form, in which the dosage form is not formed from and does not contain any components from an animal source. In some embodiments, the vegetarian dosage form is a vegetarian capsule.

In some embodiments, the composition is a cosmetic. Cosmetics include, but are not limited to, emulsions, creams, lotions, masks, soaps, shampoos, washes, facial creams, conditioners, make-ups, bath agents, and dispersion liquids. Cosmetic agents can be medicinal or non-medicinal.

In some embodiments, the composition is an industrial composition. In some embodiments, the composition is a starting material for one or more manufactures. A manufacture includes, but is not limited to, a polymer; a photographic photosensitive material; a detergent; an industrial oil; or an industrial detergent. For example, U.S. Pat. No. 7,259,006 describes use of DHA-containing fat and oil for production of behenic acid and production of photographic sensitive materials using behenic acid.

Methods of Using the Compositions

In some embodiments, the compositions can be used in the treatment of a condition in humans or non-human animals. In some embodiments, the compositions can be used for nutrition in humans or non-human animals.

The terms "treat" and "treatment" refer to both therapeutic treatment and prophylactic or preventative measures, wherein the object is to prevent or slow down (lessen) an undesired physiological condition, disease, or disorder, or to obtain beneficial or desired clinical results. For purposes of this invention, beneficial or desired clinical results include, but are not limited to, alleviation or elimination of the symptoms or signs associated with a condition, disease, or disorder; diminishment of the extent of a condition, disease, or disorder; stabilization of a condition, disease, or disorder, (i.e., where the condition, disease, or disorder is not worsening); delay in onset or progression of the condition, disease, or disorder; amelioration of the condition, disease, or disorder; remission (whether partial or total and whether detectable or undetectable) of the condition, disease, or disorder; or enhancement or improvement of a condition, disease, or disorder. Treatment includes eliciting a clinically significant response without excessive side effects. Treatment also includes prolonging survival as compared to expected survival if not receiving treatment.

In some embodiments, the composition is used to treat a condition, disease, or disorder such as acne, acute inflammation, age related maculopathy, allergy, Alzheimer's, arthritis, asthma, atherosclerosis, autoimmune disease, blood lipid disorder, breast cysts, cachexia, cancer, cardiac restenosis, cardiovascular diseases, chronic inflammation, coronary heart disease, cystic fibrosis, degenerative disorder of the liver, diabetes, eczema, gastrointestinal disorder, heart disease, high triacylglycerol levels, hypertension, hyperactivity, immunological diseases, inhibiting tumor growth, inflammatory conditions, intestinal disorders, kidney dysfunction, leukemia, major depression, multiple sclerosis, neurodegenerative disorder, osteoarthritis, osteoporosis, peroxisomal disorder, preeclampsia, preterm birth, psoriasis, pulmonary disorder rheumatoid arthritis, risk of heart disease, or thrombosis.

In some embodiments, the composition is used to increase the length of gestation of a fetus in the third trimester.

In some embodiments, the composition is used to control blood pressure.

In some embodiments, the composition is used to improve or maintain cognitive function.

In some embodiments, the composition is used to improve or maintain memory.

The composition or dosage form can be administered into the body of a subject by any route compatible with the composition or dosage form. A substance is considered to be "administered" if the substance is introduced into the body of the subject by the subject, or if another person, a machine, or a device introduces the substance into the body of the subject. "Administering," therefore, includes, e.g., self-administration, administration by others, and indirect administration. The term "continuous" or "consecutive," as used herein in reference to "administration," means that the frequency of administration is at least once daily. Note, however, that the frequency of administration can be greater than once daily and still be "continuous" or "consecutive," e.g., twice or even three times daily, as long as the dosage levels as specified herein are not exceeded. The means and methods for administration are known in the art and an artisan can refer to various pharmacologic references for guidance. For example, "Modern Pharmaceutics," Banker & Rhodes, Informa Healthcare, USA, 4th ed. (2002); and "Goodman & Gilman's The Pharmaceutical Basis of Therapeutics," McGraw-Hill Companies, Inc., New York, 10th ed. (2001) can be consulted.

By "subject," "individual," or "patient" is meant any subject, whether human or non-human, for whom diagnosis, prognosis, therapy, or administration of the composition or dosage form is desired. Mammalian subjects include, but are not limited to, humans; domestic animals; farm animals; zoo animals; sport animals; pet animals such as dogs, cats, guinea pigs, rabbits, rats, mice, or horses; primates such as monkeys (e.g., cebus, rhesus, African green, patas, cynomolgus, and cercopithecus), apes, orangutans, baboons, gibbons, and chimpanzees; canids such as dogs and wolves; felids such as cats, lions, and tigers; equids such as horses, donkeys, and zebras; food animals such as cows, cattle, pigs, and sheep; ungulates such as deer and giraffes; rodents such as mice, rats, hamsters and guinea pigs; and so on. The term subject also encompasses model animals, e.g., disease model animals. In some embodiments, the term subject includes valuable animals, either economically or otherwise, e.g., economically important breeding stock, racing animals, show animals, heirloom animals, rare or endangered animals, or companion animals. In certain embodiments, the subject is a human subject. In certain embodiments, the subject is a non-human subject.

The composition can be administered as a "nutritional amount," "therapeutically effective amount," a "prophylactically effective amount," a "therapeutic dose," or a "prophylactic dose." A "nutritional amount" refers to an amount effective, at dosages and for periods of time necessary, to achieve a desired nutritional result. A nutritional result can be, e.g., increased levels of a desirable fatty acid component in a subject. A "therapeutically effective amount" or "therapeutic dose" refers to an amount effective, at dosages and for periods of time necessary, to achieve a desired therapeutic result. A therapeutic result can be, e.g., lessening of symptoms, prolonged survival, improved mobility, and the like. A therapeutic result need not be a "cure." A "prophylactically effective amount" or "prophylactic dose" refers to an amount effective, at dosages and for periods of time necessary, to achieve the desired prophylactic result. Typically, since a prophylactic dose is used in subjects prior to or at an earlier stage of disease, a prophylactically effective amount will be less than a therapeutically effective amount for treatment of an advanced stage of disease.

Various dosage amounts of the composition, dosage form, or pharmaceutical composition can be administered to a subject, based on the amount of EPA or other fatty acid component of the microorganism, biomass, or microbial oil to be administered to the subject. The terms "daily dosage," "daily dosage level," and "daily dosage amount" refer herein to the total amount of EPA or other fatty acid component administered per day (per 24 hour period). Thus, for example, administration of EPA to a subject at a daily dosage of 2 mg means that the subject receives a total of 2 mg of EPA on a daily basis, whether the EPA is administered as a single dosage form comprising 2 mg EPA, or alternatively, four dosage forms comprising 0.5 mg EPA each (for a total of 2 mg EPA). In some embodiments, the daily amount of EPA is administered in a single dosage form, or in two dosage forms. The dosage forms of the present invention can be taken in a single application or multiple applications. For example, if four tablets are taken daily, each tablet comprising 0.5 mg EPA, then all four tablets can be taken once daily, or 2 tablets can be taken twice daily, or 1 tablet can be taken every 6 hours. In some embodiments, the daily dosage is about 100 mg to about 15 g of EPA. In some embodiments, the daily dosage is about 0.5 mg to about 250 mg, about 100 mg to about 250 mg, about 100 mg to about 500 mg, about 100 mg to about 1 g, about 1 g to about 2.5 g, about 1 g to about 5 g, about 1 g to about 10 g, about 1 g to about 15 g, about 5 g to about 10 g, about 5 g to about 15 g, about 10 g to about 15 g, about 100 mg to about 10 g, about 100 mg to about 5 g, or about 100 mg to about 2.5 g of EPA, DHA, or a combination thereof. In some embodiments, the composition is a dosage form that comprises about 0.5 mg to about 250 mg, 100 mg to about 250 mg, about 0.5 mg to about 500 mg, about 100 mg to about 500 mg, about 0.5 mg to about 1 g, or about 100 mg to about 1 g of EPA, DHA, or a combination thereof per dosage form.

Administration of the compositions or dosage forms of the present invention can be achieved using various regimens. For example, in some embodiments, administration occurs daily on consecutive days, or alternatively, occurs every other day (bi-daily). Administration can occur on one or more days.

Administration of the compositions and dosage forms can be combined with other regimens used for treatment of the condition. For example, the method of the present invention can be combined with diet regimens (e.g., low carbohydrate diets, high protein diets, high fiber diets, etc.), exercise regimens, weight loss regimens, smoking cessation regimens, or combinations thereof. The method of the present invention can also be used in combination with other pharmaceutical products in the treatment of the condition. The compositions or dosage forms of the present invention can be administered before or after other regimens or pharmaceutical products.

Kits Comprising the Compositions

The invention is directed to kits or packages containing one or more units of a composition of the invention. Kits or packages can include units of a food product, pharmaceutical composition, cosmetic, or industrial composition comprising the microorganism, biomass, or microbial oil of the invention, or combinations thereof. Kits or packages can also include an additive comprising the microorganism, biomass, or microbial oil of the invention, or combinations thereof for preparation of a food, cosmetic, pharmaceutical composition, or industrial composition.

In some embodiments, the kit or package contains one or more units of a pharmaceutical composition to be administered according to the methods of the present invention. The kit or package can contain one dosage unit, or more than one dosage unit (i.e., multiple dosage units). If multiple dosage units are present in the kit or package, the multiple dosage units can be optionally arranged for sequential administration.

The kits of the present invention can optionally contain instructions associated with the units or dosage forms of the kits. Such instructions can be in a form prescribed by a governmental agency regulating the manufacture, use or sale of pharmaceutical products, which notice reflects approval by the agency of the manufacture, use or sale for human administration to treat a condition or disorder. The instructions can be in any form which conveys information on the use of the units or dosage forms in the kit according to the methods of the invention. For example, the instructions can be in the form of printed matter, or in the form of a pre-recorded media device.

In the course of examination of a patient, a medical professional can determine that administration of one of the methods of the present invention is appropriate for the patient, or the physician can determine that the patient's condition can be improved by the administration of one of the methods of the present invention. Prior to prescribing any regimen, the physician can counsel the patient, for example, on the various risks and benefits associated with the regimen. The patient can be provided full disclosure of all known and suspected risks associated with the regimen. Such counseling can be provided verbally, as well as in written form. In some embodiments, the physician can provide the patient with literature materials on the regimen, such as product information, educational materials, and the like.

The present invention is directed to methods of educating consumers about the methods of treatment, the method comprising distributing the dosage forms with consumer information at a point of sale. In some embodiments, the distribution will occur at a point of sale having a pharmacist or healthcare provider.

The term "consumer information" can include, but is not limited to, an English language text, non-English language text, visual image, chart, telephone recording, website, and access to a live customer service representative. In some embodiments, consumer information will provide directions for use of the dosage forms according to the methods of the present invention, appropriate age use, indication, contraindications, appropriate dosing, warnings, telephone number or website address. In some embodiments, the method further comprises providing professional information to relevant persons in a position to answer consumer questions regarding use of the disclosed regimens according to the methods of the present invention. The term "professional information" includes, but is not limited to, information concerning the regimen when administered according to the methods of the present invention that is designed to enable a medical professional to answer customer questions.

A "medical professional," includes, for example, a physician, physician assistant, nurse, nurse practitioner, pharmacist and customer service representative.

Having generally described this invention, a further understanding can be obtained by reference to the examples provided herein. These examples are for purposes of illustration only and are not intended to be limiting.

EXAMPLE 1

Isolation of Microorganisms

Samples were collected from intertidal habitats during low tide, including bays and estuaries along the West Coast of North America (California, Oregon, and Washington) and Hawaii. Water, sediment, living plant material, and decaying plant/animal debris were placed into sterile 50 ml tubes. Portions of each sample along with the water were spread onto solid agar plates of isolation media. Isolation media consisted of: 500 ml of artificial seawater, 500 ml of distilled water, 1 g of glucose, 1 g of glycerol, 13 g of agar, 1 g of glutamate, 0.5 g of yeast extract, 0.5 g casein hydrolysate, 1 ml of a vitamin solution (100 mg/L thiamine, 0.5 mg/L biotin, 0.5 mg $B_{12}$), 1 ml of a trace mineral solution (PII metals, containing per liter: 6.0 g $FeCl_36H_2O$, 6.84 g $H_3BO_3$, 0.86 g $MnCl_24H_2O$, 0.06 g $ZnCl_2$, 0.026 $CoCl_26H_2O$, 0.052 g $NiSO_4H_2O$, 0.002 g $CuSO_45H_2O$ and 0.005 g $Na_2MoO_42H_2O$), and 500 mg each of penicillin G and streptomycin sulfate. The agar plates were incubated in the dark at 20-25° C. After 2-4 days the agar plates were examined under magnification, and colonies of cells were picked with a sterile toothpick and restreaked onto a fresh plate of media. Cells were repeatedly streaked onto fresh media until contaminated organisms were removed. Two of the isolated microorganisms were deposited under ATCC Accession Nos. PTA-10212 and PTA-10208.

Taxonomic Characteristics of the Isolated Microorganism Deposited Under ATCC Accession No. PTA-10212

Cultures of the isolated microorganism deposited under ATCC Accession No. PTA-10212 ("PTA-10212") appeared as white, wet, smeared colonies without visible isolated sori.

PTA-10212 was grown on solid and liquid FFM, solid KMV, KMV slush (1%), KMV broth, and MH broth to further examine growth characteristics. PTA-10212 was observed to grow rapidly on KMV and MH. See, e.g., Porter D., 1989. *Phylum Labyrinthulomycota*. In Margulis, L., Corliss, J. O., Melkonian, M., Chapman, D. J. (Eds.) Handbook of Protoctista, Jones and Bartlett, Boston, pp. 388-398 (KMV); Honda et al., *Mycol. Res.* 102:439-448 (1998) (MH); and U.S. Pat. No. 5,130,242 (FFM), each of which is incorporated herein by reference in its entirety.

The following observations were made after growth of PTA-10212 over several days on solid FFM media, after 72 hours growth in KMV medias, and MH broth. Sporangia were not clumped in/on any media and were very small (5-10 μm). PTA-10212 did not demonstrate the copious tetrads characteristic of *Schizochytrium* cleavage patterns. Amoeboid cells appeared about 24 hours after transfer to fresh solid media. These amoeboid cells were gone after a few days and were not evident in liquid or slush media. Unlike *Aurantiochytrium*, described by Yokoyama, R. et al., *Mycoscience* 48(6): 329-341 (2007), as having the appearance of "small sandgrains on the bottom of the flask" when grown in liquid media, PTA-10212 did not settle at the bottom of the flask but was suspended in both KMV and MH liquid media. The sporangia were not as dense as typical of *Schizochytrium* or *Oligochytrium*, which also have robust ectoplasmic networks that were absent from PTA-10212. While most species undergo vegetative cleavage of small sporangia or assimilative cells by the division of a larger sporangium over several hours, PTA-10212 formed dumbbell-shaped elongated assimilative cells, which then formed a thin isthmus that pulled apart as the ends of the dumbbell separated. The resulting cells appeared to be small assimilative cells. Direct transformation of an amoeboid cell into the dumbbell shaped assimilative cell was not observed. Typical biflagellate zoospores were observed swimming but were relatively rare. PTA-10212 was non-prolific, dividing by vegetative cleavage. Direct release of zoospores was not observed, although zoospores were observed swimming. Vegetative cells were very small (2 μm to 5 μm).

PTA-10212 was further examined using the flow-through technique, in which microscopic slides were prepared by suspending a small portion of an agar-grown colony in a drop of half-strength sea water. With this technique, primary sporangia were observed to be globose and approximately 10 μm in diameter. Walls were very thin and remnants were not observed when binary division of the protoplast was initiated. Repeated binary division produced 8-16 smaller (4-5 μm in diameter) secondary sporangia. The secondary sporangia remained quiescent for several hours before again releasing an amorphous protoplast. The amorphous protoplast divided by pinching and pulling, initially producing typical dumbbell-shaped intermediate stages and finally resulting in 4-8 small globose bodies 2.5-2.8 μm in diameter. The latter rested for several minutes up to 1-2 hours, then changed shape (elongated) and turned into biflagellate zoospores, 2.3-2.5×3.7-3.9 μm. Zoospores were abundant and could be precisely measured when they came to rest. Zoospores then rounded off and started a new cycle of development. The zoospores were larger than *Sicyoidochytrium minutum* and smaller than *Ulkenia visurgensis*.

PTA-10212 was further characterized based on the similarity of its 18s rRNA gene to that of known species. Genomic DNA was prepared from PTA-10212 by standard procedures. See, for example, Sambrook J. and Russell D. 2001. Molecular cloning: A laboratory manual, 3rd edition. Cold Spring Harbor Laboratory Press, Cold Spring Harbor, N.Y. Briefly: (1) 500 μL of cells were centrifuged from mid-log culture. The cells were re-centrifuged, and all traces of liquid were removed from the cell pellet with a small-bore tip; (2) pellets were resuspended with 200 μL lysis buffer (20 mM Tris pH 8.0, 125 μg/mL Proteinase K, 50 mM NaCl, 10 mM EDTA pH 8.0, 0.5% SDS); (3) cells were lysed at 50° C. for 1 hour; (4) the lysis mixture was pipetted into phase-lock gel (PLG-Eppendorf) 2 mL tubes; (5) equal volume of P:C:I was added and allowed to mix for 1.5 hours; (6) the tubes were centrifuged at 12,000×g for 5 minutes; (7) the aqueous phase was removed from above the gel within the PLG tube and an equal volume of chloroform was added to the aqueous phase, and mixed for 30 minutes; (8) the tubes were centrifuged at 14,000×g for approximately 5 minutes; (9) the top layer (aqueous phase) was pipetted away from the chloroform, and placed in a new tube; (10) 0.1 volume of 3 M NaOAC was added and mixed (inverted several times); (11) 2 volumes of 100% EtOH were added and mixed (inverted several times) with genomic DNA precipitant forming at this stage; (12) the tubes were centrifuged at 4° C. in a microcentrifuge at 14,000×g for approximately 15 minutes; (13) the liquid was gently poured off with genomic DNA remaining at the bottom of the tube; (14) the pellet was washed with 0.5 mL 70% EtOH; (15) the tubes were centrifuged at 4° C. in a microcentrifuge at 14,000×g for approximately 5 minutes; (16) the EtOH was gently poured off and the genomic DNA pellet was dried; and (17) a suitable volume of H₂O and RNase was added directly to the genomic DNA pellet. The PCR amplification of the 18s rRNA gene was carried out with primers previously described (Honda et. al., *J. Euk. Micro.* 46(6): 637-647 (1999). The PCR conditions with chromosomal DNA template were as follows: 0.2 μM dNTPs, 0.1 μM each primer, 8% DMSO, 200 ng chromosomal DNA, 2.5 U Herculase® II Fusion DNA Polymerase (Stratagene), and Herculase® buffer (Stratagene) in a 50 μL total volume. The PCR Protocol included the following steps: (1) 95° C. for 2 minutes; (2) 95° C. for 35 seconds; (3) 55° C. for 35 seconds; (4) 72° C. for 1 minute and 30 seconds; (5) repeat steps 2-4 for 30 cycles; (6) 72° C. for 5 minutes; and (7) hold at 4° C.

PCR amplification yielded a distinct DNA product with the expected size using chromosomal template described above. The PCR product was cloned into the vector pJET1.2/blunt (Fermentas) according to the manufacturer's instructions, and the insert sequence was determined using supplied standard primers.

Phylogenetic analysis places PTA-10212 within the lineage that includes *Thraustochytrium pachydermum* and *Thraustochytrium aggregatum* with moderate support. The sporangia of *T. pachydermum* have very thick cell walls. *T. aggregatum* forms clearly visible clumps of sori that are opaque. PTA-10212 shows neither of these characteristics. The presence of many amoeboid cells has been described in other taxa, such as *Ulkenia, T. gaertnerium, A. limiacinum*, and *S. mangrovei*; however, the descriptions associated with those taxa differ from the observed characteristics of the isolate. Moreover, PTA-10212 did not show phylogenetic affinity towards any of these taxa.

Table 3 shows a comparison of the 18s rRNA sequence from the microorganism deposited under ATCC Accession No. PTA-10212 to DNA sequences in the National Center for Biotechnology Information (NCBI) electronic database. The percent identity was determined using two different calculations. "Calculation #1" takes into consideration any "gaps" that occur in the sequences, either from non-homologous regions or partial sequence (AlignX-VectorNTI default settings). "Calculation #2" does not include calculated penalties for gaps (AlignX-VectorNTI "IDENTITY" matrix setting).

TABLE 3

Comparison of 18s rRNA Sequences

| Thraustochytrids | % Identity Calculation #1 | % Identity Calculation #2 |
| --- | --- | --- |
| Thraustochytrium pachydermum | 85% | 93% |
| Thraustochytrium aggregatum (p) | 83% | 92% |
| Thraustochytrium gaertnerium | 82% | 92% |
| Ulkenia visurgensis | 82% | 92% |
| Schizochytrium sp. PTA-9695 | 80% | 92% |
| Schizochytrium mangrovei | 80% | 91% |
| Schizochytrium sp. ATCC 20888 | 80% | 90% |
| Aurantiochytrium limiacinum | 79% | 90% |

(p): indicates partial sequence

As shown in Table 3, it was found that, in terms of % identity, the 18s rRNA gene sequence (SEQ ID NO:1) from the microorganism deposited under ATCC Accession No. PTA-10212 is related, though not identical, to 18s rRNA gene sequences available in the NCBI database. It is generally recognized that organisms can have closely related 18s rRNA gene sequences while belonging to a different genus or species.

Based on the above characterization, the isolated microorganism deposited under ATCC Accession No. PTA-10212 is believed to represent a new *Thraustochytrium* species and is therefore also designated as *Thraustochytrium* sp. ATCC PTA-10212.

Taxonomic Characteristics of the Isolated Microorganism Deposited Under ATCC Accession No. PTA-10208

The microorganism deposited under ATCC Accession No. PTA-10208 ("PTA-10208") was identified as a sub-isolate (an individual cell isolated from a culture and maintained as a new separate and distinct culture) of the microorganism deposited under ATCC Accession No. PTA-9695 ("PTA-9695"), described in U.S. application Ser. No. 12/407,687 and PCT/US2009/001720, each of which is incorporated herein by reference in its entirety.

PTA-10208 shares taxonomic characteristics with PTA-9695. PTA-9695 was found to have biflagellate zoospores at discharge that swim actively away from the mature sporangium, wall remnants of which were clearly visible (in phase contrast) after spore release. PTA-9695 sporangia measured 12.5 µm to 25 µm in diameter, and zoospores were 2.5 µm to 2.8 µm×4.5 µm to 4.8 µm in size. There were 8 to 24 spores per individual PTA-9695 sporangium. Settled PTA-9695 zoospores enlarged and rapidly underwent binary divisions leading to tetrads, octads, and finally to clusters of sporangia. Tetrad formation commenced at a very early stage prior to maturity of the sporangia. These characteristics are in agreement with the genus *Schizochytrium*. In terms of % identity, the PTA-9695 18s rRNA gene sequence (SEQ ID NO:2), which is shared by PTA-10208, was found to be closely related, though not identical, to the 18s rRNA gene sequence of *T. aggregatum* provided in Honda, D. et al., *J. Euk. Micro.* 46(6): 637-647 (1999). The 18s rRNA sequence published for *Thraustochytrium aggregatum* is a partial sequence, with an approximately 71 DNA nucleotide gap in the middle of the sequence. PTA-9695 is believed to represent a new *Schizochytrium* species. As such, the sub-isolate PTA-10208 is also designated as *Schizochytrium* sp. ATCC PTA-10208.

EXAMPLE 2

Growth Characteristics of the Isolated Microorganism Deposited Under ATCC Accession No. PTA-10212

The isolated microorganism deposited under ATCC Accession No. PTA-10212 was examined for growth characteristics in individual fermentation runs, as described below. Typical media and cultivation conditions are shown in Table 1.

In carbon (glycerol) and nitrogen-fed cultures with 1000 ppm at 22.5° C. with 20% dissolved oxygen at pH 7.3, PTA-10212 produced a dry cell weight of 26.2 g/L after 138 hours of culture in a 10 L fermentor volume. The lipid yield was 7.9 g/L; the omega-3 yield was 5.3 g/L; the EPA yield was 3.3 g/L; and the DHA yield was 1.8 g/L. The fatty acid content was 30.3% by weight; the EPA content was 41.4% of fatty acid methyl esters (FAME); and the DHA content was 26.2% of FAME. The lipid productivity was 1.38 g/L/day, and the omega-3 productivity was 0.92 g/L/day under these conditions, with 0.57 g/L/day EPA productivity and 0.31 g/L/day DHA productivity.

In carbon (glycerol) and nitrogen-fed cultures with 1000 ppm at 22.5° C. with 20% dissolved oxygen at pH 7.3, PTA-10212 produced a dry cell weight of 38.4 g/L after 189 hours of culture in a 10 L fermentor volume. The lipid yield was 18 g/L; the omega-3 yield was 12 g/L; the EPA yield was 5 g/L; and the DHA yield was 6.8 g/L. The fatty acid content was 45% by weight; the EPA content was 27.8% of FAME; and the DHA content was 37.9% of FAME. The lipid productivity was 2.3 g/L/day, and the omega-3 productivity was 1.5 g/L/day under these conditions, with 0.63 g/L/day EPA productivity and 0.86 g/L/day DHA productivity.

In carbon (glycerol) and nitrogen-fed cultures with 1000 ppm at 22.5° C. with 20% dissolved oxygen at pH 6.8-7.7, PTA-10212 produced a dry cell weight of 13 g/L after 189 hours of culture in a 10 L fermentor volume. The lipid yield was 5.6 g/L; the omega-3 yield was 3.5 g/L; the EPA yield was 1.55 g/L; and the DHA yield was 1.9 g/L. The fatty acid content was 38% by weight; the EPA content was 29.5% of FAME; and the DHA content was 36% of FAME. The lipid productivity was 0.67 g/L/day, and the omega-3 productivity was 0.4 g/L/day under these conditions, with 0.20 g/L/day EPA productivity and 0.24 g/L/day DHA productivity.

In carbon (glycerol) and nitrogen-fed cultures with 1000 ppm at 22.5-28.5° C. with 20% dissolved oxygen at pH 6.6-7.2, PTA-10212 produced a dry cell weight of 36.7 g/L-48.7 g/L after 191 hours of culture in a 10 L fermentor volume. The lipid yield was 15.2 g/L-25.3 g/L; the omega-3 yield was 9.3 g/L-13.8 g/L; the EPA yield was 2.5 g/L-3.3 g/L; and the DHA yield was 5.8 g/L-11 g/L. The fatty acid content was 42.4%-53% by weight; the EPA content was 9.8%-22% of FAME; and the DHA content was 38.1%-43.6% of FAME. The lipid productivity was 1.9 g/L/day-3.2 g/L/day, and the omega-3 productivity was 1.2 g/L/day-1.7 g/L/day under these conditions, with 0.31 g/L/day-0.41 g/L/day EPA productivity and 0.72 g/L/day-1.4 g/L/day DHA productivity.

Growth Characteristics of the Isolated Microorganism Deposited Under ATCC Accession No. PTA-10208

The isolated microorganism deposited under ATCC Accession No. PTA-10208 was examined for growth characteristics in individual fermentation runs, as described below. Typical media and cultivation conditions are shown in Table 2.

In carbon (glucose) and nitrogen-fed cultures with 1000 ppm Cl$^-$ at 22.5° C. at pH 7.0 with 20% dissolved oxygen during the nitrogen feed and 10% dissolved oxygen thereafter, PTA-10208 produced a dry cell weight of 95 g/L after 200 hours of culture in a 10 L fermentor volume. The lipid yield was 53.7 g/L; the omega-3 yield was 37 g/L; the EPA yield was 14.3 g/L; and the DHA yield was 21 g/L. The fatty acid content was 57% by weight; the EPA content was 27.7% of FAME; and the DHA content was 39.1% of FAME. The lipid productivity was 6.4 g/L/day, and the omega-3 productivity was 4.4 g/L/day under these conditions, with 1.7 g/L/day EPA productivity and 2.5 g/L/day DHA productivity.

In carbon (glucose) and nitrogen-fed cultures with 1000 ppm Cl$^-$ at 22.5° C. at pH 7.5 with 20% dissolved oxygen during the nitrogen feed and 10% dissolved oxygen thereafter, PTA-10208 produced a dry cell weight of 56 g/L after 139 hours of culture in a 10 L fermentor volume. The lipid yield was 53 g/L; the omega-3 yield was 34 g/L; the EPA yield was 11.5 g/L; and the DHA yield was 22 g/L. The fatty acid content was 58% by weight; the EPA content was 21.7% of FAME; and the DHA content was 41.7% of FAME. The lipid productivity was 9.2 g/L/day, and the omega-3 productivity was 5.9 g/L/day under these conditions, with 2 g/L/day EPA productivity and 3.8 g/L/day DHA productivity.

In carbon (glucose) and nitrogen-fed cultures with 1000 ppm Cl$^-$ at 22.5° C. at pH 7.0 with 20% dissolved oxygen during the nitrogen feed and 10% dissolved oxygen thereafter, PTA-10208 produced a dry cell weight of 93.8 g/L after 167 hours of culture in a 2000 L fermentor volume. The lipid yield was 47.2 g/L; the omega-3 yield was 33.1 g/L; the EPA yield was 10.5 g/L; and the DHA yield was 20.4 g/L. The fatty acid content was 50.6% by weight; the EPA content was 23% of FAME; and the DHA content was 42.6% of FAME. The lipid productivity was 6.8 g/L/day, and the omega-3 productivity was 4.7 g/L/day under these conditions, with 1.5 g/L/day EPA productivity and 2.9 g/L/day DHA productivity.

In carbon (glucose) and nitrogen-fed cultures with 1000 ppm Cl$^-$ at 22.5° C. at pH 7.0 with 20% dissolved oxygen during the nitrogen feed and 10% dissolved oxygen thereafter, PTA-10208 produced a dry cell weight of 105 g/L after 168 hours of culture in a 2000 L fermentor volume. The lipid yield was 46.4 g/L; the omega-3 yield was 33 g/L; the EPA yield was 10.7 g/L; and the DHA yield was 20.3 g/L. The fatty acid content was 43.9% by weight; the EPA content was 24% of FAME; and the DHA content was 43.7% of FAME. The lipid productivity was 6.6 g/L/day, and the omega-3 productivity was 4.7 g/L/day under these conditions, with 1.5 g/L/day EPA productivity and 2.9 g/L/day DHA productivity.

In carbon (glucose) and nitrogen-fed cultures with 1000 ppm Cl⁻ at 22.5° C. at pH 7.0 with 20% dissolved oxygen during the nitrogen feed and 10% dissolved oxygen thereafter, PTA-10208 produced a dry cell weight of 64.8 g/L after 168 hours of culture in a 2000 L fermentor volume. The lipid yield was 38.7 g/L; the omega-3 yield was 29.9 g/L; the EPA yield was 8.5 g/L; and the DHA yield was 16.7 g/L. The fatty acid content was 59.6% by weight; the EPA content was 23% of FAME; and the DHA content was 42.3% of FAME. The lipid productivity was 5.53 g/L/day, and the omega-3 productivity was 3.8 g/L/day under these conditions, with 1.2 g/L/day EPA productivity and 2.3 g/L/day DHA productivity.

EXAMPLE 3

Fatty Acid Profiles of Microorganism Strains ATCC PTA-10208 and PTA-10212

Four samples of biomass (PTA-10208 Sample #1; PTA-10208 Sample #2; PTA-10212 Sample #1; and PTA-10212 Sample #2) were analyzed for total crude oil content by solvent extraction, lipid classes were determined by high performance liquid chromatography/evaporative light scattering detection (HPLC/ELSD), triacylglycerol (TAG) were analyzed by HPLC/mass spectrometry (HPLC/MS), and fatty acid (FA) profiles were determined by gas chromatography with flame ionization detection (GC-FID). The crude lipid content of each freeze dried biomass was determined using solvent grinding with hexane and compared to the sum of FAME (mg/g) generated by direct transesterification, and the resultant fatty acid methyl esters (FAME) were quantified by GC/FID analysis. Fatty acids in the extracted crude lipid were also quantified by transesterification and quantified using GC/FID analysis of the resultant FAME. The weight percent of all neutral lipids (NL) and free fatty acids (FFA) were determined in the extracted crude lipid using normal phase HPLC with ELSD and atmospheric pressure chemical ionization-MS (APCI-MS) identification. The method separates and quantifies sterol esters (SE), TAG, free fatty acids (FFA), 1,3-diacylglycerols (1,3-DAG), sterols, 1,2-diacylglycerols (1,2-DAG), and monoacylglycerols (MAG). Results are shown in Tables 4 and 5, below.

TAG and phospholipids (PL) were isolated from the crude oils extracted from the four samples of biomass (PTA-10208 Sample #1; PTA-10208 Sample #2; PTA-10212 Sample #1; and PTA-10212 Sample #2). TAG was isolated using low pressure flash chromatography and PL was isolated using solid phase extraction (SPE). The identity of each isolated fraction was confirmed by thin layer chromatography (TLC). The fatty acid profiles of the isolated TAG and PL fractions were determined following direct transesterification using GC-FID as FAME. Results are shown in Tables 6 and 7, below.

The total crude oil content and fatty acid profiles of isolated lipid classes were also determined for two additional samples of biomass from microorganism strain ATCC PTA-10212 (PTA-10212 Sample #3 and PTA-10212 Sample #4). Crude oil was obtained from each sample by hexane extraction, and individual lipid classes were isolated using low pressure flash chromatography. The fatty acid profiles of the biomass, crude oil, and isolated fractions were determined using GC-FID as FAME. Results are shown in Tables 8-11, below.

Individual lipid classes were isolated from a sample of crude oil from microorganism strain ATCC PTA-10212 (PTA-10212 Sample #5) previously extracted using the FRIOLEX® process, and the fatty acid profiles of each class were determined using GC-FID as FAME. Results are shown in Tables 12 and 13, below.

Individual lipid classes were isolated from a sample of crude oil from microorganism strain ATCC PTA-10208 (PTA-10208 Sample #3) using normal HPLC with ELSD and APCI-MS identification.

Experimental Procedures

Crude Oil Extraction—

Crude oil was extracted from samples of freeze-dried biomass using solvent grinding. For example, approximately 3 grams of biomass was weighed into a Swedish tube. Three ball bearings and 30 mL of hexane were added to the Swedish tube, which was sealed with a neoprene stopper and placed in a shaker for 2 hours. The resultant slurry was filtered using a Buchner funnel and Whatman filter paper. The filtered liquid was collected, the solvent removed under vacuum, and the amount of remaining crude lipid determined gravimetrically.

Fatty Acid Analysis—

The samples of biomass, extracted crude lipid, and isolated lipid classes were analyzed for fatty acid composition as FAME. Briefly, freeze-dried biomass and isolated lipid classes were weighed directly into a screw cap test tubes, while samples of the crude oil were dissolved in hexane to give a concentration of approximately 2 mg/mL. Toluene, containing internal standard, and 1.5 N HCl in methanol was added to each tube. The tubes were vortexed, then capped and heated to 100° C. for 2 hours. The tubes were allowed to cool, and saturated NaCl in water was added. The tubes were vortexed again and centrifuged to allow the layers to separate. A portion of the organic layer was then placed in a GC vial and analyzed by GC-FID. FAME was quantified using a 3-point calibration curve generated using Nu-Check-Prep GLC Reference Standard (NuCheck, Elysian, Minn.). Fatty acids present in the extract were expressed as mg/g and as a weight percent. Fat content in the samples was estimated assuming equal response to the internal standard when analyzed by GC-FID.

| HPLC/ELSD/MS Method - | | | |
|---|---|---|---|
| Instrument | Agilent 1100 HPLC, Alltech 3300 ELSD, Agilent 1100 MSD | | |
| Column | Phenomenex Luna Silica, 250 × 4.6 mm, 5 μm particle size w/ Guard Column | | |
| Mobile Phase | A - 99.5% Hexanes (Omnisolv) 0.4% Isopropyl alcohol (Omnisolv) 0.1% Acetic Acid B - 99.9% Ethanol (Omnisolv, 95:5 Ethanol:IPA) 0.1% Acetic Acid | | |
| | Time, min. | % A | % B |
| Gradient | 0 | 100 | 0 |
| | 5 | 100 | 0 |
| | 15 | 85 | 10 |
| | 20 | 0 | 100 |

| HPLC/ELSD/MS Method - | | |
|---|---|---|
| 25 | 0 | 100 |
| 26 | 100 | 0 |
| 35 | 100 | 0 |

| | |
|---|---|
| Column Temp. | 30° C. |
| Flow Rate | 1.5 mL/min |
| Injection Volume | 5 µL |
| ELSD Detection | Temperature 35° C., Gas flow 1.2 L/min |
| MSD | Mass Range 200-1200, Fragmentor 225 V |
| | Drying Gas Temperature 350° C. |
| | Vaporizer Temperature 325° C. |
| | Capillary Voltage 3500 V |
| | Corona Current 10 µA |

Solid Phase Extraction—

PL fractions were separated from the crude lipid by solid phase extraction (SPE) using 2 g aminopropyl cartridges (Biotage, Uppsala, Sweden) placed in a Vac Elut apparatus (Varian Inc, Palo Alto, USA). The cartridge was conditioned with 15 mL of hexane, and ~60 mg of each sample was dissolved in 1 mL CHCl$_3$ and applied to the cartridge. The column was washed with 15 mL of 2:1 CHCl$_3$:isopropyl alcohol to elute all the neutral lipids, which was discarded. The fatty acids were then eluted with 15 mL of 2% acetic acid (HOAc) in ether, which was discarded. The PL portion was eluted with 15 mL of 6:1 Methanol:Chloroform, which was collected, dried under nitrogen, and weighed.

Flash Chromatography—

Flash chromatography was used to separate the lipid classes present in the crude oil. Approximately 200 mg of crude oil dissolved in hexane was injected onto the head of the column. The chromatography system utilized Silica Gel 60 (EMD Chemical, Gibbstown, N.J.) with mobile phase composed of Petroleum Ether and Ethyl Acetate at 5 mL/min (Tables 6-7) or 3 mL/min (Tables 8-13). A step gradient was used to selectively elute each lipid class from the column. The mobile phase gradient started from 100% petroleum ether and finished with 50% ethyl acetate. Fractions were collected in 10 mL test tubes using a Gilson FC 204 large-bed fraction collector (Gilson, Inc., Middleton, Wis.). Each tube was analyzed by thin layer chromatography (TLC) and the tubes containing individual lipid classes (as judged by single spots on TLC plate with expected retention factor (Rf)) were pooled, concentrated to dryness, and weighed. The total fraction content was then determined gravimetrically.

TLC Analysis—

Thin layer chromatography was conducted on silica gel plates.

The plates were eluted using a solvent system consisting of petroleum ether: ethyl ether: acetic acid (80:20:1) and were visualized using iodine vapor. The Rf values of each spot were then compared with reported literature values for each lipid class.

Analysis of TAG and PL Fractions—

The isolated TAG and PL fractions were analyzed for fatty acid composition as fatty acid methyl esters (FAME). The TAG fractions were dissolved in hexane to give a concentration of approximately 1-2 mg/mL. 1 mL aliquots of the solutions were concentrated to dryness under nitrogen. Toluene, containing internal standard, and 1.5 N HCl in methanol was added to each tube. The tubes were vortexed, then capped and heated to 100° C. for 2 hours. Internal standard and HCl methanol were added directly to the tubes containing the PL fraction and heated. The tubes were allowed to cool, and saturated NaCl in water was added. The tubes were vortexed again and centrifuged to allow the layers to separate. A portion of the organic layer was then placed in a GC vial and analyzed by GC-FID. FAMEs were quantified using a 3-point calibration curve generated using Nu-Check-Prep GLC 502B Reference Standard (NuCheck, Elysian, Minn.). Fatty acids present in the extract were expressed as mg/g and as a % of FAME.

Results

PTA-10208 Sample #1

The fatty acid profile of the biomass and extracted crude lipid for PTA-10208 Sample #1 was determined using GC/FID. Fatty acids in the biomass were transesterified in situ by weighing 28.6 mg of biomass directly into a FAME tube, while a sample of the extracted crude lipid was prepared by weighing 55.0 mg of crude lipid into a 50 mL volumetric flask and transferring 1 ml to a separate FAME tube. The estimated crude lipid content of the biomass was determined to be 53.2% (as SUM of FAME) using GC with FID detection, while 52.0% (wt/wt) lipid was extracted from the dry biomass, giving a 97.8% recovery of total lipid. The crude lipid was determined to be 91.9% fatty acids (as SUM of FAME) using GC/FID. The major fatty acids contained in the crude lipid were C16:0 (182.5 mg/g), C20:5 n-3 (186.8 mg/g), and C22:6 n-3 (423.1 mg/g).

The lipid class profile of the extracted crude lipid was determined by weighing 55.0 mg of crude lipid into a 50 mL volumetric flask and transferring an aliquot into an HPLC vial for HPLC/ELSD/MS analysis. According to the HPLC/ELSD/MS analysis, the crude lipid contained 0.2% sterol esters (SE), 95.1% TAG, 0.4% sterols, and 0.5% 1,2-diacylglycerol (DAG). 5% of the TAG fraction included a peak that eluted directly after the TAG peak, but did not give a recognizable mass spectrum.

Isolated TAG from this sample as determined by flash chromatography made up approximately 92.4% of the crude oil. PL was not detected by weight or TLC after SPE isolation. The major fatty acids (>50 mg/g) contained in the TAG were C16:0 (189 mg/g), C20:5 n-3 (197 mg/g), and C22:6 n-3 (441 mg/g).

PTA-10208 Sample #2

The fatty acid profile of the biomass and extracted crude lipid for PTA-10208 Sample #2 was determined using GC/FID. Fatty acids in the biomass were transesterified in situ by weighing 32.0 mg of biomass directly into a FAME tube, while a sample of the extracted crude lipid was prepared by weighing 60.1 mg of crude lipid into a 50 mL volumetric flask and transferring 1 ml to a separate FAME tube. The estimated crude lipid content of the biomass was determined to be 52.4% (as SUM of FAME) using GC with FID detection, while 48.0% (wt/wt) lipid was extracted from the dry biomass, giving a 91.7% recovery of total lipid. The crude lipid was determined to be 95.3% fatty acids (as SUM of FAME) using GC/FID. The major fatty acids contained in the crude lipid were C16:0 (217.5 mg/g), C20:5 n-3 (169.3 mg/g), and C22:6 n-3 (444.1 mg/g).

The lipid class profile of the extracted crude lipid was determined by weighing 60.1 mg of crude lipid into a 50 mL volumetric flask and transferring an aliquot into an HPLC vial for HPLC/ELSD/MS analysis. According to the HPLC/ELSD/MS analysis, the crude lipid contained 0.2% SE, 95.7% TAG, 0.3% sterols, and 0.7% 1,2-DAG. 5.1% of the TAG fraction included a peak that eluted directly after the TAG peak, but did not give a recognizable mass spectrum.

Isolated TAG from this sample made up approximately 93.9% of the crude oil. PL was not detected by weight or TLC after SPE isolation. The major fatty acids (>50 mg/g)

contained in the TAG were C16:0 (218 mg/g), C20:5 n-3 (167 mg/g) and C22:6 n-3 (430 mg/g).

PTA-10208 Sample #3

A sample of crude oil from the microorganism deposited under ATCC Accession No. PTA-10208 (Sample PTA-10208 #3) was analyzed using HPLC/ELSD/MS. A total of 98.38% of lipids were recovered, with the sterol ester (SE) fraction accounting for 0.32%, the TAG fraction accounting for 96.13%, the 1,3-diacylglycerol (DAG) fraction accounting for 0.22%, the 1,2-DAG fraction accounting for 0.78%, and the sterol fraction accounting for 0.93%.

PTA-10212 Sample #1

The fatty acid profile of the biomass and extracted crude lipid for PTA-10212 Sample #1 was determined using GC/FID. Fatty acids in the biomass were transesterified in situ by weighing 27.0 mg of biomass directly into a FAME tube, while a sample of the extracted crude lipid was prepared by weighing 52.5 mg of crude lipid into a 50 mL volumetric flask and transferring 1 ml to a separate FAME tube. The estimated crude lipid content of the biomass was determined to be 38.3% (as SUM of FAME) using GC with FID detection, while 36.3% (wt/wt) lipid was extracted from the dry biomass, giving a 94.6% recovery of total lipid. The crude lipid was determined to be 83.2% fatty acids (as SUM of FAME) using GC/FID. The major fatty acids contained in the crude lipid were C16:0 (328.5 mg/g), C20:5 n-3 (90.08 mg/g), and C22:6 n-3 (289.3 mg/g).

The lipid class profile of the extracted crude lipid was determined by weighing 52.5 mg of crude lipid into a 50 mL volumetric flask and transferring an aliquot into an HPLC vial for HPLC/ELSD/MS analysis. According to the HPLC/ELSD/MS analysis, the crude lipid contained 0.2% SE, 64.2% TAG, 1.9% FFA, 2.8% 1,3-DAG, 1.4% sterols, 18.8% 1,2-DAG, and 0.5% MAG. 3.4% of the TAG fraction included a peak that eluted directly after the TAG peak, but did not give a recognizable mass spectrum.

Isolated TAG from this sample made up approximately 49.8% of the crude oil. Isolated PL made up approximately 8.1% of the crude oil. The major fatty acids (>50 mg/g) contained in the TAG fraction are C16:0 (400 mg/g), C20:5 n-3 (91 mg/g), and C22:6 n-3 (273 mg/g). The major fatty acids (>50 mg/g) contained in the PL fraction are C16:0 (98 mg/g), C20:5 n-3 (33 mg/g), and C22:6 n-3 (227 mg/g).

PTA-10212 Sample #2

The fatty acid profile of the biomass and extracted crude lipid PTA-10212 Sample #2 was determined using GC/FID. Fatty acids in the biomass were transesterified in situ by weighing 29.5 mg of biomass directly into a FAME tube, while a sample of the extracted crude lipid was prepared by weighing 56.5 mg of crude lipid into a 50 mL volumetric flask and transferring 1 ml to a separate FAME tube. The estimated crude lipid content of the biomass was determined to be 40.0% (as SUM of FAME) using GC with FID detection, while 41.3% (wt/wt) lipid was extracted from the dry biomass, giving a 106.1% recovery of total lipid. The crude lipid was determined to be 82.8% fatty acids (as SUM of FAME) using GC/FID. The major fatty acids contained in the crude lipid were C16:0 (327.3 mg/g), C20:5 n-3 (92.5 mg/g), and C22:6 n-3 (277.6 mg/g).

The lipid class profile of the extracted crude lipid was determined by weighing 56.5 mg of crude lipid into a 50 mL volumetric flask and transferring an aliquot into an HPLC vial for HPLC/ELSD/MS analysis. According to the HPLC/ELSD/MS analysis, the crude lipid contained 0.2% SE, 58.2% TAG, 2.3% FFA, 3.4% 1,3-DAG, 1.7% sterols, 23.4% 1,2-DAG, and 0.6% MAG. 3.3% of the TAG fraction included a peak that eluted directly after the TAG peak, but did not give a recognizable mass spectrum.

Isolated TAG from this sample made up approximately 51.9% of the crude oil. Isolated PL made up approximately 8.8% of the crude oil. The major fatty acids (>50 mg/g) contained in the TAG fraction are C16:0 (402 mg/g), C20:5 n-3 (92 mg/g), and C22:6 n-3 (245 mg/g). The major fatty acids (>50 mg/g) contained in the PL fraction are C16:0 (121 mg/g), C20:5 n-3 (48 mg/g), and C22:6 n-3 (246 mg/g).

TABLE 4

Fatty Acid Profiles of PTA-10208 and PTA-10212 Biomasses and Extracted Crude Lipids (mg/g)

| Fatty Acid | PTA-10208 Sample #1 Biomass FAME (mg/g) | PTA-10208 Sample #1 Crude Lipid FAME (mg/g) | PTA-10208 Sample #2 Biomass FAME (mg/g) | PTA-10208 Sample #2 Crude Lipid FAME (mg/g) | PTA-10212 Sample #1 Biomass FAME (mg/g) | PTA-10212 Sample #1 Crude Lipid FAME (mg/g) | PTA-10212 Sample #2 Biomass FAME (mg/g) | PTA-10212 Sample #2 Crude Lipid FAME (mg/g) |
|---|---|---|---|---|---|---|---|---|
| C12:0 | 1.47 | 2.43 | 1.80 | 3.14 | 0.99 | 1.90 | 0.87 | 1.91 |
| C14:0 | 11.62 | 20.12 | 16.72 | 31.03 | 5.51 | 12.91 | 5.97 | 13.69 |
| C14:1 | 0.00 | 0.00 | 0.00 | 0.00 | 0.00 | 0.00 | 0.00 | 0.00 |
| C15:0 | 2.43 | 3.75 | 3.60 | 6.22 | 9.13 | 20.42 | 9.39 | 20.81 |
| C16:0 | 105.04 | 182.47 | 117.72 | 217.49 | 145.87 | 328.45 | 147.87 | 327.27 |
| C16:1 | 0.00 | 0.00 | 0.06 | 0.01 | 6.26 | 14.53 | 7.46 | 16.89 |
| C18:0 | 5.37 | 8.96 | 4.77 | 8.37 | 6.77 | 15.39 | 6.77 | 15.15 |
| C18:1 n-9 | 0.00 | 3.26 | 0.00 | 3.09 | 0.03 | 4.04 | 0.08 | 5.87 |
| C18:1 n-7 | 0.00 | 0.00 | 0.00 | 0.00 | 0.00 | 0.00 | 0.00 | 0.00 |
| C18:2 n-6 | 0.00 | 0.00 | 0.00 | 0.00 | 0.00 | 0.00 | 0.00 | 0.00 |
| C20:0 | 1.48 | 1.79 | 1.40 | 1.85 | 1.60 | 3.09 | 1.67 | 3.20 |
| C18:3 n-3 | 0.00 | 0.00 | 0.00 | 0.00 | 0.00 | 0.00 | 0.00 | 0.00 |
| C20:1 n-9 | 0.00 | 0.00 | 0.00 | 0.00 | 0.00 | 0.00 | 0.00 | 0.00 |
| C18:4 n-3 | 0.91 | 1.61 | 1.10 | 2.00 | 2.28 | 2.56 | 2.21 | 2.64 |

TABLE 4-continued

Fatty Acid Profiles of PTA-10208 and PTA-10212 Biomasses and Extracted Crude Lipids (mg/g)

| Fatty Acid | PTA-10208 Sample #1 Biomass FAME (mg/g) | PTA-10208 Sample #1 Crude Lipid FAME (mg/g) | PTA-10208 Sample #2 Biomass FAME (mg/g) | PTA-10208 Sample #2 Crude Lipid FAME (mg/g) | PTA-10212 Sample #1 Biomass FAME (mg/g) | PTA-10212 Sample #1 Crude Lipid FAME (mg/g) | PTA-10212 Sample #2 Biomass FAME (mg/g) | PTA-10212 Sample #2 Crude Lipid FAME (mg/g) |
|---|---|---|---|---|---|---|---|---|
| C20:2 n-6 | 0.00 | 0.00 | 0.00 | 0.00 | 0.00 | 0.00 | 0.00 | 0.00 |
| C20:3 n-6 | 0.00 | 0.00 | 0.00 | 0.00 | 0.00 | 0.00 | 0.00 | 0.00 |
| C22:0 | 0.10 | 0.00 | 0.08 | 0.00 | 0.30 | 0.12 | 0.35 | 0.24 |
| C20:4 n-7 | 0.81 | 0.45 | 0.67 | 0.41 | 0.00 | 0.00 | 0.00 | 0.00 |
| C20:4 n-6 | 7.22 | 12.23 | 6.84 | 12.18 | 1.19 | 2.26 | 1.31 | 2.32 |
| C22:1 n-9 | 0.00 | 0.00 | 0.00 | 0.00 | 0.00 | 0.00 | 0.00 | 0.00 |
| C20:4 n-5 | 0.63 | 0.52 | 0.00 | 0.46 | 0.00 | 0.00 | 0.00 | 0.00 |
| C20:4 n-3 | 3.45 | 5.45 | 3.33 | 5.58 | 0.00 | 2.40 | 0.00 | 2.34 |
| C20:3 n-3 | 0.09 | 0.00 | 0.11 | 0.00 | 0.00 | 0.00 | 0.00 | 0.00 |
| C20:5 n-3 | 107.31 | 186.83 | 92.99 | 169.32 | 40.32 | 90.08 | 43.15 | 92.54 |
| C22:4 n-9 | 0.00 | 0.00 | 0.00 | 0.00 | 0.00 | 0.00 | 0.00 | 0.00 |
| C24:0 | 0.60 | 0.00 | 0.52 | 0.00 | 2.81 | 6.83 | 2.74 | 6.53 |
| C24:1 n-9 | 1.55 | 3.26 | 0.85 | 2.04 | 0.43 | 1.34 | 0.42 | 1.24 |
| C22:5 n-6 | 9.66 | 15.84 | 10.27 | 17.98 | 2.42 | 4.68 | 2.32 | 4.21 |
| C22:5 n-3 | 20.44 | 35.13 | 9.92 | 17.50 | 2.41 | 4.94 | 2.69 | 5.23 |
| C22:6 n-3 | 246.98 | 423.10 | 245.96 | 444.08 | 139.58 | 289.34 | 137.35 | 277.57 |
| Sum of FAME | 527.15 | 907.18 | 518.71 | 942.75 | 367.89 | 805.29 | 372.63 | 799.68 |

TABLE 5

Fatty Acid Profiles of PTA-10208 and PTA-10212 Biomasses and Extracted Crude Lipids (%)

| Fatty Acid | PTA-10208 Sample #1 Biomass % FAME | PTA-10208 Sample #1 Crude Lipid % FAME | PTA-10208 Sample #2 Biomass % FAME | PTA-10208 Sample #2 Crude Lipid % FAME | PTA-10212 Sample #1 Biomass % FAME | PTA-10212 Sample #1 Crude Lipid % FAME | PTA-10212 Sample #2 Biomass % FAME | PTA-10212 Sample #2 Crude Lipid % FAME |
|---|---|---|---|---|---|---|---|---|
| C12:0 | 0.28 | 0.27 | 0.35 | 0.33 | 0.27 | 0.24 | 0.23 | 0.24 |
| C14:0 | 2.20 | 2.22 | 3.22 | 3.29 | 1.50 | 1.60 | 1.60 | 1.71 |
| C14:1 | 0.00 | 0.00 | 0.00 | 0.00 | 0.00 | 0.00 | 0.00 | 0.00 |
| C15:0 | 0.46 | 0.41 | 0.69 | 0.66 | 2.48 | 2.54 | 2.52 | 2.60 |
| C16:0 | 19.93 | 20.11 | 22.70 | 23.07 | 39.65 | 40.79 | 39.68 | 40.93 |
| C16:1 | 0.00 | 0.00 | 0.01 | 0.00 | 1.70 | 1.80 | 2.00 | 2.11 |
| C18:0 | 1.02 | 0.99 | 0.92 | 0.89 | 1.84 | 1.91 | 1.82 | 1.89 |
| C18:1 n-9 | 0.00 | 0.36 | 0.00 | 0.33 | 0.01 | 0.50 | 0.02 | 0.73 |
| C18:1 n-7 | 0.00 | 0.00 | 0.00 | 0.00 | 0.00 | 0.00 | 0.00 | 0.00 |
| C18:2 n-6 | 0.00 | 0.00 | 0.00 | 0.00 | 0.00 | 0.00 | 0.00 | 0.00 |
| C20:0 | 0.28 | 0.20 | 0.27 | 0.20 | 0.43 | 0.38 | 0.45 | 0.40 |
| C18:3 n-3 | 0.00 | 0.00 | 0.00 | 0.00 | 0.00 | 0.00 | 0.00 | 0.00 |
| C20:1 n-9 | 0.00 | 0.00 | 0.00 | 0.00 | 0.00 | 0.00 | 0.00 | 0.00 |
| C18:4 n-3 | 0.17 | 0.18 | 0.21 | 0.21 | 0.62 | 0.32 | 0.59 | 0.33 |
| C20:2 n-6 | 0.00 | 0.00 | 0.00 | 0.00 | 0.00 | 0.00 | 0.00 | 0.00 |
| C20:3 n-6 | 0.00 | 0.00 | 0.00 | 0.00 | 0.00 | 0.00 | 0.00 | 0.00 |

TABLE 5-continued

Fatty Acid Profiles of PTA-10208 and PTA-10212 Biomasses and Extracted Crude Lipids (%)

| Fatty Acid | PTA-10208 Sample #1 Biomass % FAME | PTA-10208 Sample #1 Crude Lipid % FAME | PTA-10208 Sample #2 Biomass % FAME | PTA-10208 Sample #2 Crude Lipid % FAME | PTA-10212 Sample #1 Biomass % FAME | PTA-10212 Sample #1 Crude Lipid % FAME | PTA-10212 Sample #2 Biomass % FAME | PTA-10212 Sample #2 Crude Lipid % FAME |
|---|---|---|---|---|---|---|---|---|
| C22:0 | 0.02 | 0.00 | 0.01 | 0.00 | 0.08 | 0.02 | 0.09 | 0.03 |
| C20:4 n-7 | 0.15 | 0.05 | 0.13 | 0.04 | 0.00 | 0.00 | 0.00 | 0.00 |
| C20:4 n-6 | 1.37 | 1.35 | 1.32 | 1.29 | 0.32 | 0.28 | 0.35 | 0.29 |
| C22:1 n-9 | 0.00 | 0.00 | 0.00 | 0.00 | 0.00 | 0.00 | 0.00 | 0.00 |
| C20:4 n-5 | 0.12 | 0.06 | 0.00 | 0.05 | 0.00 | 0.00 | 0.00 | 0.00 |
| C20:4 n-3 | 0.65 | 0.60 | 0.64 | 0.59 | 0.00 | 0.30 | 0.00 | 0.29 |
| C20:3 n-3 | 0.02 | 0.00 | 0.02 | 0.00 | 0.00 | 0.00 | 0.00 | 0.00 |
| C20:5 n-3 | 20.36 | 20.59 | 17.93 | 17.96 | 10.96 | 11.19 | 11.58 | 11.57 |
| C22:4 n-9 | 0.00 | 0.00 | 0.00 | 0.00 | 0.00 | 0.00 | 0.00 | 0.00 |
| C24:0 | 0.11 | 0.00 | 0.10 | 0.00 | 0.76 | 0.85 | 0.74 | 0.82 |
| C24:1 n-9 | 0.29 | 0.36 | 0.16 | 0.22 | 0.12 | 0.17 | 0.11 | 0.16 |
| C22:5 n-6 | 1.83 | 1.75 | 1.98 | 1.91 | 0.66 | 0.58 | 0.62 | 0.53 |
| C22:5 n-3 | 3.88 | 3.87 | 1.91 | 1.86 | 0.65 | 0.61 | 0.72 | 0.65 |
| C22:6 n-3 | 46.85 | 46.64 | 47.42 | 47.10 | 37.94 | 35.93 | 36.86 | 34.71 |
| Sum of FAME % | 100 | 100 | 100 | 100 | 100 | 100 | 100 | 100 |

TABLE 6

Fatty Acid Profiles of PTA-10208 and PTA-10212 Isolated TAG

| Fatty Acid | PTA-10208 Sample #1 FAME (mg/g) | PTA-10208 Sample #1 % FAME | PTA-10208 Sample #2 FAME (mg/g) | PTA-10208 Sample #2 % FAME | PTA-10212 Sample #1 FAME (mg/g) | PTA-10212 Sample #1 % FAME | PTA-10212 Sample #2 FAME (mg/g) | PTA-10212 Sample #2 % FAME |
|---|---|---|---|---|---|---|---|---|
| C12:0 | 2.57 | 0.27 | 3.35 | 0.36 | 0.00 | 0.00 | 0.00 | 0.00 |
| C12:0 | 2.57 | 0.27 | 3.35 | 0.36 | 0.00 | 0.00 | 0.00 | 0.00 |
| C14:0 | 21.07 | 2.23 | 31.37 | 3.41 | 14.05 | 1.61 | 14.45 | 1.69 |
| C14:1 | 0.00 | 0.00 | 0.00 | 0.00 | 0.00 | 0.00 | 0.00 | 0.00 |
| C15:0 | 3.89 | 0.41 | 6.17 | 0.67 | 23.27 | 2.66 | 23.14 | 2.71 |
| C16:0 | 189.28 | 20.07 | 218.78 | 23.75 | 399.51 | 45.75 | 402.43 | 47.07 |
| C16:1 | 0.00 | 0.00 | 0.00 | 0.00 | 15.23 | 1.74 | 17.62 | 2.06 |
| C18:0 | 9.21 | 0.98 | 8.07 | 0.88 | 22.70 | 2.60 | 23.10 | 2.70 |
| C18:1 n-9 | 3.35 | 0.36 | 3.64 | 0.40 | 6.12 | 0.70 | 7.48 | 0.87 |
| C18:1 n-7 | 0.00 | 0.00 | 0.00 | 0.00 | <0.1 | <0.1 | <0.1 | <0.1 |
| C18:2 n-6 | 0.00 | 0.00 | 0.00 | 0.00 | 0.00 | 0.00 | 0.00 | 0.00 |
| C20:0 | 1.86 | 0.20 | 1.55 | 0.17 | 4.76 | 0.55 | 5.32 | 0.62 |
| C18:3 n-3 | 0.00 | 0.00 | 0.00 | 0.00 | 0.00 | 0.00 | 0.00 | 0.00 |
| C20:1 n-9 | 0.00 | 0.00 | 0.00 | 0.00 | 0.00 | 0.00 | 0.00 | 0.00 |
| C18:4 n-3 | 1.64 | 0.17 | 2.00 | 0.22 | 2.25 | 0.26 | 2.24 | 0.26 |
| C20:2 n-6 | 0.00 | 0.00 | 0.00 | 0.00 | 0.00 | 0.00 | 0.00 | 0.00 |
| C20:3 n-6 | 0.00 | 0.00 | 0.00 | 0.00 | 0.00 | 0.00 | 0.00 | 0.00 |
| C22:0 | 0.00 | 0.00 | 0.00 | 0.00 | 0.55 | 0.06 | 0.89 | 0.10 |
| Un-known | 0.00 | 0.00 | 0.00 | 0.00 | 0.00 | 0.00 | 0.00 | 0.00 |
| C20:4 n-7 | 0.39 | 0.04 | 0.05 | 0.01 | 0.00 | 0.00 | 0.00 | 0.00 |
| C20:3 n-3 | 0.00 | 0.00 | 0.00 | 0.00 | 0.00 | 0.00 | 0.00 | 0.00 |
| C20:4 n-6 | 12.79 | 1.36 | 11.82 | 1.28 | 2.33 | 0.27 | 2.25 | 0.26 |
| C22:1 n-9 | 0.00 | 0.00 | 0.00 | 0.00 | 0.00 | 0.00 | 0.00 | 0.00 |
| C20:4 n-5 | 0.39 | 0.04 | 0.07 | 0.01 | 0.00 | 0.00 | 0.00 | 0.00 |
| C20:4 n-3 | 5.52 | 0.59 | 5.09 | 0.55 | 2.87 | 0.33 | 2.98 | 0.35 |
| C20:5 n-3 | 197.14 | 20.90 | 166.68 | 18.10 | 91.17 | 10.44 | 91.78 | 10.74 |
| C24:0 | 0.00 | 0.00 | 0.00 | 0.00 | 6.93 | 0.79 | 7.36 | 0.86 |
| C22:4 n-9 | 0.00 | 0.00 | 0.00 | 0.00 | 0.00 | 0.00 | 0.00 | 0.00 |

TABLE 6-continued

Fatty Acid Profiles of PTA-10208 and PTA-10212 Isolated TAG

| Fatty Acid | PTA-10208 Sample #1 FAME (mg/g) | PTA-10208 Sample #1 % FAME | PTA-10208 Sample #2 FAME (mg/g) | PTA-10208 Sample #2 % FAME | PTA-10212 Sample #1 FAME (mg/g) | PTA-10212 Sample #1 % FAME | PTA-10212 Sample #2 FAME (mg/g) | PTA-10212 Sample #2 % FAME |
|---|---|---|---|---|---|---|---|---|
| C24:1 n-9 | 1.08 | 0.11 | <0.1 | <0.1 | 0.00 | 0.00 | 0.00 | 0.00 |
| C22:5 n-6 | 15.88 | 1.68 | 16.57 | 1.80 | 4.01 | 0.46 | 3.39 | 0.40 |
| C22:5 n-3 | 36.05 | 3.82 | 16.00 | 1.74 | 4.53 | 0.52 | 5.07 | 0.59 |
| C22:6 n-3 | 440.99 | 46.76 | 429.83 | 46.67 | 273.02 | 31.26 | 245.38 | 28.70 |
| Sum of FAME | 943.11 | — | 921.03 | — | 873.31 | — | 854.89 | — |
| Total % FAME | — | 100.00 | — | 100.00 | — | 100.00 | — | 100.00 |

TABLE 7

Fatty Acid Profiles of PTA-10212 Isolated PL

| Fatty Acid | PTA-10212 Sample #1 FAME (mg/g) | PTA-10212 Sample #1 % FAME | PTA-10212 Sample #2 FAME (mg/g) | PTA-10212 Sample #2 % FAME |
|---|---|---|---|---|
| C12:0 | 0.00 | 0.00 | 0.00 | 0.00 |
| C14:0 | 0.93 | 0.22 | 1.89 | 0.39 |
| C14:1 | 0.00 | 0.00 | 0.00 | 0.00 |
| C15:0 | 3.44 | 0.82 | 5.07 | 1.05 |
| C16:0 | 98.29 | 23.50 | 120.98 | 25.00 |
| C16:1 | 1.15 | 0.27 | 3.07 | 0.63 |
| C18:0 | 3.25 | 0.78 | 3.72 | 0.77 |
| C18:1 n-9 | 1.12 | 0.27 | 0.95 | 0.20 |
| C18:1 n-7 | <0.1 | <0.1 | 0.02 | 0.003 |
| C18:2 n-6 | 0.00 | 0.00 | 0.00 | 0.00 |
| C20:0 | <0.1 | <0.1 | <0.1 | <0.1 |
| C18:3 n-3 | 0.00 | 0.00 | 0.00 | 0.00 |
| C20:1 n-9 | 0.00 | 0.00 | 0.00 | 0.00 |
| C18:4 n-3 | 3.71 | 0.89 | 3.24 | 0.67 |
| C20:2 n-6 | 0.00 | 0.00 | 0.00 | 0.00 |
| C20:3 n-6 | 0.00 | 0.00 | 0.00 | 0.00 |
| C22:0 | 0.00 | 0.00 | 0.00 | 0.00 |
| Unknown | 42.33 | 10.12 | 44.71 | 9.24 |
| C20:4 n-7 | 0.00 | 0.00 | 0.00 | 0.00 |
| C20:3 n-3 | 0.00 | 0.00 | 0.00 | 0.00 |
| C20:4 n-6 | 0.84 | 0.20 | 1.54 | 0.32 |
| C22:1 n-9 | 0.00 | 0.00 | 0.00 | 0.00 |
| C20:4 n-5 | 0.00 | 0.00 | 0.00 | 0.00 |
| C20:4 n-3 | <0.1 | <0.1 | 0.27 | 0.06 |
| C20:5 n-3 | 33.39 | 7.98 | 47.91 | 9.90 |
| C24:0 | <0.1 | <0.1 | 0.01 | 0.001 |
| C22:4 n-9 | 0.00 | 0.00 | 0.00 | 0.00 |
| C24:1 n-9 | 0.00 | 0.00 | 0.00 | 0.00 |
| C22:5 n-6 | 3.08 | 0.74 | 3.82 | 0.79 |
| C22:5 n-3 | <0.1 | <0.1 | 0.66 | 0.14 |
| C22:6 n-3 | 226.68 | 54.20 | 246.09 | 50.85 |
| Sum of FAME | 418.21 | — | 483.94 | — |
| Total % FAME | — | 100 | — | 100 |

PTA-10212 Sample #3

The lipid content of the biomass for PTA-10212 Sample #3 was estimated to be 34% as the sum of FAME, and the amount of crude oil obtained after solvent extraction was 37% by weight, giving a 109% recovery of fat present in the biomass. After fractionation using flash chromatography, approximately 46% of the crude oil was isolated as TAG, 28% was isolated as DAG, The crude oil contained 309 mg/g DHA and 264 mg/g EPA. The isolated TAG contained 341 mg/g DHA and 274 mg/g EPA. The isolated DAG fraction contained 262 mg/g DHA and 237 mg/g EPA. The total fatty acid profiles of the biomass, extracted crude oil, and isolated fractions are shown below in Table 8 and Table 9 calculated as mg/g and % FAME, respectively.

TABLE 8

Fatty Acid Profiles of PTA-10212 Sample #3 Biomass and Extracted Crude Lipid (mg/g)

| | Biomass | Crude Oil | TAG | DAG |
|---|---|---|---|---|
| | | Wt. % | | |
| | NA | 37.2% | 46.0% | 27.9% |
| Fatty Acid | FAME (mg/g) | FAME (mg/g) | FAME (mg/g) | FAME (mg/g) |
| C12:0 | 0.0 | 0.0 | 0.0 | 0.0 |
| C14:0 | 3.6 | 10.3 | 11.5 | 9.4 |
| C14:1 | 0.0 | 0.0 | 0.0 | 0.0 |
| C15:0 | 4.1 | 10.6 | 9.8 | 6.6 |
| C16:0 | 70.5 | 181.8 | 231.7 | 111.3 |
| C16:1 | 6.7 | 19.1 | 18.7 | 17.1 |
| C18:0 | 2.4 | 10.2 | 14.2 | 0.0 |
| C18:1 n-9 | 0.0 | 6.7 | 0.0 | 0.0 |
| C18:1 n-7 | 0.0 | 1.2 | 0.0 | 0.0 |
| C18:2 n-6 | 0.0 | 1.8 | 0.0 | 0.0 |
| C20:0 | 0.0 | 2.4 | 0.0 | 0.0 |
| C18:3 n-3 | 0.0 | 0.0 | 0.0 | 0.0 |
| C20:1 n-9 | 0.0 | 0.3 | 0.0 | 1.7 |
| C18:4 n-3 | 1.9 | 3.4 | 3.2 | 4.4 |
| C20:2 n-6 | 0.0 | 0.0 | 0.0 | 0.0 |
| C20:3 n-6 | 0.0 | 0.0 | 0.0 | 0.0 |
| C22:0 | 3.3 | 0.0 | 0.0 | 0.0 |
| C20:4 n-7 | 0.0 | 2.1 | 1.5 | 0.0 |
| C20:3 n-3 | 0.0 | 0.0 | 0.0 | 0.0 |
| C20:4 n-6 | 6.8 | 17.9 | 21.4 | 13.8 |
| C22:1 n-9 | 0.0 | 0.0 | 0.0 | 0.0 |
| C20:4 n-5 | 0.0 | 1.3 | 1.3 | 0.0 |
| C20:4 n-3 | 3.0 | 8.5 | 10.9 | 6.4 |
| C20:5 n-3 | 102.0 | 263.6 | 274.2 | 237.4 |
| C24:0 | 0.0 | 1.7 | 3.9 | 0.0 |
| C22:4 n-9 | 0.0 | 0.0 | 0.0 | 0.0 |
| C24:1 n-9 | 0.0 | 0.0 | 4.2 | 0.0 |
| C22:5 n-6 | 3.2 | 8.3 | 10.7 | 6.1 |
| C22:5 n-3 | 3.8 | 10.4 | 15.1 | 6.6 |
| C22:6 n-3 | 131.2 | 309.4 | 341.1 | 261.9 |
| Sum of FAME | 342.4 | 871.1 | 973.2 | 682.6 |

TABLE 9

Fatty Acid Profiles of PTA-10212 Sample #3 Biomass and Extracted Crude Lipid (%)

| Fatty Acid | Biomass NA FAME (mg/g) | Crude Oil Wt. % 37.2% FAME (mg/g) | TAG 46.0% FAME (mg/g) | DAG 27.9% FAME (mg/g) |
|---|---|---|---|---|
| C12:0 | 0.0 | 0.0 | 0.0 | 0.0 |
| C14:0 | 1.1 | 1.2 | 1.2 | 1.4 |
| C14:1 | 0.0 | 0.0 | 0.0 | 0.0 |
| C15:0 | 1.2 | 1.2 | 1.0 | 1.0 |
| C16:0 | 20.6 | 20.9 | 23.8 | 16.3 |
| C16:1 | 2.0 | 2.2 | 1.9 | 2.5 |
| C18:0 | 0.7 | 1.2 | 1.5 | 0.0 |
| C18:1 n-9 | 0.0 | 0.8 | 0.0 | 0.0 |
| C18:1 n-7 | 0.0 | 0.1 | 0.0 | 0.0 |
| C18:2 n-6 | 0.0 | 0.2 | 0.0 | 0.0 |
| C20:0 | 0.0 | 0.3 | 0.0 | 0.0 |
| C18:3 n-3 | 0.0 | 0.0 | 0.0 | 0.0 |
| C20:1 n-9 | 0.0 | 0.0 | 0.0 | 0.2 |
| C18:4 n-3 | 0.6 | 0.4 | 0.3 | 0.6 |
| C20:2 n-6 | 0.0 | 0.0 | 0.0 | 0.0 |
| C20:3 n-6 | 0.0 | 0.0 | 0.0 | 0.0 |
| C22:0 | 1.0 | 0.0 | 0.0 | 0.0 |
| C20:4 n-7 | 0.0 | 0.2 | 0.2 | 0.0 |
| C20:3 n-3 | 0.0 | 0.0 | 0.0 | 0.0 |
| C20:4 n-6 | 2.0 | 2.1 | 2.2 | 2.0 |
| C22:1 n-9 | 0.0 | 0.0 | 0.0 | 0.0 |
| C20:4 n-5 | 0.0 | 0.1 | 0.1 | 0.0 |
| C20:4 n-3 | 0.9 | 1.0 | 1.1 | 0.9 |
| C20:5 n-3 | 29.8 | 30.3 | 28.2 | 34.8 |
| C24:0 | 0.0 | 0.2 | 0.4 | 0.0 |
| C22:4 n-9 | 0.0 | 0.0 | 0.0 | 0.0 |
| C24:1 n-9 | 0.0 | 0.0 | 0.4 | 0.0 |
| C22:5 n-6 | 0.9 | 1.0 | 1.1 | 0.9 |
| C22:5 n-3 | 1.1 | 1.2 | 1.6 | 1.0 |
| C22:6 n-3 | 38.3 | 35.5 | 35.1 | 38.4 |
| Total % FAME | 100.0 | 100.0 | 100.0 | 100.0 |

PTA-10212 Sample #4

PTA-10212 Sample #4 contained approximately 23% lipid determined as the sum of FAME, of which 107% was recovered using hexane extraction. After fractionation using flash chromatography, approximately 42% of the crude oil was isolated as TAG, 18% was isolated as DAG. The crude oil contained 275 mg/g DHA and 209 mg/g EPA. The isolated TAG contained 296 mg/g DHA and 205 mg/g EPA. The isolated DAG fraction contained 245 mg/g DHA and 219 mg/g EPA. The total fatty acid profiles of the biomass, extracted crude oil, and isolated fractions are shown below in Table 10 (mg/g) and Table 11 (% FAME).

TABLE 10

Fatty Acid Profiles of PTA-10212 Sample #4 Biomass and Extracted Crude Lipid (mg/g)

| Fatty Acid | Biomass NA FAME (mg/g) | Crude Oil Wt. % 24.7% FAME (mg/g) | TAG 42.2% FAME (mg/g) | DAG 18.4% FAME (mg/g) |
|---|---|---|---|---|
| C12:0 | 0.0 | 0.0 | 2.1 | 2.4 |
| C14:0 | 2.0 | 8.3 | 9.8 | 9.6 |
| C14:1 | 0.0 | 0.0 | 0.0 | 0.0 |
| C15:0 | 4.8 | 16.8 | 0.4 | 0.9 |
| C16:0 | 63.3 | 210.6 | 285.7 | 138.0 |
| C16:1 | 1.6 | 6.7 | 7.4 | 7.5 |
| C18:0 | 2.8 | 12.2 | 19.9 | 4.6 |
| C18:1 n-9 | 0.0 | 3.7 | 0.7 | 1.1 |
| C18:1 n-7 | 0.0 | 0.0 | 0.3 | 1.2 |
| C18:2 n-6 | 0.0 | 0.0 | 0.0 | 0.0 |
| C20:0 | 0.0 | 3.3 | 6.0 | 1.5 |
| C18:3 n-3 | 0.0 | 0.0 | 0.0 | 0.0 |
| C20:1 n-9 | 0.0 | 0.0 | 0.7 | 1.2 |
| C18:4 n-3 | 1.4 | 3.8 | 3.6 | 5.0 |
| C20:2 n-6 | 0.0 | 0.0 | 0.0 | 0.0 |
| C20:3 n-6 | 0.0 | 0.0 | 0.4 | 0.0 |
| C22:0 | 1.5 | 0.0 | 1.9 | 0.0 |
| C20:4 n-7 | 0.0 | 0.0 | 0.9 | 0.6 |
| C20:3 n-3 | 0.0 | 0.0 | 0.0 | 0.0 |
| C20:4 n-6 | 2.5 | 10.1 | 13.0 | 10.3 |
| C22:1 n-9 | 0.0 | 0.0 | 0.0 | 0.0 |
| C20:4 n-5 | 0.0 | 0.0 | 0.8 | 0.7 |
| C20:4 n-3 | 1.4 | 6.3 | 8.6 | 6.0 |
| C20:5 n-3 | 57.6 | 209.1 | 205.4 | 219.0 |
| C24:0 | 0.0 | 2.6 | 0.8 | 0.0 |
| C22:4 n-9 | 0.1 | 0.0 | 0.0 | 0.0 |
| C24:1 n-9 | 0.0 | 0.0 | 1.1 | 0.5 |
| C22:5 n-6 | 1.4 | 6.1 | 7.9 | 4.5 |
| C22:5 n-3 | 4.0 | 15.8 | 20.8 | 12.9 |
| C22:6 n-3 | 87.7 | 275.0 | 296.4 | 244.8 |
| Sum of FAME | 232.2 | 790.1 | 894.8 | 672.4 |

TABLE 11

Fatty Acid Profiles of PTA-10212 Sample #4 Biomass and Extracted Crude Lipid (%)

| Fatty Acid | Biomass NA FAME (mg/g) | Crude Oil Wt. % 24.7% FAME (mg/g) | TAG 42.2% FAME (mg/g) | DAG 18.4% FAME (mg/g) |
|---|---|---|---|---|
| C12:0 | 0.0 | 0.0 | 0.2 | 0.4 |
| C14:0 | 0.9 | 1.0 | 1.1 | 1.4 |
| C14:1 | 0.0 | 0.0 | 0.0 | 0.0 |
| C15:0 | 2.1 | 2.1 | 0.0 | 0.1 |
| C16:0 | 27.3 | 26.7 | 31.9 | 20.5 |
| C16:1 | 0.7 | 0.8 | 0.8 | 1.1 |
| C18:0 | 1.2 | 1.5 | 2.2 | 0.7 |
| C18:1 n-9 | 0.0 | 0.5 | 0.1 | 0.2 |
| C18:1 n-7 | 0.0 | 0.0 | 0.0 | 0.2 |
| C18:2 n-6 | 0.0 | 0.0 | 0.0 | 0.0 |
| C20:0 | 0.0 | 0.4 | 0.7 | 0.2 |
| C18:3 n-3 | 0.0 | 0.0 | 0.0 | 0.0 |
| C20:1 n-9 | 0.0 | 0.0 | 0.1 | 0.2 |
| C18:4 n-3 | 0.6 | 0.5 | 0.4 | 0.7 |
| C20:2 n-6 | 0.0 | 0.0 | 0.0 | 0.0 |
| C20:3 n-6 | 0.0 | 0.0 | 0.0 | 0.0 |
| C22:0 | 0.6 | 0.0 | 0.2 | 0.0 |
| C20:4 n-7 | 0.0 | 0.0 | 0.1 | 0.1 |
| C20:3 n-3 | 0.0 | 0.0 | 0.0 | 0.0 |
| C20:4 n-6 | 1.1 | 1.3 | 1.5 | 1.5 |
| C22:1 n-9 | 0.0 | 0.0 | 0.0 | 0.0 |
| C20:4 n-5 | 0.0 | 0.0 | 0.1 | 0.1 |
| C20:4 n-3 | 0.6 | 0.8 | 1.0 | 0.9 |
| C20:5 n-3 | 24.8 | 26.5 | 23.0 | 32.6 |
| C24:0 | 0.0 | 0.3 | 0.1 | 0.0 |
| C22:4 n-9 | 0.0 | 0.0 | 0.0 | 0.0 |

TABLE 11-continued

Fatty Acid Profiles of PTA-10212 Sample #4 Biomass and Extracted Crude Lipid (%)

| | Biomass | Crude Oil | TAG | DAG |
|---|---|---|---|---|
| | | | Wt. % | |
| Fatty Acid | NA FAME (mg/g) | 24.7% FAME (mg/g) | 42.2% FAME (mg/g) | 18.4% FAME (mg/g) |
| C24:1 n-9 | 0.0 | 0.0 | 0.1 | 0.1 |
| C22:5 n-6 | 0.6 | 0.8 | 0.9 | 0.7 |
| C22:5 n-3 | 1.7 | 2.0 | 2.3 | 1.9 |
| C22:6 n-3 | 37.8 | 34.8 | 33.1 | 36.4 |
| Total % FAME | 100.0 | 100.0 | 100.0 | 100.0 |

PTA-10212 Sample #5

A sample of crude oil was extracted from a biomass of PTA-10212 using the FRIOLEX® process (GEA Westfalia Separator UK Ltd., Milton Keynes, England) to yield microbial oil PTA-10212 Sample #5. Individual lipid classes were isolated from PTA-10212 Sample #5 using low pressure flash chromatography, and the weight percent of each class was determined. The fatty acid profile of each class was determined using GC-FID.

Briefly, the sample was prepared by dissolving 240 mg of crude oil in 600 µL of hexane and applying to the head of the column. After fractionation of the sample using flash chromatography, the combined weights of all the fractions was 240 mg giving a 100% recovery. The sterol ester fraction accounted for 0.9%, the TAG fraction accounted for 42.6%, the free fatty acid (FFA) fraction accounted for 1.3%, the sterol fraction accounted for 2.2%, the DAG fraction accounted for 41.6%. The total fatty acid profiles of the FRIOLEX® crude oil and isolated fractions are shown below in Table 12 and Table 13 calculated as mg/g and % FAME, respectively.

TABLE 12

Fatty Acid Profiles of PTA-10212 Sample #5 Crude Oil (mg/g)

| | Crude Oil | TAG | DAG |
|---|---|---|---|
| | | Wt. % | |
| Fatty Acid | NA FAME (mg/g) | 42.6% FAME (mg/g) | 41.6% FAME (mg/g) |
| C12:0 | 0 | 0.7 | 1.0 |
| C14:0 | 7.7 | 7.7 | 8.5 |
| C14:1 | 0 | 0.0 | 0.0 |
| C15:0 | 10.3 | 11.7 | 9.3 |
| C16:0 | 179.3 | 217.7 | 134.6 |
| C16:1 | 18.1 | 16.3 | 25.9 |
| C18:0 | 8.1 | 13.2 | 2.3 |
| C18:1 n-9 | 4.7 | 8.4 | 0.7 |
| C18:1 n-7 | 0 | 1.8 | 1.0 |
| C18:2 n-6 | 1.8 | 3.3 | 0.7 |
| C20:0 | 1.9 | 3.6 | 0.2 |
| C18:3 n-3 | 0 | 0.0 | 0.0 |
| C20:1 n-9 | 0 | 0.7 | 1.0 |
| C18:4 n-3 | 3.1 | 2.8 | 3.8 |
| C20:2 n-6 | 0 | 0.0 | 0.0 |
| C20:3 n-6 | 0 | 0.6 | 0.4 |
| C22:0 | 0 | 1.5 | 0.0 |
| C20:4 n-7 | 0 | 1.0 | 0.7 |
| C20:3 n-3 | 0 | 0.0 | 0.0 |
| C20:4 n-6 | 12.7 | 16.1 | 13.6 |
| C22:1 n-9 | 0 | 0.0 | 0.0 |
| C20:4 n-5 | 0 | 1.5 | 0.8 |
| C20:4 n-3 | 6.5 | 9.3 | 6.4 |
| C20:5 n-3 | 213.3 | 223.7 | 252.8 |

TABLE 12-continued

Fatty Acid Profiles of PTA-10212 Sample #5 Crude Oil (mg/g)

| | Crude Oil | TAG | DAG |
|---|---|---|---|
| | | Wt. % | |
| Fatty Acid | NA FAME (mg/g) | 42.6% FAME (mg/g) | 41.6% FAME (mg/g) |
| C24:0 | 2.3 | 4.4 | 0.6 |
| C22:4 n-9 | 0 | 1.9 | 0.9 |
| C24:1 n-9 | 0 | 0.0 | 0.0 |
| C22:5 n-6 | 7.9 | 9.5 | 8.3 |
| C22:5 n-3 | 13 | 20.6 | 9.7 |
| C22:6 n-3 | 305.6 | 327.4 | 353.8 |
| Sum of FAME | 796.6 | 905.3 | 837.4 |

TABLE 13

Fatty Acid Profiles of PTA-10212 Sample #5 Crude Oil (%)

| Fatty Acid | Crude Oil % FAME | TAG % FAME | DAG % FAME |
|---|---|---|---|
| C12:0 | 0 | 0.1 | 0.1 |
| C14:0 | 1 | 0.9 | 1.0 |
| C14:1 | 0 | 0.0 | 0.0 |
| C15:0 | 1.3 | 1.3 | 1.1 |
| C16:0 | 22.5 | 24.0 | 16.1 |
| C16:1 | 2.3 | 1.8 | 3.1 |
| C18:0 | 1 | 1.5 | 0.3 |
| C18:1 n-9 | 0.6 | 0.9 | 0.1 |
| C18:1 n-7 | 0 | 0.2 | 0.1 |
| C18:2 n-6 | 0.2 | 0.4 | 0.1 |
| C20:0 | 0.2 | 0.4 | 0.0 |
| C18:3 n-3 | 0 | 0.0 | 0.0 |
| C20:1 n-9 | 0 | 0.1 | 0.1 |
| C18:4 n-3 | 0.4 | 0.3 | 0.5 |
| C20:2 n-6 | 0 | 0.0 | 0.0 |
| C20:3 n-6 | 0 | 0.1 | 0.0 |
| C22:0 | 0 | 0.2 | 0.0 |
| C20:4 n-7 | 0 | 0.1 | 0.1 |
| C20:3 n-3 | 0 | 0.0 | 0.0 |
| C20:4 n-6 | 1.6 | 1.8 | 1.6 |
| C22:1 n-9 | 0 | 0.0 | 0.0 |
| C20:4 n-5 | 0 | 0.2 | 0.1 |
| C20:4 n-3 | 0.8 | 1.0 | 0.8 |
| C20:5 n-3 | 26.8 | 24.7 | 30.2 |
| C24:0 | 0.3 | 0.5 | 0.1 |
| C22:4 n-9 | 0 | 0.2 | 0.1 |
| C24:1 n-9 | 0 | 0.0 | 0.0 |
| C22:5 n-6 | 1 | 1.1 | 1.0 |
| C22:5 n-3 | 1.6 | 2.3 | 1.2 |
| C22:6 n-3 | 38.4 | 36.2 | 42.3 |
| Total % FAME | 100 | 100 | 100 |

EXAMPLE 4

The relative amount and fatty acid composition of each TAG isomer present in the extracted crude lipid was determined for each of samples PTA-10208 Sample #1, PTA-10208 Sample #2, PTA-10212 Sample #1, PTA-10212 Sample #2, and PTA-10212 Sample #3, PTA-10212 Sample #4, and PTA-10212 Sample #5 from Example 3 using non-aqueous reversed phase HPLC separation and APCI-MS detection.

| TAG Method - | | | |
|---|---|---|---|
| Instrument | Agilent 1100 HPLC | | |
|  | Agilent 1100 MSD | | |
| Column(s) | Two Phenomenex Luna C18 (2), 150 × 4.6 mm, 3 μm particle size connected in series | | |
| Mobile Phase | A - Acetonitrile | | |
|  | B - IPA w/ 0.1% Ammonium Acetate | | |
|  | Time, min. | % A | % B |
| Gradient | 0 | 80 | 20 |
|  | 120 | 20 | 80 |
|  | 125 | 20 | 80 |
|  | 126 | 80 | 20 |
|  | 140 | 80 | 20 |

| -continued | |
|---|---|
| Column Temp. | 20° C. |
| Flow Rate | 0.5 mL/min |
| Injection Volume | 5 μL |
| MSD | Mass Range 350-1150 |
|  | Fragmentor 225 V |
|  | Drying Gas Temperature 350° C., |
|  | Vaporizor Temperature 325° C. |
|  | Capillary Voltage 3500 V |
|  | Corona Current 10 μA |

PTA-10208 Sample #1

The crude lipid isolated from PTA-10208 Sample #1 was prepared for TAG analysis prepared for TAG analysis by weighing 5.5 mg of oil into an HPLC vial and diluting with 1 mL of hexane.

TABLE 14

Identification of TAG Species in PTA-10208 Sample #1

| Retention Time | CN | Identification | Area Percent | $[M + H]^+$ | $[M + NH_4]^+$ | Major (DAG) Fragments |
|---|---|---|---|---|---|---|
| 41.76 | 30 | EPA/EPA/EPA | 1.2 | 945.8 | 962.7 | 643.5 |
| 42.97 | 30 | EPA/EPA/DHA | 5.4 | 971.7 | 988.8 | 643.4, 669.5 |
| 44.17 | 30 | DHA/DHA/EPA | 8.8 | 997.7 | 1014.7 | 669.5, 695.5 |
| 45.39 | 30 | DHA/DHA/DHA | 7.4 | 1023.7 | 1040.7 | 695.5 |
| 46.32 | 32 | DHA/EPA/ARA | 1.1 | 973.8 | 990.8 | 645.4, 671.5 |
| 47.53 | 32 | DHA/DPA/EPA | 2.0 | 999.8 | 1016.8 | 671.5, 697.5 |
| 48.88 | 32 | DHA/EPA/ARA | 2.6 | 973.8 | 990.7 | 645.4, 671.5 |
|  |  | DHA/DHA/DPA |  | 1025.7 | 1042.8 | 697.5 |
| 50.23 | 32 | DHA/DPA/EPA | 1.8 | 999.8 | 1016.8 | 671.5, 697.4 |
| 51.47 | 32 | DHA/DPA/DHA | 1.5 | 1025.7 | 1042.8 | 695.5, 697.5 |
| 54.64 | 34 | EPA/14:0/DHA | 1.8 | 897.7 | 914.7 | 569.5, 595.5 |
| 55.80 | 34 | DHA/DHA/14:0 | 2.2 | 923.6 | 940.8 | 595.5, 695.5 |
| 60.73 | 36 | EPA/EPA/16:0 | 3.4 | 899.7 | 916.8 | 597.5, 643.3 |
| 61.87 | 36 | DHA/16:0/EPA | 11.8 | 925.8 | 942.7 | 597.5, 623.5, 669.5 |
| 63.0 | 36 | DHA/16:0/DHA | 17.7 | 951.8 | 968.8 | 623.5, 695.5 |
| 65.47 | 38 | EPA/EPA/18:0 | 2.3 | 927.7 | 944.8 | 625.5 |
| 66.58 | 38 | DHA/DPA/16:0 | 2.9 | 953.8 | 970.8 | 623.5, 625.5, 697.6 |
| 67.31 | 38 | EPA/ARA/16:0 | 1.0 | 901.7 | 918.8 | 597.6, 599.5, 645.4 |
| 68.39 | 38 | DHA/16:0/ARA | 2.0 | 927.7 | 944.8 | 625.6 |
| 69.52 | 38 | DHA/16:0/DPA | 2.3 | 953.8 | 970.8 | 623.5, 625.5 |
| 70.16 | 38 | DHA/DHA/18:0 | 0.9 | 979.5 | 996.7 | 651.5 |
| 73.81 | 40 | EPA/16:0/14:0 | 1.0 | 825.7 | 842.7 | 523.5, 569.5, 597.5 |
| 74.73 | 40 | DHA/14:0/16:0 | 1.5 | 851.7 | 868.7 | 523.4, 623.5 |
| 80.96 | 42 | EPA/16:0/16:0 | 1.8 | 853.6 | 870.8 | 551.5, 597.4 |
| 81.93 | 42 | DHA/16:0/16:0 | 6.5 | 879.8 | 896.8 | 551.5, 623.5 |
| 85.50 | 44 | DPA/16:0/16:0 | 0.9 | 881.7 | 898.8 | 551.4, 625.4 |
| 88.92 | 44 | 18:0/16:0/DHA | 0.9 | 907.9 | 924.8 | 579.4, 651.5 |

PTA-10208 Sample #2

The crude lipid isolated from PTA-10208 Sample #2 was prepared for TAG analysis prepared for TAG analysis by weighing 5.3 mg of oil into an HPLC vial and diluting with 1 mL of hexane.

TABLE 15

Identification of TAG Species in PTA-10208 Sample #2

| Retention Time | CN | Identification | Area Percent | $[M + H]^+$ | $[M + NH_4]^+$ | Major (DAG) Fragments |
|---|---|---|---|---|---|---|
| 41.70 | 30 | EPA/EPA/EPA | 1.0 | 945.7 | 962.8 | 643.5 |
| 42.92 | 30 | EPA/EPA/DHA | 4.3 | 971.7 | 988.8 | 643.5, 669.5 |
| 44.11 | 30 | DHA/DHA/EPA | 6.9 | 997.8 | 1014.8 | 669.5, 695.5 |
| 45.33 | 30 | DHA/DHA/DHA | 6.2 | 1023.8 | 1040.8 | 695.5 |
| 46.26 | 32 | DHA/EPA/ARA | 0.5 | 973.7 | 990.7 | 645.4, 671.5 |
| 47.47 | 32 | DHA/DPA/EPA | 1.1 | 999.8 | 1016.8 | 671.5, 697.5 |
| 48.86 | 32 | DHA/EPA/ARA | 1.9 | 973.7 | 990.7 | 645.5, 671.5 |
|  |  | DHA/DHA/DPA |  | 1025.7 | 1042.8 | 697.5 |
| 50.16 | 32 | DHA/DPA/EPA | 1.5 | 999.6 | 1016.9 | 671.5, 697.4 |
| 51.37 | 32 | DHA/DPA/DHA | 1.1 | 1025.7 | 1042.8 | 695.5, 697.5 |
| 54.57 | 34 | EPA/14:0/DHA | 2.0 | 897.7 | 914.7 | 569.5, 595.4 |

TABLE 15-continued

Identification of TAG Species in PTA-10208 Sample #2

| Retention Time | CN | Identification | Area Percent | [M + H]+ | [M + NH4]+ | Major (DAG) Fragments |
|---|---|---|---|---|---|---|
| 55.78 | 34 | DHA/DHA/14:0 | 2.9 | 923.6 | 940.8 | 595.5, 695.5 |
| 60.74 | 36 | EPA/EPA/16:0 | 3.1 | 899.6 | 916.8 | 597.5, 643.5 |
| 61.94 | 36 | DHA/16:0/EPA | 13.00 | 925.7 | 942.8 | 597.5, 623.5, 669.5 |
| 63.10 | 36 | DHA/16:0/DHA | 20.0 | 951.8 | 968.8 | 623.5, 695.5 |
| 65.60 | 38 | EPA/EPA/18:0 | 1.6 | 927.7 | 944.8 | 625.5 |
| 66.71 | 38 | DHA/DPA/16:0 | 2.0 | 953.7 | 970.8 | 623.6, 625.4, 697.6 |
| 67.46 | 38 | DHA/14:0/14:0 | 1.3 | 823.5 | 840.7 | 495.4, 595.5 |
|  |  | EPA/ARA/16:0 |  | 901.8 | 918.8 | 597.6, 599.5, 645.4 |
| 68.60 | 38 | DHA/16:0/ARA | 2.0 | 927.8 | 944.8 | 599.5, 623.5, 671.5 |
| 69.69 | 38 | DHA/16:0/DPA | 2.7 | 953.7 | 970.8 | 623.5, 625.5 |
| 70.39 | 38 | DHA/DHA/18:0 | 0.7 | 979.8 | 996.8 | 651.5 |
| 73.88 | 40 | EPA/16:0/14:0 | 1.1 | 825.7 | 842.8 | 523.5, 569.3, 597.3 |
| 74.94 | 40 | DHA/14:0/16:0 | 2.9 | 851.8 | 868.7 | 523.5, 623.5 |
| 81.17 | 42 | EPA/16:0/16:0 | 1.9 | 853.8 | 870.8 | 551.5, 597.6 |
| 82.16 | 42 | DHA/16:0/16:0 | 9.7 | 879.7 | 896.7 | 551.5, 623.5 |
| 85.72 | 44 | DPA/16:0/16:0 | 0.6 | 881.7 | 898.8 | 551.4, 625.5 |
| 89.15 | 44 | 18:0/16:0/DHA | 1.2 | 907.7 | 924.8 | 579.4, 651.5 |

PTA-10212 Sample #1
The crude lipid isolated from PTA-10212 Sample #1 was prepared for TAG analysis prepared for TAG analysis by weighing 5.3 mg of oil into an HPLC vial and diluting with 1 mL of hexane.

PTA-10212 Sample #2
The crude lipid isolated from PTA-10212 Sample #2 was prepared for TAG analysis prepared for TAG analysis by weighing 3.6 mg of oil into an HPLC vial and diluting with 1 mL of hexane.

TABLE 16

Identification of TAG Species in PTA-10212 Sample #1

| Retention Time | CN | Identification | Area Percent | [M + H]+ | [M + NH4]+ | (DAG) Fragments |
|---|---|---|---|---|---|---|
| 43.01 | 30 | EPA/EPA/DHA | 1.2 | 971.7 | 988.7 | 643.5, 669.5 |
| 44.24 | 30 | DHA/DHA/EPA | 2.6 | 997.7 | 1014.8 | 669.5, 695.4 |
| 45.41 | 30 | DHA/DHA/DHA | 2.4 | 1023.8 | 1040.8 | 695.5 |
| 54.78 | 34 | DHA/EPA/14:0 | 0.7 | 897.7 | 914.8 | 569.3, 595.4 |
|  |  | DHA/DHA/16:1 |  | 949.7 | 966.7 | 621.3, 695.3 |
| 59.53 | 35 | DHA/15:0/DHA | 0.9 | 937.8 | 954.8 | 609.6, 695.5 |
| 60.88 | 36 | EPA/16:0/EPA | 1.5 | 899.7 | 916.7 | 597.5, 643.2 |
| 62.03 | 36 | EPA/16:0/DHA | 8.3 | 925.8 | 942.7 | 597.6, 623.4 |
| 63.17 | 36 | DHA/16:0/DHA | 13.1 | 951.7 | 968.8 | 623.5, 695.5 |
| 66.82 | 38 | DHA/18:0/EPA | 1.5 | 953.7 | 970.8 | 625.6 |
| 68.63 | 38 | DHA/ARA/16:0 | 0.7 | 927.7 | 944.7 | 599.5, 623.3, 671.5 |
| 69.79 | 38 | DHA/DPA/16:0 | 0.7 | 953.8 | 970.8 | 623.5, 625.5 |
| 70.41 | 38 | DHA/DHA/18:0 | 0.7 | 979.7 | 996.7 | 651.5, 695.3 |
| 72.79 | 40 | EPA/16:0/16:1 | 0.5 | 851.7 | 868.6 | 549.4 |
| 73.82 | 40 | DHA/18:1/14:0 | 1.8 | 877.7 | 894.7 | 549.5, 621.5, 623.3 |
| 75.00 | 40 | DHA/16:0/14:0 | 1.7 | 851.8 | 868.8 | 523.5, 623.5 |
| 77.55 | 41 | EPA/15:0/16:0 | 0.8 | 839.7 | 856.7 | 537.5, 583.4 |
| 78.59 | 41 | DHA/16:0/15:0 | 2.5 | 865.6 | 882.8 | 537.3, 623.5 |
| 81.32 | 42 | EPA/16:0/16:0 | 5.5 | 853.7 | 870.7 | 551.5, 597.5 |
| 82.19 | 42 | DHA/16:0/16:0 | 21.7 | 879.8 | 896.7 | 551.5, 623.5 |
| 85.74 | 43 | DHA/17:0/16:0 | 2.0 | ND | 910.7 | 565.5, 623.5, 637.7 |
| 88.23 | 44 | DPA/16:0/16:0 | 0.8 | 881.7 | 898.8 | 551.7, 625.5 |
| 89.19 | 44 | DHA/16:0/18:0 | 3.2 | 907.9 | 924.8 | 579.5, 623.3, 651.5 |
| 93.18 | 46 | 16:0/16:0/16:1 | 1.2 | ND | 822.8 | 549.5, 551.6 |
| 94.57 | 46 | 16:0/16:0/14:0 | 1.1 | 779.7 | 796.7 | 523.4, 551.3 |
| 95.91 | 46 | DHA/12:0/24:0 | 0.7 | 935.9 | 952.8 | 567.5, 607.6 |
| 97.88 | 47 | 16:0/16:0/15:0 | 1.4 | ND | 810.7 | 537.5, 551.4 |
| 101.14 | 48 | 16:0/16:0/16:0 | 7.5 | 807.6 | 824.7 | 551.5 |
| 104.26 | 49 | 16:0/16:0/17:0 | 0.7 | ND | 838.7 | 551.4, 565.5 |
| 107.35 | 50 | 16:0/16:0/18:0 | 1.7 | ND | 852.8 | 551.5, 579.5 |
| 108.58 | 50 | DHA/16:0/24:0 | 0.7 | 991.8 | 1008.9 | 623.5, 663.7, 735.5 |
| 113.28 | 52 | 16:0/16:0/20:0 | 0.6 | ND | 880.9 | 551.5, 607.4 |
| 124.24 | 56 | 16:0/16:0/24:0 | 0.6 | ND | 936.8 | 551.5, 663.5 |

ND = Not Detected

TABLE 17

Identification of TAG Species in PTA-10212 Sample #2

| Retention Time | CN | Identification | Area Percent | [M + H]+ | [M + NH4]+ | (DAG) Fragments |
|---|---|---|---|---|---|---|
| 42.99 | 30 | EPA/EPA/DHA | 1.4 | 971.7 | 988.7 | 643.4, 669.5 |
| 44.22 | 30 | DHA/DHA/EPA | 3.3 | 997.8 | 1014.7 | 669.5, 695.5 |
| 45.4 | 30 | DHA/DHA/DHA | 2.4 | 1023.7 | 1040.8 | 695.5 |
| 54.80 | 34 | DHA/EPA/14:0 | 0.6 | 897.7 | 914.7 | 569.5 |
|  |  | DHA/DHA/16:1 |  | ND | 966.7 | 621.3 |
| 59.49 | 35 | DHA/15:0/DHA | 0.5 | ND | 954.8 | 609.6 |
| 60.83 | 36 | EPA/16:0/EPA | 1.6 | 899.7 | 916.6 | 597.5, 643.3 |
| 62.02 | 36 | EPA/16:0/DHA | 9.9 | 925.8 | 942.7 | 597.5, 623.5 |
| 63.16 | 36 | DHA/16:0/DHA | 13.0 | 951.8 | 968.8 | 623.6, 695.5 |
| 66.8 | 38 | DHA/18:0/EPA | 0.7 | 953.7 | 970.6 | 625.5 |
| 68.65 | 38 | DHA/ARA/16:0 | 0.4 | ND | 944.8 | 599.6, 623.4 |
| 69.76 | 38 | DHA/DPA/16:0 | 0.4 | 953.6 | 970.6 | 623.5 |
| 70.44 | 38 | DHA/DHA/18:0 | 0.3 | 979.8 | 996.7 | ND |
| 72.74 | 40 | EPA/16:0/16:1 | 0.4 | ND | 868.6 | 549.5 |
| 73.77 | 40 | DHA/18:1/14:0 | 1.6 | 877.6 | 894.8 | 549.5, 621.9 |
| 74.97 | 40 | DHA/16:0/14:0 | 1.4 | 851.8 | 868.7 | 523.5, 623.7 |
| 77.73 | 41 | EPA/15:0/16:0 | 0.3 | ND | 856.7 | 537.5 |
| 78.53 | 41 | DHA/16:0/15:0 | 2.2 | 865.8 | 882.7 | 537.5 |
| 81.32 | 42 | EPA/16:0/16:0 | 6.3 | 853.8 | 870.8 | 551.4, 597.5 |
| 82.15 | 42 | DHA/16:0/16:0 | 22.8 | 879.7 | 896.7 | 551.5, 623.5 |
| 85.67 | 43 | DHA/17:0/16:0 | 1.6 | ND | 910.8 | 565.5 |
| 89.08 | 44 | DPA/16:0/16:0 | 2.6 | ND | 898.8 | 551.5 |
|  |  | DHA/16:0/18:0 |  | 907.8 | 924.8 | 579.5 |
| 93.09 | 46 | 16:0/16:0/16:1 | 0.9 | ND | 822.8 | 549.6, 551.3 |
| 94.47 | 46 | 16:0/16:0/14:0 | 1.1 | ND | 796.7 | 523.5, 551.5 |
| 95.78 | 46 | DHA/12:0/24:0 | 0.5 | ND | 952.8 | 607.5 |
| 97.8 | 47 | 16:0/16:0/15:0 | 1.6 | ND | 810.7 | 537.3, 551.5 |
| 100.99 | 48 | 16:0/16:0/16:0 | 9.5 | ND | 824.7 | 551.4 |
| 104.11 | 49 | 16:0/16:0/17:0 | 0.6 | ND | 838.7 | 551.7, 565.5 |
| 107.23 | 50 | 16:0/16:0/18:0 | 2.1 | ND | 852.8 | 551.3, 579.5 |
| 108.45 | 50 | DHA/16:0/24:0 | 0.7 | ND | 1009.0 | 663.5 |
| 113.11 | 52 | 16:0/16:0/20:0 | 0.5 | ND | 880.9 | 551.3, 607.7 |
| 124.07 | 56 | 16:0/16:0/24:0 | 0.8 | ND | 937.0 | 551.5, 663.5 |

ND = Not Detected

PTA-10212 Sample #3

A sample of the TAG fraction of PTA-10212 Sample #3 was prepared in hexane and analyzed by HPLC/APCI/MS to determine the identities of individual TAG isomers.

TABLE 18

Identification of TAG Species in PTA-10212 Sample #3

| Retention Time | Peak # | Identification | Area Percent | [M + H]+ | [M + NH4]+ | (DAG) Fragments |
|---|---|---|---|---|---|---|
| 20.016 | 1 | EPA/EPA/EPA | 3.7 | 945.5 | 962.7 | 643.5 |
| 20.471 | 2 | EPA/EPA/DHA | 8.6 | 971.6 | 988.7 | 643.5, 669.5 |
| 20.970 | 3 | DHA/DHA/EPA | 6.5 | 997.7 | 1014.7 | 695.5, 669.5 |
| 21.441 | 4 | DHA/DHA/DHA | 3.7 | 1023.7 | 1040.7 | 695.5 |
| 21.855 | 5 | EPA/EPA/DPA | 0.7 | 973.7 | 990.7 | 645.3, 671.3 |
| 22.107 | 6 | DHA/EPA/DPA | 1.9 | 999.5 | 1016.7 | 697.5, 671.4 |
|  |  | EPA/EPA/ARA |  | 947.5 | 964.6 | 643.3, 645.3 |
| 22.573 | 7 | EPA/ARA/DHA | 2.2 | 973.7 | 990.7 | 671.5, 645.5 |
| 23.057 | 8 | DHA/EPA/DPA | 1.4 | 999.6 | 1016.7 | 696.5, 671.4 |
| 23.548 | 9 | DHA/DHA/DPA | 0.8 | 1025.7 | 1042.7 | 695.5, 697.5 |
|  |  | DHA/14:0/EPA |  | 897.7 | 914.7 | 569.4, 595.3 |
| 24.034 | 10 | DHA/16:1/EPA | 1.2 | 923.5 | 940.7 | 595.5, 621.3 |
| 24.306 | 11 | EPA/16:1/EPA | 0.7 | 897.6 | 914.7 | 595.3 |
| 24.509 | 12 | DHA/16:1/DHA | 0.8 | 949.6 | 966.7 | 621.3 |
| 24.783 | 13 | DHA/14:0/DHA | 0.5 | 923.7 | 940.8 | 595.5 |
| 25.571 | 14 | EPA/15:0/DHA | 1.0 | 911.7 | 928.7 | 583.4, 609.4 |
| 26.026 | 15 | DHA/15:0/DHA | 0.7 | 937.7 | 954.7 | 609.3 |
| 26.376 | 16 | EPA/16:0/EPA | 7.2 | 899.7 | 916.7 | 597.5 |
| 26.832 | 17 | EPA/16:0/DHA | 14.3 | 925.7 | 942.7 | 597.3, 623.4 |
| 27.272 | 18 | DHA/16:0/DHA | 13.2 | 951.7 | 968.7 | 623.5 |
| 27.842 | 19 | DPA/14:0/ARA | 0.5 | 901.6 | 918.7 | 599.4, 623.4 |
| 28.048 | 20 | EPA/18:0/EPA | 1.0 | 927.6 | 944.7 | 623.4 |
| 28.271 | 21 | DHA/16:0/ARA | 1.0 | 927.7 | 944.7 | 599.5, 623.5 |
| 28.564 | 22 | DPA/16:1/DPA | 2.3 | 953.7 | 970.6 | 623.5 |
|  |  | ARA/16:1/ARA |  | 901.8 | 918.6 | 597.4 |

TABLE 18-continued

Identification of TAG Species in PTA-10212 Sample #3

| Retention Time | Peak # | Identification | Area Percent | [M + H]+ | [M + NH4]+ | (DAG) Fragments |
|---|---|---|---|---|---|---|
| 29.060 | 23 | DHA/16:0/ARA | 2.6 | 927.7 | 944.7 | 599.3, 625.5 |
| 29.381 | 24 | DHA/18:0/EPA | 0.8 | 953.8 | 970.3 | 625.4, 651.5 |
| 29.512 | 25 | DHA/16:0//DPA | 1.0 | 953.8 | 970.8 | 623.4, 625.4 |
| 30.654 | 26 | DHA/16:0/16:1 | 1.4 | 877.8 | 894.7 | 549.5, 623.5 |
| 31.015 | 27 | DHA/16:0/14:0 | 0.6 | 851.7 | 868.7 | 523.3, 623.7 |
| 32.216 | 28 | DHA/16:0/15:0 | 0.8 | 865.8 | 882.7 | 537.5, 623.3 |
| 33.063 | 29 | EPA/16:0/16:0 | 4.1 | 853.5 | 870.7 | 551.5, 597.5 |
| 33.438 | 30 | DHA/16:0/16:0 | 9.7 | 879.7 | 896.7 | 551.5, 623.5 |
| 35.518 | 31 | DPA/16:0/16:0 | 0.9 | 881.7 | 898.7 | 551.5, ND |
| 35.798 | 32 | DHA/18:0/16:0 | 1.3 | 907.8 | 924.7 | 579.4, 651.3 |
| 39.578 | 33 | 16:0/16:016:0 | 1.3 | ND | 824.8 | 551.5 |

ND = Not Detected

PTA-10212 Sample #4

A sample of the TAG fraction of PTA-10212 Sample #4 was prepared in hexane and analyzed by HPLC/APCI/MS to determine the identities of individual TAG isomers.

PTA-10212 Sample #5

A sample of the TAG fraction of PTA-10212 Sample #5 was prepared in hexane and analyzed by HPLC/APCI/MS to determine the identities of individual TAG isomers.

TABLE 19

Identification of TAG Species in PTA-10212 Sample #4

| Retention Time | Peak # | Identification | Area Percent | [M + H]+ | [M + NH4]+ | (DAG) Fragments |
|---|---|---|---|---|---|---|
| 20.1 | 1 | EPA/EPA/EPA | 2.3 | 945.5 | 962.7 | 643.5 |
| 20.6 | 2 | EPA/EPA/DHA | 4.4 | 971.6 | 988.7 | 643.5, 669.5 |
| 21.1 | 3 | DHA/DHA/EPA | 4.7 | 997.7 | 1014.7 | 695.5, 669.5 |
| 21.6 | 4 | DHA/DHA/DHA | 4.1 | 1023.7 | 1040.7 | 695.5 |
|  |  | EPA/EPA/DPA |  | 973.7 | 990.7 | 645.3, 671.3 |
| 22.0 | 5 | EPA/EPA/DPA | 0.2 | 973.7 | 990.7 | 645.3, 671.3 |
| 22.3 | 6 | DHA/EPA/DPA | 1.4 | 999.5 | 1016.7 | 697.5, 671.4 |
|  |  | EPA/EPA/ARA |  | 947.5 | 964.6 | 645.3 |
| 22.7 | 7 | EPA/ARA/DHA | 1.1 | 973.7 | 990.7 | 671.5, 645.5 |
| 23.2 | 8 | DHA/EPA/DPA | 0.5 | 999.6 | 1016.7 | 696.5, 671.4 |
| 23.7 | 9 | DHA/DPA/DHA | 0.2 | 1025.8 | 1043.8 | 697.7 |
| 24.6 | 10 | DHA/16:1/DHA | 0.3 | 949.6 | 966.7 | 621.3 |
| 24.9 | 11 | DHA/14:0/EPA | 0.4 | 923.5 | 940.7 | 595.4 |
| 25.3 | 12 | EPA/15:0/EPA | 0.4 | 885.5 | 902.5 | 583.5 |
| 25.7 | 13 | EPA/15:0/DHA | 1.0 | 911.7 | 928.7 | 583.4, 609.4 |
| 26.2 | 14 | DHA/15:0/DHA | 0.6 | 937.7 | 954.7 | 609.3 |
| 26.6 | 15 | EPA/16:0/EPA | 4.9 | 899.7 | 916.7 | 597.5 |
| 27.0 | 16 | EPA/16:0/DHA | 12.8 | 925.7 | 942.7 | 597.3, 623.4 |
| 27.5 | 17 | DHA/16:0/DHA | 15.2 | 951.7 | 968.7 | 623.5 |
| 28.3 | 18 | EPA/18:0/EPA | 2.0 | 927.6 | 944.7 | 623.4 |
| 28.7 | 19 | DPA/16:1/DPA | 2.3 | 953.7 | 970.6 | 623.5 |
|  |  | ARA/16:1/ARA |  | 901.8 | 918.6 | 597.4 |
| 29.3 | 20 | DHA/16:0/ARA | 1.4 | 927.7 | 944.7 | 599.3, 623.4 |
| 29.6 | 21 | DHA/16:0/DPA | 1.5 | 953.8 | 970.3 | 625.4, 651.5 |
| 30.0 | 22 | DHA/18:0/DHA | 0.7 | 979.7 | 996.7 | 651.5 |
| 30.9 | 23 | DHA/16:0/16:1 | 0.7 | 877.8 | 894.7 | 549.5, ND |
|  |  | EPA/16:0/16:1 |  | 825.6 | 842.6 | 549.5, ND |
| 31.3 | 24 | DHA/14:0/16:0 | 0.6 | 851.7 | 868.7 | 523.3, 595.3 |
| 32.5 | 25 | DHA/16:0/15:0 | 1.5 | 865.8 | 882.7 | 537.5, 623.4 |
| 33.4 | 26 | EPA/16:0/16:0 | 4.4 | 853.5 | 870.7 | 551.5, 597.5 |
| 33.8 | 27 | DHA/16:0/16:0 | 14.5 | 879.7 | 896.7 | 551.5, 623.5 |
| 35.0 | 28 | DPA/16:0/16:0 | 2.3 | 881.6 | 898.7 | 551.5, 625.5 |
|  |  | DHA/15:0/18:0 |  | 893.8 | 910.7 | 565.5, ND |
| 35.8 | 29 | DPA/16:0/16:0 | 1.3 | 881.7 | 898.7 | 551.5, ND |
| 36.2 | 30 | DPA/16:0/16:0 | 2.6 | 881.7 | 898.7 | 551.5, 625.5 |
|  |  | DHA/16:0/18:0 |  | 907.8 | 924.7 | 579.4, 623.5 |
| 40.0 | 31 | 16:0/16:016:0 | 3.4 | ND | 824.8 | 551.5 |
| 42.2 | 32 | 16:0/16:0/18:0 | 0.7 | ND | 852.8 | 551.3, 579.5 |
| 43.0 | 33 | DHA/16:0/24:0 | 0.9 | 991.7 | 1008.8 | 623.3, 663.5 |

ND = Not Detected

TABLE 20

Identification of TAG Species in PTA-10212 Sample #5

| Retention Time | Peak # | Identification | Area Percent | [M + H]+ | [M + NH4]+ | (DAG) Fragments |
|---|---|---|---|---|---|---|
| 21.0 | 1 | EPA/EPA/EPA | 1.7 | 945.7 | 962.8 | 643.5 |
| 21.5 | 2 | EPA/EPA/DHA | 5.5 | 971.6 | 988.7 | 643.5, 669.5 |
| 22.0 | 3 | DHA/DHA/EPA | 7.6 | 997.7 | 1014.7 | 695.5, 669.5 |
| 22.5 | 4 | DHA/DHA/DHA | 4.5 | 1023.8 | 1040.7 | 695.5 |
| 23.0 | 5 | EPA/EPA/DPA | 0.5 | 973.8 | 990.8 | 645.5, 671.5 |
| 23.3 | 6 | DHA/EPA/DPA | 1.5 | 999.7 | 1016.7 | 697.5, 671.5 |
|  |  | EPA/EPA/ARA |  | 947.6 | 964.8 | 645.5 |
| 23.7 | 7 | EPA/ARA/DHA | 1.9 | 973.6 | 990.7 | 671.5, 645.4 |
|  |  | DHA/DPA/DHA |  | 1025.7 | 1042.7 | 695.5, 697.5 |
| 24.2 | 8 | DHA/EPA/DPA | 1.1 | 999.7 | 1016.7 | 669.5, 671.4, 696.5 |
| 24.8 | 9 | DHA/DHA/DPA | 0.6 | 1025.7 | 1042.9 | 695.5, 697.5 |
|  |  | DHA/14:0/EPA |  | 897.7 | 914.7 | 595.5 |
| 25.3 | 10 | DHA/16:1/EPA | 0.7 | 923.8 | 940.8 | 595.5, 621.3 |
| 25.6 | 11 | DHA/14:0/EPA | 0.6 | 897.7 | 914.7 | 569.3, 595.4 |
| 25.8 | 12 | DHA/16:1/DHA | 0.5 | 949.7 | 966.7 | 621.3, 695.5 |
| 26.0 | 13 | DHA/16:1/EPA | 0.4 | 923.7 | 940.8 | 595.5, 621.3 |
| 26.9 | 14 | EPA/15:0/DHA | 0.7 | 911.7 | 928.7 | 583.5, 609.3 |
| 27.4 | 15 | DHA/15:0/DHA | 0.7 | 937.6 | 954.8 | 609.3 |
| 27.8 | 16 | EPA/16:0/EPA | 4.9 | 899.7 | 916.7 | 597.5 |
| 28.2 | 17 | EPA/16:0/DHA | 14.3 | 925.7 | 942.8 | 597.5, 623.5 |
| 28.7 | 18 | DHA/16:0/DHA | 12.2 | 951.7 | 968.8 | 623.5 |
| 29.3 | 19 | DPA/14:0/ARA | 0.6 | 901.7 | 918.8 | 597.3 |
| 29.5 | 20 | EPA/18:0/EPA | 1.5 | 927.7 | 944.8 | 625.5 |
| 30.0 | 21 | DHA/16:0/ARA | 3.4 | 953.6 | 970.8 | 623.4 |
| 30.6 | 22 | EPA/EPA/18:0 | 2.1 | 927.7 | 944.7 | 599.5, 625.5, 669.3 |
| 31.0 | 23 | DHA/18:0/EPA | 1.7 | 953.8 | 970.8 | 625.4, 651.5 |
| 31.3 | 24 | DHA/18:0/DHA | 0.9 | 979.7 | 996.8 | 651.5, 695.3 |
| 31.9 | 26 | 16:0/DHA/14:0 | 0.8 | 851.7 | 868.7 | 595.5, 623.5 |
| 32.3 | 27 | 18:1/14:0/DHA | 1.7 | 877.7 | 894.7 | 549.5, 595.5 |
| 32.6 | 28 | DHA/16:0/14:0 | 0.9 | 851.8 | 868.7 | 523.4, 623.5 |
| 33.5 | 29 | EPA/15:0/16:0 | 0.7 | 839.7 | 856.7 | 537.5, 583.3 |
|  |  | DHA/20:0/EPA |  | 981.7 | 998.8 | 653.5, 679.6 |
| 33.9 | 30 | DHA/16:0/15:0 | 1.2 | 865.7 | 882.7 | 537.5, 623.5 |
| 34.8 | 31 | EPA/16:0/16:0 | 3.9 | 853.8 | 870.7 | 551.5, 597.5 |
| 35.2 | 32 | DHA/16:0/16:0 | 10.6 | 879.7 | 896.7 | 551.5, 623.5 |
| 36.4 | 33 | DPA/16:0/16:0 | 1.5 | 881.7 | 898.7 | 551.5, 625.5 |
| 37.4 | 33 | DPA/16:0/16:0 | 1.2 | 881.7 | 898.7 | 551.5, 625.5 |
| 37.7 | 34 | DHA/16:0/18:0 | 1.9 | 907.7 | 924.7 | 579.4 |
| 38.4 | 35 | EPA/24:0/DHA | 0.5 | 1037.8 | 1054.8 | 709.5, 735.6 |
| 38.8 | 36 | DHA/24:0/DHA | 1.0 | 1064.8 | 1081.8 | 735.7 |

EXAMPLE 5

Crude oils were further processed via refining, bleaching, and deodorizing to obtain refined oils. The refined oils were diluted with high oleic sunflower oil to obtain final oils with a DHA content of approximately 400 mg/g. Individual lipid classes were isolated and the fatty acid profiles of each class was determined using GC-FID as FAME.

PTA-10208 Final Oils

The fatty acid profiles for PTA-10208 Final Oils #1-5 are summarized in Tables 21-22, including profiles associated within the isolated TAG fraction (Tables 23-24) and the isolated sterols/DAG fraction (Tables 24-26).

Individual lipid classes in the final oils were also determined using flash chromatography (Table 27) and normal HPLC with ELSD and APCI-MS confirmation (Table 28).

TABLE 21

Fatty Acid Profiles of PTA-10208 Final Oils (mg/g)

| Fatty Acid | PTA-10208 Final Oil #1 FAME (mg/g) | PTA-10208 Final Oil #2 FAME (mg/g) | PTA-10208 Final Oil #3 FAME (mg/g) | PTA-10208 Final Oil #4 FAME (mg/g) | PTA-10208 Final Oil #5 FAME (mg/g) |
|---|---|---|---|---|---|
| C12:0 | 2.5 | 2.4 | 2.8 | 2.7 | 2.7 |
| C14:0 | 16.1 | 14.9 | 21.0 | 18.4 | 17.5 |
| C14:1 | 0.0 | 0.0 | 0.0 | 0.0 | 0.0 |
| C15:0 | 3.8 | 3.6 | 4.4 | 3.9 | 3.9 |
| C16:0 | 192.1 | 179.1 | 193.1 | 184.3 | 194.6 |
| C16:1 | 0.4 | 0.5 | 0.5 | 0.5 | 0.5 |
| C17:0 | 0.6 | 0.5 | 0.9 | 0.8 | 2.1 |
| C18:0 | 12.8 | 13.9 | 11.5 | 12.3 | 12.9 |
| C18:1 n-9 | 23.5 | 82.0 | 25.7 | 26.0 | 29.5 |
| C18:1 n-7 | 0.2 | 0.7 | 0.1 | 0.1 | 0.1 |
| C18:2 n-6 | 3.7 | 8.1 | 4.0 | 4.1 | 4.3 |
| C20:0 | 4.3 | 4.1 | 3.7 | 4.0 | 4.0 |

TABLE 21-continued

Fatty Acid Profiles of PTA-10208 Final Oils (mg/g)

| Fatty Acid | PTA-10208 Final Oil #1 FAME (mg/g) | PTA-10208 Final Oil #2 FAME (mg/g) | PTA-10208 Final Oil #3 FAME (mg/g) | PTA-10208 Final Oil #4 FAME (mg/g) | PTA-10208 Final Oil #5 FAME (mg/g) |
|---|---|---|---|---|---|
| C18:3 n-3 | 0.0 | 0.0 | 0.0 | 0.0 | 0.0 |
| C20:1 n-9 | <0.1 | 0.1 | <0.1 | <0.1 | <0.1 |
| C18:4 n-3 | 2.4 | 2.5 | 2.8 | 2.7 | 2.8 |
| C20:2 n-6 | 0.0 | 0.0 | 0.0 | 0.0 | 0.0 |
| C20:3 n-6 | 0.2 | 0.1 | 0.1 | 0.1 | 0.1 |
| C22:0 | 1.2 | 1.8 | 1.0 | 1.1 | 1.1 |
| C20:4 n-7 | 1.7 | 1.6 | 1.7 | 1.8 | 1.6 |
| C20:3 n-3 | 0.0 | 0.0 | 0.0 | 0.0 | 0.0 |
| C20:4 n-6 | 12.9 | 12.1 | 13.5 | 13.5 | 13.3 |
| C22:1 n-9 | 0.0 | 0.0 | 0.0 | 0.0 | 0.0 |
| C20:4 n-5 | 1.6 | 1.4 | 1.5 | 1.7 | 1.5 |
| C20:4 n-3 | 6.0 | 5.7 | 6.0 | 6.0 | 6.1 |
| C20:5 n-3 | 173.8 | 163.3 | 196.4 | 209.6 | 197.9 |
| C24:0 | 1.4 | 1.6 | 1.3 | 1.3 | 1.0 |
| C22:4\n-9 | 0.0 | 0.0 | 0.0 | 0.0 | 0.0 |
| C24:1 n-9 | 3.4 | 3.2 | 2.3 | 2.6 | 2.3 |
| C22:5 n-6 | 14.9 | 14.0 | 14.4 | 13.0 | 12.9 |
| C22:5 n-3 | 43.9 | 41.3 | 32.8 | 40.3 | 36.9 |
| C22:6 n-3 | 394.8 | 373.7 | 373.2 | 374.3 | 364.2 |
| Sum of FAME | 918.1 | 932.2 | 914.7 | 925.1 | 914.1 |

TABLE 22

Fatty Acid Profiles of PTA-10208 Final Oils (%)

| Fatty Acid | PTA-10208 Final Oil #1 % FAME | PTA-10208 Final Oil #2 % FAME | PTA-10208 Final Oil #3 % FAME | PTA-10208 Final Oil #4 % FAME | PTA-10208 Final Oil #5 % FAME |
|---|---|---|---|---|---|
| C12:0 | 0.3 | 0.3 | 0.3 | 0.3 | 0.3 |
| C14:0 | 1.8 | 1.6 | 2.3 | 2.0 | 1.9 |
| C14:1 | 0.0 | 0.0 | 0.0 | 0.0 | 0.0 |
| C15:0 | 0.4 | 0.4 | 0.5 | 0.4 | 0.4 |
| C16:0 | 20.9 | 19.2 | 21.1 | 19.9 | 21.3 |
| C16:1 | <0.1 | <0.1 | <0.1 | <0.1 | 0.1 |
| C17:0 | 0.1 | 0.1 | 0.1 | 0.1 | 0.2 |
| C18:0 | 1.4 | 1.5 | 1.3 | 1.3 | 1.4 |
| C18:1 n-9 | 2.6 | 8.8 | 2.8 | 2.8 | 3.2 |
| C18:1 n-7 | <0.1 | 0.1 | <0.1 | <0.1 | <0.1 |
| C18:2 n-6 | 0.4 | 0.9 | 0.4 | 0.4 | 0.5 |
| C20:0 | 0.5 | 0.4 | 0.4 | 0.4 | 0.4 |
| C18:3 n-3 | 0.0 | 0.0 | 0.0 | 0.0 | 0.0 |
| C20:1 n-9 | <0.1 | <0.1 | <0.1 | <0.1 | <0.1 |
| C18:4 n-3 | 0.3 | 0.3 | 0.3 | 0.3 | 0.3 |
| C20:2 n-6 | 0.0 | 0.0 | 0.0 | 0.0 | 0.0 |
| C20:3 n-6 | <0.1 | <0.1 | <0.1 | <0.1 | <0.1 |
| C22:0 | 0.1 | 0.2 | 0.1 | 0.1 | 0.1 |
| C20:4 n-7 | 0.2 | 0.2 | 0.2 | 0.2 | 0.2 |
| C20:3 n-3 | 0.0 | 0.0 | 0.0 | 0.0 | 0.0 |
| C20:4 n-6 | 1.4 | 1.3 | 1.5 | 1.5 | 1.5 |
| C22:1 n-9 | 0.0 | 0.0 | 0.0 | 0.0 | 0.0 |
| C20:4\n-5 | 0.2 | 0.2 | 0.2 | 0.2 | 0.2 |
| C20:4\n-3 | 0.7 | 0.6 | 0.7 | 0.7 | 0.7 |
| C20:5 n-3 | 18.9 | 17.5 | 21.5 | 22.7 | 21.6 |
| C24:0 | 0.1 | 0.2 | 0.1 | 0.1 | 0.1 |
| C22:4 n-9 | 0.0 | 0.0 | 0.0 | 0.0 | 0.0 |
| C24:1 n-9 | 0.4 | 0.3 | 0.2 | 0.3 | 0.2 |
| C22:5 n-6 | 1.6 | 1.5 | 1.6 | 1.4 | 1.4 |
| C22:5 n-3 | 4.8 | 4.4 | 3.6 | 4.4 | 4.0 |
| C22:6 n-3 | 43.0 | 40.1 | 40.8 | 40.5 | 39.9 |

TABLE 23

Isolated TAG Fatty Acid Profiles: PTA-10208 Final Oils (mg/g)

| Fatty Acid | PTA-10208 Final Oil #1 FAME (mg/g) | PTA-10208 Final Oil #2 FAME (mg/g) | PTA-10208 Final Oil #3 FAME (mg/g) | PTA-10208 Final Oil #4 FAME (mg/g) | PTA-10208 Final Oil #5 FAME (mg/g) |
|---|---|---|---|---|---|
| C12:0 | 2.5 | 2.3 | 2.7 | 2.5 | 2.6 |
| C14:0 | 16.3 | 15.1 | 21.3 | 18.6 | 18.1 |
| C14:1 | 0.0 | 0.0 | 0.0 | 0.0 | 0.0 |
| C15:0 | 3.9 | 3.6 | 4.4 | 4.0 | 4.0 |
| C16:0 | 194.2 | 181.9 | 196.1 | 186.1 | 199.8 |
| C16:1 | 0.4 | 0.4 | 0.6 | 0.5 | 0.7 |
| C17:0 | 0.6 | 0.5 | 0.9 | 0.8 | 0.8 |
| C18:0 | 12.9 | 14.2 | 11.7 | 12.5 | 13.2 |
| C18:1 n-9 | 24.3 | 84.0 | 26.8 | 26.1 | 34.0 |
| C18:1 n-7 | 0.1 | 0.7 | 0.1 | 0.1 | 0.3 |
| C18:2 n-6 | 3.2 | 7.7 | 3.4 | 3.5 | 4.0 |

TABLE 23-continued

Isolated TAG Fatty Acid Profiles: PTA-10208 Final Oils (mg/g)

| Fatty Acid | PTA-10208 Final Oil #1 FAME (mg/g) | PTA-10208 Final Oil #2 FAME (mg/g) | PTA-10208 Final Oil #3 FAME (mg/g) | PTA-10208 Final Oil #4 FAME (mg/g) | PTA-10208 Final Oil #5 FAME (mg/g) |
|---|---|---|---|---|---|
| C20:0 | 4.4 | 4.2 | 3.8 | 4.0 | 4.2 |
| C18:3 n-3 | 0.0 | 0.0 | 0.0 | 0.0 | 0.0 |
| C20:1 n-9 | <0.1 | 0.2 | <0.1 | <0.1 | 0.1 |
| C18:4 n-3 | 2.5 | 2.4 | 2.8 | 2.6 | 2.7 |
| C20:2 n-6 | 0.0 | 0.0 | 0.0 | 0.0 | 0.0 |
| C20:3 n-6 | 0.2 | 0.2 | 0.1 | 0.1 | 0.1 |
| C22:0 | 1.2 | 1.9 | 1.0 | 1.1 | 1.1 |
| C20:4 n-7 | 1.7 | 1.6 | 1.8 | 1.8 | 1.7 |
| C20:3 n-3 | 0.0 | 0.0 | 0.0 | 0.0 | 0.0 |
| C20:4 n-6 | 13.2 | 12.3 | 13.8 | 13.7 | 13.8 |
| C22:1 n-9 | 0.0 | 0.0 | 0.0 | 0.0 | 0.0 |
| C20:4 n-5 | 1.6 | 1.5 | 1.6 | 1.7 | 1.5 |
| C20:4 n-3 | 6.1 | 5.7 | 6.1 | 5.9 | 6.2 |
| C20:5 n-3 | 176.0 | 166.1 | 199.0 | 211.2 | 204.2 |
| C24:0 | 1.2 | 1.3 | 1.0 | 1.1 | 1.2 |
| C22:4 n-9 | 0.0 | 0.0 | 0.0 | 0.0 | 0.0 |
| C24:1 n-9 | 3.3 | 3.2 | 2.2 | 2.5 | 2.4 |
| C22:5 n-6 | 15.0 | 14.2 | 14.7 | 13.2 | 13.5 |
| C22:5 n-3 | 44.4 | 42.0 | 33.3 | 40.5 | 38.3 |
| C22:6 n-3 | 397.9 | 378.4 | 376.4 | 375.5 | 375.5 |
| Sum of FAME | 926.9 | 945.7 | 925.5 | 929.6 | 944.1 |

TABLE 24

Isolated TAG Fatty Acid Profiles: PTA-10208 Final Oils (%)

| Fatty Acid | PTA-10208 Final Oil #1 % FAME | PTA-10208 Final Oil #2 % FAME | PTA-10208 Final Oil #3 % FAME | PTA-10208 Final Oil #4 % FAME | PTA-10208 Final Oil #5 % FAME |
|---|---|---|---|---|---|
| C12:0 | 0.3 | 0.2 | 0.3 | 0.3 | 0.3 |
| C14:0 | 1.8 | 1.6 | 0.3 | 0.3 | 0.3 |
| C14:1 | 0.0 | 0.0 | 0.0 | 0.0 | 0.0 |
| C15:0 | 0.4 | 0.4 | 0.5 | 0.4 | 0.4 |
| C16:0 | 20.9 | 19.2 | 21.2 | 20.0 | 21.2 |
| C16:1 | <0.1 | <0.1 | 0.1 | 0.1 | 0.1 |
| C17:0 | 0.1 | 0.1 | 0.1 | 0.1 | 0.1 |
| C18:0 | 1.4 | 1.5 | 1.3 | 1.3 | 1.4 |
| C18:1 n-9 | 2.6 | 8.9 | 2.9 | 2.8 | 3.6 |
| C18:1 n-7 | <0.1 | 0.1 | <0.1 | <0.1 | <0.1 |
| C18:2 n-6 | 0.3 | 0.8 | 0.4 | 0.4 | 0.4 |
| C20:0 | 0.5 | 0.4 | 0.4 | 0.4 | 0.4 |
| C18:3 n-3 | 0.0 | 0.0 | 0.0 | 0.0 | 0.0 |
| C20:1 n-9 | <0.1 | <0.1 | <0.1 | <0.1 | <0.1 |
| C18:4 n-3 | 0.3 | 0.3 | 0.3 | 0.3 | 0.3 |
| C20:2 n-6 | 0.0 | 0.0 | 0.0 | 0.0 | 0.0 |
| C20:3 n-6 | <0.1 | <0.1 | <0.1 | <0.1 | <0.1 |
| C22:0 | 0.1 | 0.2 | 0.1 | 0.1 | 0.1 |
| C20:4 n-7 | 0.2 | 0.2 | 0.2 | 0.2 | 0.2 |
| C20:3 n-3 | 0.0 | 0.0 | 0.0 | 0.0 | 0.0 |
| C20:4 n-6 | 1.4 | 1.3 | 1.5 | 1.5 | 1.5 |
| C22:1 n-9 | 0.0 | 0.0 | 0.0 | 0.0 | 0.0 |
| C20:4 n-5 | 0.2 | 0.2 | 0.2 | 0.2 | 0.2 |
| C20:4 n-3 | 0.7 | 0.6 | 0.7 | 0.6 | 0.7 |
| C20:5 n-3 | 19.0 | 17.6 | 21.5 | 22.7 | 21.6 |
| C24:0 | 0.1 | 0.1 | 0.1 | 0.1 | 0.1 |
| C22:4 n-9 | 0.0 | 0.0 | 0.0 | 0.0 | 0.0 |
| C24:1 n-9 | 0.4 | 0.3 | 0.2 | 0.3 | 0.3 |
| C22:5 n-6 | 1.6 | 1.5 | 1.6 | 1.4 | 1.4 |
| C22:5 n-3 | 4.8 | 4.4 | 3.6 | 4.4 | 4.1 |
| C22:6 n-3 | 42.9 | 40.0 | 40.7 | 40.4 | 39.8 |

TABLE 25

Isolated Sterols/DAG Fatty Acid Profiles: PTA-10208 Final Oils (mg/g)

| Fatty Acid | PTA-10208 Final Oil #1 FAME (mg/g) | PTA-10208 Final Oil #2 FAME (mg/g) | PTA-10208 Final Oil #3 FAME (mg/g) | PTA-10208 Final Oil #4 FAME (mg/g) | PTA-10208 Final Oil #5 FAME (mg/g) |
|---|---|---|---|---|---|
| C12:0 | 1.9 | 2.1 | 2.9 | 2.1 | 1.9 |
| C14:0 | 9.9 | 9.5 | 9.7 | 10.3 | 8.0 |
| C14:1 | 0.0 | 0.0 | 0.0 | 0.0 | 0.0 |
| C15:0 | 2.4 | 2.3 | 2.2 | 2.3 | 2.0 |
| C16:0 | 132.6 | 128.6 | 110.1 | 116.8 | 106.4 |
| C16:1 | 0.2 | 0.3 | <0.1 | 0.3 | 0.4 |
| C17:0 | 0.3 | 0.2 | 0.3 | 0.3 | 0.3 |
| C18:0 | 7.3 | 8.1 | 6.4 | 6.8 | 6.1 |
| C18:1 n-9 | 15.0 | 55.1 | 47.4 | 19.0 | 30.1 |
| C18:1 n-7 | 0.4 | 0.7 | 0.1 | <0.1 | 0.2 |

TABLE 25-continued

Isolated Sterols/DAG Fatty Acid Profiles: PTA-10208 Final Oils (mg/g)

| Fatty Acid | PTA-10208 Final Oil #1 FAME (mg/g) | PTA-10208 Final Oil #2 FAME (mg/g) | PTA-10208 Final Oil #3 FAME (mg/g) | PTA-10208 Final Oil #4 FAME (mg/g) | PTA-10208 Final Oil #5 FAME (mg/g) |
|---|---|---|---|---|---|
| C18:2 n-6 | 13.1 | 16.7 | 21.6 | 13.5 | 18.4 |
| C20:0 | 2.0 | 2.1 | 1.2 | 1.8 | 1.4 |
| C18:3 n-3 | 0.0 | 0.0 | 0.0 | 0.0 | 0.0 |
| C20:1 n-9 | <0.1 | <0.1 | <0.1 | <0.1 | <0.1 |
| C18:4 n-3 | 2.3 | 2.4 | 2.4 | 2.4 | 2.0 |
| C20:2 n-6 | 0.0 | 0.0 | 0.0 | 0.0 | 0.0 |
| C20:3 n-6 | <0.1 | <0.1 | <0.1 | <0.1 | <0.1 |
| C22:0 | 0.6 | 1.0 | 0.5 | 0.6 | 0.5 |
| C20:4 n-7 | 0.8 | 0.9 | 2.1 | 0.9 | 0.7 |
| C20:3 n-3 | 0.0 | 0.0 | 0.0 | 0.0 | 0.0 |
| C20:4 n-6 | 5.7 | 5.8 | 4.8 | 6.1 | 4.5 |
| C22:1 n-9 | 0.0 | 0.0 | 0.0 | 0.0 | 0.0 |
| C20:4 n-5 | <0.1 | <0.1 | <0.1 | 0.6 | <0.1 |
| C20:4 n-3 | 2.7 | 2.7 | 2.1 | 2.7 | 2.0 |
| C20:5 n-3 | 92.9 | 94.5 | 91.9 | 111.6 | 84.8 |
| C24:0 | 1.2 | 1.3 | 1.1 | 1.1 | 1.3 |
| C22:4 n-9 | 0.0 | 0.0 | 0.0 | 0.0 | 0.0 |
| C24:1 n-9 | 1.9 | 2.0 | 1.2 | 1.5 | 1.2 |
| C22:5 n-6 | 7.8 | 8.0 | 6.7 | 7.0 | 5.5 |
| C22:5 n-3 | 22.2 | 22.9 | 13.9 | 20.7 | 14.2 |
| C22:6 n-3 | 246.3 | 252.7 | 223.5 | 240.3 | 196.3 |
| Sum of FAME | 569.3 | 619.8 | 552.1 | 568.7 | 488.2 |

TABLE 26

Isolated Sterols/DAG Fatty Acid Profiles: PTA-10208 Final Oils (%)

| Fatty Acid | PTA-10208 Final Oil #1 % FAME | PTA-10208 Final Oil #2 % FAME | PTA-10208 Final Oil #3 % FAME | PTA-10208 Final Oil #4 % FAME | PTA-10208 Final Oil #5 % FAME |
|---|---|---|---|---|---|
| C12:0 | 0.3 | 0.3 | 0.5 | 0.4 | 0.4 |
| C14:0 | 1.7 | 1.5 | 1.8 | 1.8 | 1.6 |
| C14:1 | 0.0 | 0.0 | 0.0 | 0.0 | 0.0 |
| C15:0 | 0.4 | 0.4 | 0.4 | 0.4 | 0.4 |
| C16:0 | 23.3 | 20.8 | 19.9 | 20.5 | 21.8 |
| C16:1 | <0.1 | <0.1 | <0.1 | <0.1 | 0.1 |
| C17:0 | 0.0 | 0.0 | 0.1 | 0.1 | 0.1 |
| C18:0 | 1.3 | 1.3 | 1.2 | 1.2 | 1.2 |
| C18:1 n-9 | 2.6 | 8.9 | 8.6 | 3.3 | 6.2 |
| C18:1 n-7 | 0.1 | 0.1 | <0.1 | <0.1 | <0.1 |
| C18:2 n-6 | 2.3 | 2.7 | 3.9 | 2.4 | 3.8 |
| C20:0 | 0.4 | 0.3 | 0.2 | 0.3 | 0.3 |
| C18:3 n-3 | 0.0 | 0.0 | 0.0 | 0.0 | 0.0 |
| C20:1 n-9 | <0.1 | <0.1 | <0.1 | <0.1 | <0.1 |
| C18:4 n-3 | 0.4 | 0.4 | 0.4 | 0.4 | 0.4 |
| C20:2 n-6 | 0.0 | 0.0 | 0.0 | 0.0 | 0.0 |
| C20:3 n-6 | <0.1 | <0.1 | <0.1 | <0.1 | <0.1 |
| C22:0 | 0.1 | 0.2 | 0.1 | 0.1 | 0.1 |
| C20:4 n-7 | 0.1 | 0.1 | 0.4 | 0.2 | 0.1 |
| C20:3 n-3 | 0.0 | 0.0 | 0.0 | 0.0 | 0.0 |
| C20:4 n-6 | 1.0 | 0.9 | 0.9 | 1.1 | 0.9 |
| C22:1 n-9 | 0.0 | 0.0 | 0.0 | 0.0 | 0.0 |
| C20:4 n-5 | <0.1 | <0.1 | <0.1 | 0.1 | <0.1 |
| C20:4 n-3 | 0.5 | 0.4 | 0.4 | 0.5 | 0.4 |
| C20:5 n-3 | 16.3 | 15.2 | 16.6 | 19.6 | 17.4 |
| C24:0 | 0.2 | 0.2 | 0.2 | 0.2 | 0.3 |
| C22:4 n-9 | 0.0 | 0.0 | 0.0 | 0.0 | 0.0 |
| C24:1 n-9 | 0.3 | 0.3 | 0.2 | 0.3 | 0.2 |
| C22:5 n-6 | 1.4 | 1.3 | 1.2 | 1.2 | 1.1 |
| C22:5 n-3 | 3.9 | 3.7 | 2.5 | 3.6 | 2.9 |
| C22:6 n-3 | 43.3 | 40.8 | 40.5 | 42.3 | 40.2 |

TABLE 27

Lipid class separation by flash chromatography (wt %)

| Lipid Class Separation | PTA-10208 Final Oil #1 | PTA-10208 Final Oil #2 | PTA-10208 Final Oil #3 | PTA-10208 Final Oil #4 | PTA-10208 Final Oil #5 |
|---|---|---|---|---|---|
| TAG | 93.4 | 95.4 | 94.0 | 95.7 | 95.1 |
| Sterols/DAG | 3.1 | 2.9 | 2.6 | 3.0 | 2.9 |
| Recovery (%) | 96.5 | 98.3 | 96.6 | 98.7 | 98.0 |

TABLE 28

Lipid class separation by HPLC-ELSD (wt %)

| | Sterol Esters | TAG | FFA | Sterols | 1,3-DAG | 1,2-DAG | MAG | Total |
|---|---|---|---|---|---|---|---|---|
| PTA-10208 Final Oil #1 | 0.4 | 90.8 | ND | 0.8 | 0.5 | 0.5 | N.D. | 93.0 |
| PTA-10208 Final Oil #2 | 0.4 | 88.5 | ND | 0.6 | 0.6 | 0.6 | N.D. | 90.7 |
| PTA-10208 Final Oil #3 | 0.3 | 89.4 | ND | 0.8 | 0.6 | 0.5 | N.D. | 91.6 |
| PTA-10208 Final Oil #4 | 0.3 | 88.0 | ND | 0.8 | 0.5 | 0.5 | N.D. | 90.1 |
| PTA-10208 Final Oil #5 | 0.3 | 86.3 | ND | 0.7 | 0.8 | 0.5 | N.D. | 88.6 |
| PTA-10208 Final Oil #6 | 0.36 | 100.76 | ND | 0.84 | 0.54 | 0.61 | N.D. | 103.11 |

ND = Not Detected

PTA-10212 Final Oil

DHA was present in a PTA-10212 Final Oil at 41.63% and 366.9 mg/g, while EPA was present at 16.52%. Individual fatty acid profiles were determined and are summarized in Table 29.

TABLE 29

Fatty Acid Profiles of PTA-10212 Final Oil (% FAME)

| Fatty Acid | % FAME |
|---|---|
| C6:0 | ND |
| C7:0 | ND |
| C8:0 | ND |
| C9:0 | ND |
| C10:0 | ND |
| C11:0 | ND |
| C12:0 | ND |
| C13:0 | ND |
| C14:0 | 0.84 |
| C14:1 | ND |
| C15:0 | 1.33 |
| C16:0 | 27.09 |
| C16:1 | 1.03 |
| C17:0 | 0.34 |
| C17:1 | ND |
| C18:0 | 1.26 |
| C18:1 n-9 | 2.14 |
| C18:1 n-7 | 0.18 |
| C19:0 | ND |
| C18:2 n-6 | 0.58 |
| C20:0 | 0.32 |
| C18:3 n-3 | ND |
| C20:1 n-9 | ND |
| C18:3 n-6 | ND |
| C20:2 n-6 | 0.26 |
| C20:3 n-6 | ND |
| C22:0 | 0.14 |
| C20:3 n-3 | ND |
| C20:4 n-6 | 1.34 |
| C22:1 n-9 | ND |
| C23:0 | ND |
| C20:5 n-3 | 16.53 |
| C24:0 | 0.53 |
| C24:1 n-9 | ND |
| C22:5 n-6 | 1.50 |
| C22:5 n-3 | 1.30 |
| C22:6 n-3 | 41.63 |
| Unknown | 0.87 |

ND = Not Detected

EXAMPLE 6

An analysis of the triacylglycerides (TAGs) of the PTA-10208 final oils described in Example 5 was performed using techniques described in Example 4. The identification of each fatty acid moiety was made, as summarized in Table 30 below.

TABLE 30

Identification of TAG Species in PTA-10208 Final Oil

| Identification | PTA-10208 Final Oil #1 Area % | PTA-10208 Final Oil #2 Area % | PTA-10208 Final Oil #3 Area % | PTA-10208 Final Oil #4 Area % | PTA-10208 Final Oil #5 Area % |
|---|---|---|---|---|---|
| EPA/EPA/EPA | 1.3 | 1.0 | 1.9 | 1.7 | 1.4 |
| EPA/EPA/DHA | 8.2 | 6.0 | 7.3 | 6.8 | 6.4 |
| DHA/DHA/EPA | 14.2 | 11.1 | 10.6 | 9.5 | 8.7 |
| DHA/DHA/DHA | 10.2 | 8.3 | 7.6 | 6.1 | 5.7 |
| DPA/EPA/EPA | 1.2 | 0.9 | 1.0 | 1.1 | 1.1 |
| DHA/DPA/EPA | 3.0 | 2.4 | 2.5 | 2.3 | 2.9 |
| DHA/EPA/ARA DHA/DPA/DHA | 3.8 | 3.0 | 3.0 | 3.0 | 2.3 |
| DHA/DPA/EPA | 2.3 | 1.9 | 1.5 | 1.6 | 1.7 |
| DHA/DPA/DHA | 1.7 | 1.2 | 1.1 | 1.2 | 1.2 |
| EPA/14:0/DHA | 1.1 | 1.0 | 1.8 | 1.8 | 1.5 |
| DHA/DHA/14:0 | 1.1 | 1.0 | 1.4 | 1.3 | 1.3 |
| EPA/EPA/16:0 | 2.3 | 2.3 | 3.4 | 3.9 | 3.3 |
| DHA/16:0/EPA | 12.1 | 12.5 | 12.9 | 14.0 | 13.4 |

TABLE 30-continued

Identification of TAG Species in PTA-10208 Final Oil

| Identification | PTA-10208 Final Oil #1 Area % | PTA-10208 Final Oil #2 Area % | PTA-10208 Final Oil #3 Area % | PTA-10208 Final Oil #4 Area % | PTA-10208 Final Oil #5 Area % |
|---|---|---|---|---|---|
| DHA/16:0/DHA | 16.1 | 16.8 | 17.5 | 14.8 | 17.2 |
| EPA/EPA/18:0 | 2.1 | 2.0 | 1.7 | 2.1 | 2.7 |
| DHA/DPA/16:0 | 3.0 | 3.3 | 2.3 | 2.9 | 2.7 |
| DHA/16:0/ARA | 1.6 | 1.6 | 1.8 | 2.0 | 2.2 |
| DHA/16:0/DPA | 1.3 | 2.1 | 1.4 | 1.5 | 2.5 |
| DHA/18:0/DHA | 0.8 | 0.8 | 0.7 | 0.8 | 1.0 |
| DHA/14:0/16:0 | 0.6 | 1.0 | 1.3 | 1.4 | 1.3 |
| EPA/16:0/16:0 | 0.9 | 1.1 | 1.5 | 1.7 | 2.0 |
| DHA/16:0/16:0 | 3.6 | 4.8 | 5.5 | 5.7 | 6.5 |
| 18:0/16:0/DHA | 0.4 | 0.8 | 0.7 | 0.8 | 1.2 |
| 18:1/18:1/18:1 | 0.6 | 4.0 | 1.0 | 1.4 | 1.6 |

EXAMPLE 7

A two-day old inoculum flask of the isolated microorganisms deposited under ATCC Accession Nos. PTA-10208 and 10212 was prepared as a carbon and nitrogen-fed culture in media according to Tables 1 and 2.

Mutagenesis was carried out according to following procedure:

A sterile T=2 day old flask, approximately 50 ml, was poured into a sterile 40 ml glass homogenizer. The culture received 50 plunges in the homogenizer. The culture was pipeted out and filtered through a sterile 50 micron mesh filter, which was placed in a 50 ml sterile tube (the mesh was used as a means of retaining the larger clumps of colonies while letting the smaller clusters and single cells pass through the 50 micron mesh.). The entire concentrated macerate was collected in a sterile 50 ml tube. The macerated culture was vortexed and dilutions at levels up to 1:100 fold were made. The diluted macerate samples were vortexed prior to adding 200 μl of inoculum to a media agar plate, 100×15 mm, containing 4-5 glass beads (3 mm glass beads). Each plate was gently agitated in an effort to have the beads spread the inoculum evenly around the plate. Beads were dumped off of plates and plates were left to sit with covers on for approximately 5 minutes to dry. Lights in both the sterile hood and adjoining areas were turned off as the procedure was performed in dim light. There was minimal light available to be able to run the procedure but only indirect and dim.

Five replicate plates were placed on the floor of the XL crosslinker (Spectronics Corporation, New York) with the lids off while the samples were irradiated. The crosslinker delivered power in terms of microjoules and a level was sought that achieved a 90%-95% Kill. Five replicate control plates were inoculated with un-mutagenized cells using the same protocol. These cell counts were used to calculate the % Kill. Once the irradiation was finished the plates were taken out, the lids were replaced, and the plates were wrapped in parafilm followed by a wrap in aluminum foil. It was imperative that the plates grew for the first week in the dark so that they were not able to repair the damaged genes.

Plates were placed in a 22.5° C. room for about 10 days prior to counting the colonies. When final counts were made, individual colonies were picked with a sterile inoculating loop and re-streaked on new media plates. Each colony was plated on an individual plate. As plates grew dense a sample was taken, using a inoculating loop, and inoculated into a sterile 250 ml shake flask containing 50 ml of media. This flask was placed on a shaker at 200 rpm in a 22.5° C. room.

On T=7 days the shake flask culture was harvested into a 50 ml sterile tube. The pH was taken and the sample was centrifuged to collect the biomass pellet. Each sample was rinsed and re-suspended in a 50:50 mixture of isopropyl alcohol and distilled water prior to being re-centrifuged. The collected pellet was freeze dried, weighed, and a FAME analysis was performed. The data in Tables 31 and 32 represents mutants produced with the above process from strains PTA-10208 and PTA-10212, respectively.

TABLE 31

PTA-10208 Mutants

| Fatty Acids | control PTA-10208 | Mutant 1 PTA-10209 | Mutant 2 PTA-10210 | Mutant 3 PTA-10211 |
|---|---|---|---|---|
| % 08:0 | 0.00 | 0.00 | 0.00 | 0.00 |
| % 09:0 | 0.00 | 0.00 | 0.00 | 0.00 |
| % 10:0 | 0.00 | 0.00 | 0.00 | 0.00 |
| % 11:0 | 0.00 | 0.00 | 0.00 | 0.00 |
| % 11:1 | 0.00 | 0.00 | 0.00 | 0.00 |
| % 12:0 | 0.11 | 0.10 | 0.22 | 0.19 |
| % 12:1 | 0.00 | 0.00 | 0.00 | 0.00 |
| % 13:0 | 0.19 | 0.19 | 0.15 | 0.16 |
| % 13:1 | 0.00 | 0.00 | 0.00 | 0.00 |
| % 14:0 | 1.94 | 1.82 | 2.98 | 2.59 |
| % 14:1 | 0.00 | 0.00 | 0.00 | 0.00 |
| % 15:1 | 2.66 | 2.22 | 1.76 | 1.66 |
| % 16:0 | 24.87 | 24.97 | 23.71 | 25.01 |
| % 16:1 | 0.20 | 0.25 | 0.07 | 0.07 |
| % 16:2 | 0.00 | 0.00 | 0.00 | 0.00 |
| % 16:3 | 0.00 | 0.00 | 0.00 | 0.00 |
| % 17:0 | 1.49 | 1.21 | 0.62 | 0.66 |
| % 18:0 | 1.13 | 1.14 | 0.91 | 1.01 |
| % 18:1 n-9 | 0.07 | 0.07 | 0.06 | 0.06 |
| % 18:1 n-7 | 0.00 | 0.00 | 0.00 | 0.00 |
| % 18:2 | 0.00 | 0.00 | 0.00 | 0.00 |
| % 18:3 n-6 | 0.00 | 0.00 | 0.05 | 0.04 |
| % 18:3 n-3 | 0.09 | 0.08 | 0.17 | 0.14 |
| % 18:4 n-3 | 0.00 | 0.00 | 0.00 | 0.00 |
| % 20:0 | 0.31 | 0.33 | 0.24 | 0.30 |
| % 20:1 n-9 | 0.00 | 0.04 | 0.00 | 0.00 |
| % 20:2 | 0.00 | 0.00 | 0.05 | 0.00 |
| % 20:3 n-9 | 0.00 | 0.00 | 0.00 | 0.00 |
| % 20:3 n-6 | 0.12 | 0.13 | 0.08 | 0.04 |
| % 20:3 n-3 | 0.42 | 0.42 | 0.08 | 0.06 |
| % 20:4 ARA | 0.68 | 0.67 | 1.44 | 1.11 |
| % 20:5 n-3 EPA | 6.56 | 6.47 | 11.99 | 9.87 |
| % 22:0 | 0.07 | 0.07 | 0.06 | 0.07 |
| % 22:1 | 0.00 | 0.00 | 0.00 | 0.00 |
| % 22:2 | 0.11 | 0.09 | 0.10 | 0.08 |
| % 22:3 | 0.00 | 0.00 | 0.00 | 0.00 |
| % 22:4 n-6 | 0.00 | 0.00 | 0.00 | 0.00 |
| % 22:5 n-6 | 2.32 | 2.36 | 2.36 | 2.36 |
| % 22:5 n-3 | 0.48 | 0.66 | 0.66 | 0.52 |

TABLE 31-continued

PTA-10208 Mutants

| Fatty Acids | control PTA-10208 | Mutant 1 PTA-10209 | Mutant 2 PTA-10210 | Mutant 3 PTA-10211 |
|---|---|---|---|---|
| % 22:6 n-3 DHA | 51.58 | 52.27 | 48.17 | 49.35 |
| % 24:0 | 0.00 | 0.00 | 0.00 | 0.00 |
| % 24:1 | 0.00 | 0.00 | 0.00 | 0.00 |
| % Fat | 47.87 | 49.41 | 66.00 | 63.12 |
| % Unknown | 4.61 | 4.45 | 4.07 | 4.64 |

TABLE 32

PTA-10212 Mutants

| Fatty Acids | Control PTA-10212 | Mutant 1 PTA-10213 | Mutant 2 PTA-10214 | Mutant 3 PTA-10215 |
|---|---|---|---|---|
| % 08:0 | 0.00 | 0.00 | 0.00 | 0.00 |
| % 09:0 | 0.00 | 0.00 | 0.00 | 0.00 |
| % 10:0 | 0.00 | 0.00 | 0.00 | 0.00 |
| % 11:0 | 0.00 | 0.00 | 0.00 | 0.00 |
| % 11:1 | 0.00 | 0.00 | 0.00 | 0.00 |
| % 12:0 | 0.00 | 0.00 | 0.00 | 0.00 |
| % 12:1 | 0.00 | 0.00 | 0.00 | 0.00 |
| % 13:0 | 0.00 | 0.00 | 0.21 | 0.20 |
| % 13:1 | 0.00 | 0.00 | 0.00 | 0.00 |
| % 14:0 | 0.68 | 0.77 | 0.62 | 0.97 |
| % 14:1 | 0.00 | 0.00 | 0.00 | 0.00 |
| % 15:1 | 0.00 | 0.00 | 0.00 | 0.00 |
| % 16:0 | 17.36 | 19.94 | 15.27 | 23.61 |
| % 16:1 | 1.45 | 2.33 | 1.40 | 2.57 |
| % 16:2 | 0.00 | 0.00 | 0.00 | 0.00 |
| % 16:3 | 0.00 | 0.00 | 0.00 | 0.00 |
| % 17:0 | 0.20 | 0.21 | 0.18 | 0.27 |
| % 18:0 | 0.78 | 0.82 | 0.79 | 0.81 |
| % 18:1 n-9 | 0.00 | 0.00 | 0.00 | 0.00 |
| % 18:1 n-7 | 0.18 | 0.27 | 0.20 | 0.19 |
| % 18:2 | 0.00 | 0.00 | 0.00 | 0.00 |
| % 18:3 n-6 | 0.00 | 0.00 | 0.00 | 0.00 |
| % 18:3 n-3 | 0.00 | 0.00 | 0.00 | 0.00 |
| % 18:4 n-3 | 0.00 | 0.00 | 0.00 | 0.00 |
| % 20:0 | 0.00 | 0.00 | 0.00 | 0.00 |
| % 20:1 n-9 | 0.00 | 0.00 | 0.00 | 0.00 |
| % 20:2 | 0.00 | 0.00 | 0.00 | 0.00 |
| % 20:3 n-9 | 0.00 | 0.00 | 0.00 | 0.00 |
| % 20:3 n-6 | 0.00 | 0.00 | 0.00 | 0.00 |
| % 20:3 n-3 | 0.90 | 0.77 | 0.99 | 0.66 |
| % 20:4 ARA | 1.43 | 1.32 | 1.65 | 0.72 |
| % 20:5 n-3 EPA | 13.33 | 14.93 | 14.14 | 8.54 |
| % 22:0 | 0.00 | 0.00 | 0.00 | 0.00 |
| % 22:1 | 0.00 | 0.00 | 0.00 | 0.00 |
| % 22:2 | 0.00 | 0.00 | 0.00 | 0.00 |
| % 22:3 | 0.00 | 0.00 | 0.00 | 0.00 |
| % 22:4 n-6 | 0.00 | 0.00 | 0.00 | 0.00 |
| % 22:5 n-6 | 2.39 | 1.95 | 2.59 | 2.18 |
| % 22:5 n-3 | 0.73 | 0.79 | 0.80 | 0.68 |
| % 22:6 n-3 DHA | 59.18 | 54.31 | 59.89 | 56.39 |
| % 24:0 | 0.00 | 0.00 | 0.00 | 0.00 |
| % 24:1 | 0.00 | 0.00 | 0.00 | 0.00 |
| % Fat | 45.69 | 38.08 | 42.88 | 48.48 |
| % Unknown | 1.38 | 1.58 | 1.27 | 2.19 |

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed:

1. A blended oil composition comprising a vegetable oil and a microbial oil comprising a polyunsaturated fatty acids (PUFA) fraction produced from a single isolated strain of thraustochytrid microorganism, wherein said PUFA fraction comprises a triacylglycerol fraction which is at least 10% by weight of said PUFA fraction, wherein at least 12% by weight of the fatty acids in the triacylglycerol fraction is eicosapentaenoic acid (EPA), wherein at least 25% by weight of the fatty acids in the triacylglycerol fraction is docosahexaenoic acid (DHA), and wherein less than 5% by weight of the fatty acids in the triacylglycerol fraction is arachidonic acid (ARA), wherein said thraustochytrid microorganism is of the genus *Schizochytrium* or *Thraustochytrium*, and wherein said refined oil further comprises an effective amount of at least one added antioxidant to provide oxidative stability.

2. The vegetable oil of claim 1, wherein the triacylglycerol fraction is at least 40% by weight of said PUFA fraction.

3. The vegetable oil of claim 1, wherein at least 15% by weight of the fatty acids in the triacylglycerol fraction is eicosapentaenoic acid.

4. The vegetable oil of claim 1, wherein at least 35% by weight of the fatty acids in the triacylglycerol fraction is docosahexaenoic acid.

5. The vegetable oil of claim 1, wherein 2% or less by weight of the fatty acids in the triacylglycerol fraction is arachidonic acid.

6. The vegetable oil of claim 1, wherein the fatty acids comprise less than about 5% by weight each of oleic acid, linoleicacid, linolenic acid, eicosenoic acid, and erucic acid.

* * * * *

SEQUENCE LISTING

<160> NUMBER OF SEQ ID NOS: 2

<210> SEQ ID NO 1
<211> LENGTH: 1705
<212> TYPE: DNA
<213> ORGANISM: Thraustochytrium sp.

<400> SEQUENCE: 1

```
aagatacctg gttgatcctg ccagtagtca tacgctcgtc tcaaagatta agccatgcat      60
gtgtcagtat aaatactttt actttgaaac tgcgaacggc tcattaaatc agtaattatc     120
tacatggtaa cgaaaattat atggataacc gtagtaattc tagggctaat acatgcgtaa     180
aatctgggta actggatgca tttattggat tgaagccaac attaaaaggt gattcacgat     240
aactaagcgg agcgttttag gacgctgaat cattcgagtt tctgccctat cagctgtcga     300
tggtaaggta ttggcttacc atggcgttaa cgggtaacgg agaattaggg ttcgattccg     360
gagagggagc ctgagagacg gctaccacat ccaaggaagg cagcaggcgc gtaaattgcc     420
caatgagaac ttctcgaggc agtgacaaga aatatcaaag tgatgccgtt aggtattgca     480
tttgaaatga gaacgatgta caacttctaa cgatgatcaa ttggagggca agtctggtgc     540
cagcagccgc ggtaattcca gctccaatag cgtatactaa cgttgctgca gttaaaacgc     600
ccgtagttga attagtatca tggtatttta accttattcg atgaatttga gttgaaagct     660
aggatatata ggaagcgatt cctcatttac tgtaaaaaaa ttagagtgtt tcacacagat     720
```

```
cgtaagatcg ggatatatta gtatggaata ataagatagg actttggtgc tattttgttg      780
gtttgcacac caaagtaatg attaataggg acagttgggg gtattcgtat ttaattgtca      840
gaggtgaaat tcttggattt atgaaagacg aactactgcg aaagcattta ccaaggatgt      900
tttcattaat caaggacgaa agttagggga tcgaagatga ttagatacca tcgtagtctt      960
aaccataaac tatgccgact gaggattctt gaaatttgta aatgaattta agagcactcc     1020
atgagaaatc aaagtctttg ggttccgggg ggagtatggc cgcaagtctg aaacttaaag     1080
gaattgacgg aagggcacca ccaggagtgg agcctgcggc ttaatttgac tcaacacggg     1140
aaaacttacc aggtccagac atagtgagga ttgacagatt gatagctctt tcttgattct     1200
atgggtggtg gtgcatggcc gttcttagtt ggtggtttga actgtctgct taattgcgtt     1260
aacgaacgag acctcagcct actaaatagt atgttgttta gtaataaatg atatgacttc     1320
ttagagggac atttcgggtt taccggaagg aagtttgagg caataacagg tctgtgatgc     1380
ccttagatgt tctgggccgc acgcgcgcta cactgacgag ctcaacaagt aatatttggt     1440
tgtctggaag gattgcctaa tcttttaaat actcgtcgtg atggggctag attcttgtaa     1500
ttattaatct ccaacgagga attcctagta acgcaagtc atcagcttgc attgattacg      1560
tccctgccct tgtacacac cgcccgtcgc acctaccgat tggatggtcc ggtgaaatct      1620
tcggatgttt tttacaata gtagagagac aaaagttgag taaaccttac catctagagg      1680
aaggtgaagt cgtaacaagg atctt                                            1705
```

<210> SEQ ID NO 2
<211> LENGTH: 1713
<212> TYPE: DNA
<213> ORGANISM: Schizochytrium sp.

<400> SEQUENCE: 2

```
acctggttga tcctgccagc tgtcatttgc tcgtctaaaa gattaagcca tgcatgtcta       60
agtataaaca aattatacgg tgaaactgcg aacggctcat tatatcagtt atagtttctt      120
tgatagtgta tttctatatc tatttggata actgtggcaa ttctagagct aacacatgct      180
ttcgagtggg acttttttggt accactgcat ttattagatt ttgaagccaa cgtaaaattg     240
gtgattcatg ataactttgc gaatcgcagt agcgtcttgt acgcggcgat gaatcattca      300
agtttctgcc ccatcagctg tcgatggtac ggtattggcc taccatggct ttcacgggtg      360
acggagaatt agggtttgat tccggagagg acgcttgaga gacggcgacc acatccaagg      420
aaggcagcag gcgcgtaaat tacccaatgg ggactccccg aggtagtgac aagaaataaa      480
aatgaggagc gctttgcgtt tttcaatttg aatgagagaa tcgtacaatc ctcatcgagg      540
atcaattgga gggcaagtct ggtgccagca gccgcggtaa ctccagctcc aatagcaaat      600
attagagttg ttgcagttaa aaagctcgta gttgaatttc cgatagtctt tggccgtgtc      660
cttggtctcg tatcatgggt ttattgtgcc aagatgatcg tcctctatgg ttagtgatag      720
tcatagtcgt ttactgtaaa aaaactggag tgtttaaagc atttctttgg gaaaggtaca      780
tattagtata ggataattag ataggacctg tgattcttat ttggttggtt tgtgagtcat      840
ggtaatgatt aataggggaca atcggggggta ttcgaattta attgtcagag gtgaaattct     900
tggatttaag aaagtcgaac tactgcgaag gcatttacca aggatgtttt cattaataaa      960
gaacgaaagt tagggggatcg aagatgatta gataccatcg tagtcttaac tgtaaactat     1020
gccgacttgc gattgtccgt cgttgttttt tcaaaaaaga gacctgggca gcagcacatg     1080
```

```
agaaatcaaa gtttttgggt tccgggggga gtatggtcgc aaggctgaaa cttaaaggaa    1140
ttgacggaag ggcaccacca ggagtggagc ctgcggctta attcgactca acacgggaaa    1200
acttaccagg tccagacata gtaaggattg acagattgag agctctttct tgattctatg    1260
ggtggtggtg catggccgtt cttagttggt ggagtgattt gtctggttaa ttccgttaac    1320
gaacgagacc tcagcctact aaatagtggt gcatattgtg agatatgtga caaaaatcgc    1380
ttcttagagg gacatttcgg gtttaccgga aggaagtttg aggcaataac aggtctgtga    1440 tgccccctaga tgttctgggc cgcacgcgcg ctacaatgac agattcaaca agtccggtag   1500
tggagctttt gcttctctat tattactttt ccgagaggaa tggttaatct tctaaatgtc    1560
tgtcgtgatg gggctagatt tttgcaatta ttaatctcca acgaggaatt cctagtaaac    1620
gcaagtcatc agcttgcatt gattacgtcc ctgccctttg tacacaccgc ccgtcgcacc    1680
taccgattga acggtcctat gaaatcttcg gat                                 1713
```